(12) United States Patent
Scheibel et al.

(10) Patent No.: US 7,951,908 B2
(45) Date of Patent: *May 31, 2011

(54) RECOMBINANT SPIDER SILK PROTEINS

(75) Inventors: Thomas Scheibel, Munich (DE); Daniel Huemmerich, Mannheim (DE); Christian Ackerschott, Munich (DE)

(73) Assignee: Amsilk GmbH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/785,960

(22) Filed: May 24, 2010

(65) Prior Publication Data

US 2010/0298877 A1 Nov. 25, 2010

Related U.S. Application Data

(62) Division of application No. 11/654,470, filed on Jan. 17, 2007, now Pat. No. 7,754,851.

(60) Provisional application No. 60/590,196, filed on Jul. 22, 2004.

(51) Int. Cl.
  *A61K 38/00* (2006.01)
  *C07K 14/00* (2006.01)
  *C07K 17/00* (2006.01)

(52) U.S. Cl. .................. 530/300; 530/324; 530/350

(58) Field of Classification Search .................. None
See application file for complete search history.

(56) References Cited

FOREIGN PATENT DOCUMENTS

WO  WO 03/057727  7/2003

OTHER PUBLICATIONS

Arcidiacono et al. Purification and characterization of recombinant spider silk expressed in *Escherichia coli.*, Applied Microbiology and Biotechnology, vol. 49, No. 1, 1998, pp. 31-38.
Fahnestock et al., Synthetic spider dragline silk proteins and their production in *Escherichia coli*, Applied Microbiology and Biotechnology, vol. 47, No. 1, 1997, pp. 23-32.
Guerette, et al., Silk properties determined by gland-specific expression of a spider fibroin gene family, Science, vol. 272, 1996, pp. 112-115.
Guerette, et al., GenBank accession No. U47856.1, Publicly available since 1996, Retrieved from the Internet. <URL:http://www.ncbi. nlm.nih.gov/protein/1263289?ordinalpos=1&itool=EntrezSystem2. PEntrez.Sequence.Sequence_ResultsPanel.Sequence_RVDocSum>.
Hayashi, et al., Evidence from Flagelliform silk cDNA for the structural basis of elasticity and modular nature of spider silk, Journal of Molecular VBiology, vol. 275, 1998, pp. 773-784.
Hinman, et al., Isolation of a clone encoding a second dragline silk fibroin, The Journal of Biological Chemistry, vol. 267, No. 27, 1992, pp. 19320-19324.
Hinman, et al. Synthetic spider silk: a modulator fiber, Trends in Biotechnology, vol. 18, 2000, pp. 374-379.
Huemmerich, et al., Novel assembly properties of recombinant spider dragline silk protein, Current Biology, vol. 14, No. 22, 2004, pp. 2070-2074.
Huemmerich, et al., Primary structure elements of spider dragline silks and their contribution to protein solubility, Biochemistry, vol. 43, No. 42, 2004, pp. 13604-13612.
International Preliminary Report on Patentability corresponding to PCT Application No. PCT/EP2005/007968 dated Oct. 18, 2006.
International Search Report corresponding to PCT Application Nol. PCT/EP2005/007968 dated Mar. 20, 2006.
Lazaris, et al., Spider silk fibers spun from soluble recombinant silk produced in mammalian cells, Science, vol. 295, No. 5554, 2002, pp. 472-476.
Lewis, et al., Expression and purification of a spider silk protein: a new strategy for producing repetitive proteins, Protein Expression and Purification, vol. 7, No. 4, 1996, pp. 400-406.
Prince, et al., Construction, cloning and expression of synthetic genes encoding spider dragline silk, Biochemistry, vol. 34, 1995, pp. 10879-10885.
Scheller, et al., Production of spider silk proteins in tobacco and potato, Nature Biotechnology, vol. 19, No. 6, 2001, pp. 573-577.
Wong Po Foo, et al., Genetic engineering of fibrous proteins: spider dragline silk and collagen, Advanced Drug Delivery Reviews, vol. 54, 2002, pp. 1131-1143.
Kisselev, Structure, vol. 10, pp. 8-9, 2002.
Branden, et al., "Introduction to Protein Structure Second Edition", Garland Publishing, New York, 1999.
Witkowski, et al., Biochemistry, 38, 11643-11650, 1999.
Wishart, et al., Journal of Biological Chemistry, vol. 270, No. 45, pp. 26782-26785, 1995.

*Primary Examiner* — Suzanne M Noakes
*Assistant Examiner* — Jae W Lee
(74) *Attorney, Agent, or Firm* — Baker & Daniels LLP

(57) ABSTRACT

The present invention is directed to recombinant spider silk proteins, nucleic acids, coding for these recombinant spider silk proteins, as well as hosts suitable for expressing those nucleic acids. Furthermore, the present invention is directed to a method of aggregation of spider silk proteins and the use of the proteins in the field of biotechnology and/or medicine and other industrial fields, in particular in the manufacture of automotive parts, in the aircraft construction, in the processing of textiles and leather, as well as in the manufacture and processing of paper and the like.

29 Claims, 15 Drawing Sheets

RECOMBINANT SPIDER SILK PROTEINS

Figure 1:
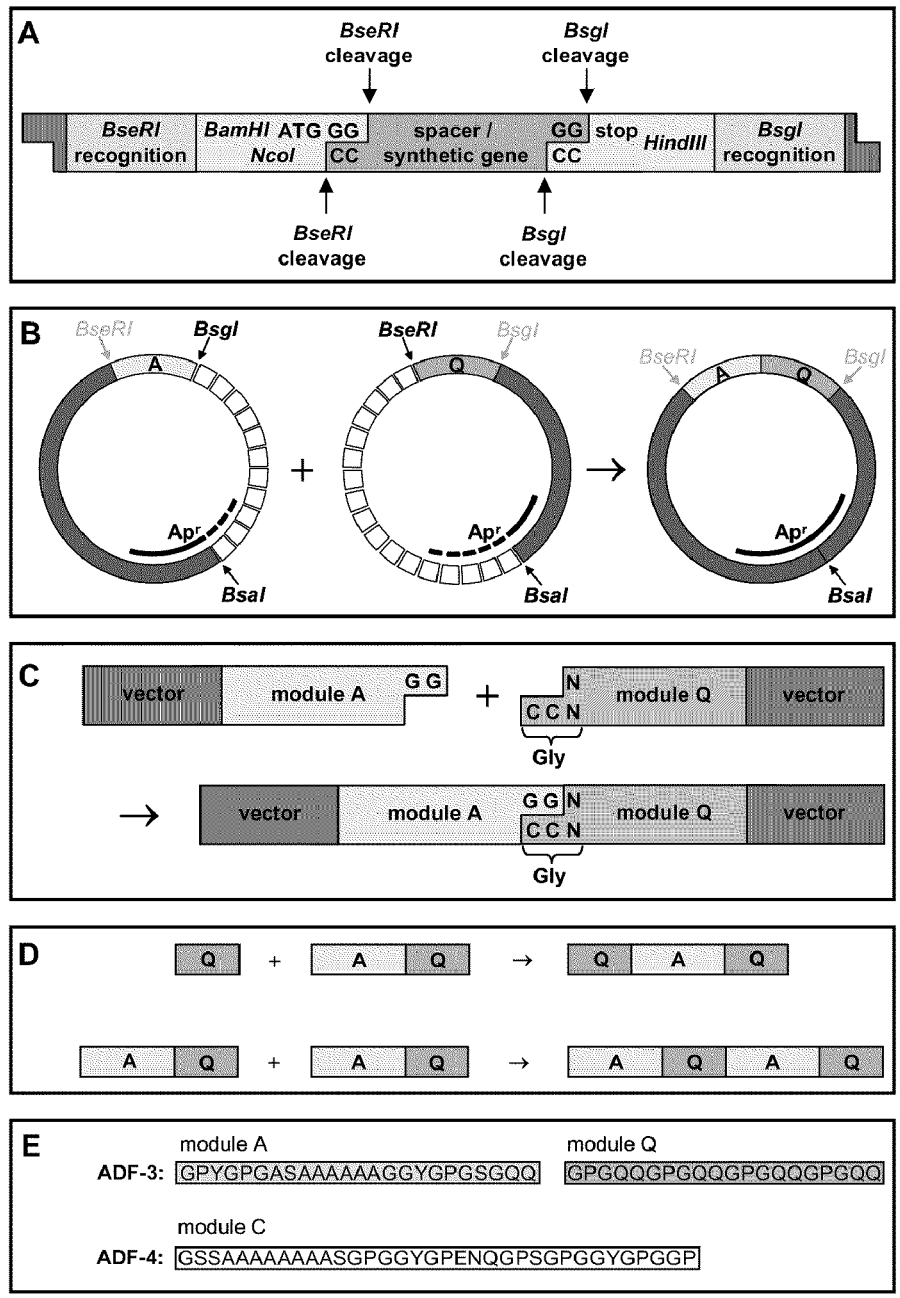

This application is a divisional of U.S. patent application Ser. No. 11/654,470, filed Jan. 17, 200, which is a continuation based on International Application No. PCT/EP05/07968 filed Jul. 21, 2005 based on U.S. Provisional Patent Application Ser. No. 60/590,196 filed Jul. 22, 2004, the disclosures of which are hereby explicitly incorporated by reference herein.

The present invention is directed to recombinant spider silk proteins, nucleic acids, coding for these recombinant spider silk proteins, as well as hosts suitable for expressing those nucleic acids. Furthermore, the present invention is directed to a method of aggregation of spider silk proteins and the use of the proteins in the field of biotechnology and/or medicine and other industrial fields, in particular in the manufacture of automotive parts, in the aircraft construction, in the processing of textiles and leather, as well as in the manufacture and processing of paper, cometics, food, electronic devices, drug delivery and the like.

In this application, the following abbreviations will be used:
NR, non-repetitive; $Ap^r$, ampicillin resistance gene; IPTG, Isopropyl-β-D-thiogalactosid; GdmCl, guanidinium chloride; GdmSCN, guanidinium thiocyanate; SDS, sodium dodecylsulfate; PAGE, polyacrylamide gel electrophoresis; Tris, Tris(hydroxymethyl)aminomethane; CD, circular dichroism; rep-proteins, repetitive proteins; Da, Dalton; cps, counts per second; MRW, mean residue weight; n.d., not determined.

Spider silks are protein polymers that display extraordinary physical properties (1). Among the different types of spider silks, draglines are most intensely studied. Dragline silks are utilized by orb weaving spiders to build frame and radii of their nets and as lifelines that are permanently dragged behind. For these purposes high tensile strength and elasticity are required. The combination of such properties results in a toughness that is higher than that of most other known materials (1 ;2). Dragline silks are generally composed of two major proteins whose primary structures share a common repetitive architecture (3 ;4).

Variations of a single repeat unit, which can comprise up to 60 amino acids, are iterated several times to represent the largest part of a dragline silk sequence. These repeat units comprehend a limited set of distinct amino acid motifs. One motif found in all dragline silk repeat units is a block of typically 6-9 alanine residues. In silk threads several polyalanine motifs form crystalline β-sheet stacks leading to tensile strength (5; 6).

Glycine rich motifs such as GGX or GPGXX adopt flexible helical structures that connect crystalline regions and provide elasticity to the thread (7).

Additionally, all investigated dragline silk proteins comprise regions at their carboxyl termini that display no obvious repetition pattern (non-repetitive- or NR-regions). So far no function could be assigned to these regions in the final thread.

Silk assembly in vivo is a remarkable process. Spider dragline silk proteins are stored at concentrations up to 50% (w/v) (8) in the so-called major ampullate gland. Although a "dynamic loose helical structure" has been proposed for the proteins within the major ampullate gland (8) more recent data suggests a random coil conformation for the proteins of the so called A-Zone, which represents the largest part of the gland (9 ;10). The highly concentrated protein solution forms the silk dope (spinning solution), which displays properties of a liquid crystal (11-13).

Thread assembly is initiated during a passage of the dope through the spinning duct accompanied by extraction of water, sodium and chloride (14 ;15). At the same time the concentrations of the more lyotropic ions potassium and phosphate are increased and the pH drops from 6.9 to 6.3 (14-16). Assembly is finally triggered by mechanical stress, which is caused by pulling the thread out of the spider's abdomen (17).

For several purposes natural silk threads can not be used directly, but have to be dissolved and reassembled into other morphologies such as films, foams, spheres, nanofibrils, hydrogels and the like.

Most investigations concerning films made from silk proteins have been performed with silk fibroin, the main protein component of the silk from the silkworm *Bombyx mori*. Silk fibroin films can be cast from aqueous solutions or from solutions containing hexafluoroisopropanol (HFIP), formic acid, and trifluoro acetic acid. In solution silk fibroins tend to adopt helical or random coil conformations, depending on the solvent used. When cast into films, proteins either maintain the conformation of the soluble state or adopt a more β-sheet rich conformation. In most cases processing of the films with methanol leads to a further increase of β-sheet content and crystallinity. Besides silk fibroin, other silk proteins have also been employed to cast films. Vollrath and co-workers investigated films made of proteins extracted from major ampullate gland of the spider *Nephila senegalensis*. As-cast films mainly contained proteins in a random coil conformation when prepared from aqueous solution. Their structure changed into β-sheet upon addition of potassium chloride. Further, films have been made from a synthetic silk protein derived from the dragline silk protein MaSp1 of the spider *Nephila clavipes* using HFIP as solvent. In solution the protein adopted an α-helical structure changing to a more β-sheet rich conformation when cast into a film.

Unfortunately, the generation of functional film materials from natural silk fibroin is restrained by its amino acid sequence. Selective chemical modification of silk fibroin is only possible to a very limited extend due to the low abundance (<1.5%) of chemically reactive amino acid side chains that contain thiol, amino or carboxyl groups. Further, genetic modification within the natural host to alter the silk protein's and thus the film's properties is tedious.

While some structural aspects of spider silk proteins have been unravelled, still little is known about the contribution of individual silk proteins and their primary structure elements to the assembly process. Comparative studies of the two major dragline silk proteins of the garden spider *Araneus diadematus*, ADF-3 and ADF-4, revealed that, although their amino acid sequences are rather similar (4), they display remarkably different solubility and assembly characteristics: While ADF-3 is soluble even at high concentrations (18), ADF-4 is virtually insoluble and self-assembles into filamentous structures under specific conditions (unpublished results).

Scientific and commercial interest initiated the investigation of industrial scale manufacturing of spider silk. Native spider silk production is impractical due to the cannibalism of spiders, and artificial production has encountered problems in achieving both sufficient protein yield and quality threadassembly. Bacterial expression yielded low protein levels, likely caused by a different codon usage in bacteria and in spiders. Synthetic genes with a codon usage adapted to the expression host led to higher yields, but the proteins synthesized thereof showed different characteristics in comparison to native spider silks Expression of partial dragline silk cDNAs in mammalian cell lines did yield silk proteins (e.g.

ADF-3) that could be artificially spun into 'silken' threads, albeit as yet of inferior quality.

WO03060099 relates to methods and devices for spinning biofilament proteins into fibers. This invention is particularly useful for spinning recombinant silk proteins from aqueous solutions and enhancing the strength of the fibers and practicality of manufacture such as to render commercial production and use of such fibers practicable. Therein, it is disclosed to express spider silk proteins in mammalian cells, e.g. transgenic goat mammary gland cells.

Expression of authentic spider silk genes in bacterial hosts is—as mentioned above—inefficient (24) since some gene sections contain codons not efficiently translated in bacteria. In addition, gene manipulation and amplification by PCR is difficult due to the repetitive nature of silks. In order to investigate properties of spider silk proteins, cloning strategies have been employed using synthetic DNA modules with a codon usage adapted to the corresponding expression host. Synthetic genes were obtained which coded for proteins resembling the repetitive regions of spider silks (25-28). However, none of these protein designs included the carboxyl terminal NR-regions that are found in all dragline silks.

Therefore it is an object underlying the present invention to provide recombinant silk spider proteins having enhanced characteristics as, in particular, improved capability of being expressed in high yield and improved strength and flexibility, i.e. better quality. Furthermore, it is an object of the present invention to provide recombinant spider silk proteins, which can be conveniently expressed in already known expression systems. It is a further object of the invention to provide an improved method for the aggregation of spider silk proteins and a method for forming threads made of these proteins. Additionally, it is an object of the present invention to provide improved paper, textile and leather products. Additional objects are to provide new proteins and further materials based on spider silk proteins such as spheres, nanofibrils, hydrogels, threads, foams, films for use in biotechnology, medicine, pharmaceutical and food applications, cosmetics, in electronic devices and for other commercial purposes.

These objects are solved by the subject-matter of the independent claims. Preferred embodiments are set forth in the dependent claims.

The present protein engineering approach, which provides recombinant spider silk proteins, comprising or consisting of synthetic repetitive spider silk protein sequences and/or authentic NR-(non repetitive) regions, reveals that proteins closely resembling authentic silk proteins can be produced at high yields. In particular, the bacterial expression system as well as the simple and cheap purification process provided herein, which can easily be scaled up, provides the basis for cost-efficient industrial scale production of spider silk-like proteins.

Spider silk proteins have mainly been investigated regarding their contribution to mechanical properties of the silk thread. However, little is known about the molecular mechanisms of silk assembly. As a first step towards characterizing this process, the inventors identified primary structure elements of the garden spider's (*Araneus diadematus*) major dragline silk proteins ADF-3 and ADF-4 that determine protein solubility. Further, the influence of conditions involved in mediating natural thread assembly on protein aggregation was investigated. Genes coding for spider silk-like proteins were generated using a newly developed cloning strategy, which is based on a combination of synthetic DNA modules and PCR-amplified authentic gene sequences. Comparing secondary structure, solubility and aggregation properties of the synthesized proteins revealed that single primary structure elements have diverse influences on protein characteristics. Repetitive regions representing the largest part of dragline silk proteins determined the solubility of the synthetic proteins, which differed greatly between constructs derived from ADF-3 and ADF-4. Factors, such as acidification and increase of phosphate concentration, which promote silk assembly in vivo, generally decreased silk protein solubility in vitro. Strikingly this effect was pronounced in engineered proteins comprising the carboxyl terminal non-repetitive regions of ADF-3 or ADF-4, indicating that these regions play an important role in initiating assembly of spider silk proteins.

According to a first aspect, the present invention is directed to a recombinant spider silk protein comprising
  a) one or more synthetic repetitive spider silk protein sequences, and/or
  b) one or more authentic non-repetitive spider silk protein sequences.

The term "synthetic repetitive sequence" as used herein is to be understood as a recombinant protein sequence, which can not be found in nature, which is, however, derived from repeat units, which are naturally occurring in spider silk proteins. As indicated above, those repetitive sequences comprise one or more single repeat units, which comprise up to 60 amino acids. The naturally occurring repeat units comprehend a limited set of distinct amino acid motifs. Those repeat units confer inter alia tensile strength and elasticity to the thread, which may be later on formed from the spider silk protein.

The different types of repeat units, which may be form the base for the synthetic repetitive sequence of the invention, will be explained in detail below.

The second component of the recombinant spider silk protein of the invention, which may be present in addition to the synthetic repetitive sequences or alone, comprises one or more authentic non-repetitive protein sequences. These non-repetitive sequences play an important functional role in thread assembly.

It is noted that in the present invention, also recombinant spider silk proteins are contemplated, which only comprise synthetic repetitive sequences. Although the recombinant proteins of the invention showing both components, i.e. synthetic repetitive sequences as well as authentic non-repetitive sequences, have a broader range of utility and can be yielded in higher amounts (see chapter Examples below), the recombinant spider silk proteins having only synthetic repetitive sequences included can be used for some specific applications.

These applications are—inter alia—automotive and aircraft parts, surface coatings, as well as wound closure systems and wound dressings. Or in other words, applications, in which no thread structures of spider silk proteins are required.

The term "authentic" as used herein means that the underlying nucleic acid sequences are isolated from their natural environment without performing substantial amendments in the sequence itself. The only modification, which is accepted to occur, is where the authentic non-repetitive nucleic acid sequence is modified in order to adapt said sequence to the expression in a host without changing the encoded amino acid sequence. Preferred sequences are NR3 (SEQ ID NO: 10; derived from ADF-3) and NR4 (SEQ ID NO: 11; derived from ADF-4). In both sequences, for more efficient translation, the codon AGA (Arg), which is rarely translated in *E. coli*, was mutated to CGT (Arg) using PCR mutagenesis.

Preferred authentic non-repetitive sequences of flagelliform proteins are the amino acid sequence and nucleic acid sequence of FlagN-NR (SEQ ID NOs: 31 and 32) and FlagC-NR (SEQ ID NOs: 33 and 34).

According to a preferred embodiment, the recombinant spider silk proteins of the invention generally are derived from spider dragline proteins from the spider's major ampullate gland and/or from proteins derived from the flagelliform gland.

According to a further preferred embodiment, the authentic non-repetitive sequences are derived from the amino terminal non-repetitive region (flagelliform proteins) and/or the carboxy terminal non-repetitive region (flagelliform and dragline proteins) of a naturally occurring spider silk protein. Preferred examples of those proteins will be indicated below.

It is generally preferred to select the dragline and/or flagelliform sequences from dragline or flagelliform proteins of orb-web spiders (Araneidae and Araneoids).

More preferably the dragline proteins and/or flagelliform proteins are derived from one or more of the following spiders: *Arachnura higginsi, Araneus circulissparsus, Araneus diadematus, Argiope picta*, Banded Garden Spider (*Argiope trifasciata*), Batik Golden Web Spider (*Nephila antipodiana*), Beccari's Tent Spider (*Cyrtophora beccarii*), Bird-dropping Spider (*Celaenia excavata*), Black-and-White Spiny Spider (*Gasteracantha kuhlii*), Black-and-yellow Garden Spider (*Argiope aurantia*), Bolas Spider (*Ordgarius furcatus*), Bolas Spiders—Magnificent Spider (*Ordgarius magnificus*), Brown Sailor Spider (*Neoscona nautica*), Brown-Legged Spider (*Neoscona rufofemorata*), Capped Black-Headed Spider (*Zygiella calyptrata*), Common Garden Spider (*Parawixia dehaani*), Common Orb Weaver (*Neoscona oxancensis*), Crab-like Spiny Orb Weaver (*Gasteracantha cancriformis* (elipsoides)), Curved Spiny Spider (*Gasteracantha arcuata*), *Cyrtophora moluccensis, Cyrtophora parnasia, Dolophones conifera, Dolophones turrigera*, Doria's Spiny Spider (*Gasteracantha doriae*), Double-Spotted Spiny Spider (*Gasteracantha mammosa*), Double-Tailed Tent Spider (*Cyrtophora exanthematica*), *Aculeperia ceropegia, Eriophora pustulosa*, Flat Anepsion (*Anepsion depressium*), Four-spined Jewel Spider (*Gasteracantha quadrispinosa*), Garden Orb Web Spider (*Eriophora transmarina*), Giant Lichen Orbweaver (*Araneus bicentenarius*), Golden Web Spider (*Nephila maculata*), Hasselt's Spiny Spider (*Gasteracantha hasseltii*), *Tegenaria atrica, Heurodes turrita*, Island Cyclosa Spider (*Cyclosa insulana*), Jewel or Spiny Spider (*Astracantha minax*), Kidney Garden Spider (*Araneus mitificus*), Laglaise's Garden Spider (*Eriovixia laglaisei*), Long-Bellied Cyclosa Spider (*Cyclosa bifida*), Malabar Spider (*Nephilengys malabarensis*), Multi-Coloured St Andrew's Cross Spider (*Argiope versicolor*), Ornamental Tree-Trunk Spider (*Herennia ornatissima*), Oval St. Andrew's Cross Spider (*Argiope aemula*), Red Tent Spider (*Cyrtophora unicolor*), Russian Tent Spider (*Cyrtophora hirta*), Saint Andrew's Cross Spider (*Argiope keyserlingi*), Scarlet Acusilas (*Acusilas coccineus*), Silver Argiope (*Argiope argentata*), Spinybacked Orbweaver (*Gasteracantha cancriformis*), Spotted Orbweaver (*Neoscona domiciliorum*), St. Andrews Cross (*Argiope aetheria*), St. Andrew's Cross Spider (*Argiope Keyserlingi*), Tree-Stump Spider (*Poltys illepidus*), Triangular Spider (*Arkys clavatus*), Triangular Spider (*Arkys lancearius*), Two-spined Spider (*Poecilopachys australasia*), *Nephila* species, e.g. *Nephila clavipes, Nephila senegalensis, Nephila madagascariensis* and many more (for further spider species, see also below). Most preferred, the dragline proteins are derived from *Araneus diadematus* and the flagelliform proteins are derived from *Nephila clavipes*.

In the context of this invention, it should be clear that a recombinant spider silk protein may not only comprise proteinsequences from one species, but may also contain sequences derived from different spider species. As an example, the one or more synthetic repetitive spider silk protein sequences might be derived from one species, the one or more authentic non-repetitive spider silk protein sequences from another. As a further example, it is also possible to design a recombinant spider silk protein, which contains more than one type of a repetitive sequence, wherein the different types are derived from different species.

According to one preferred embodiment, the dragline protein is wild type ADF-3, ADF-4, MaSp I, MaSp II and the flagelliform protein is FLAG. The term ADF-3/-4 is used in the context of MaSp proteins produced by Araneus diadematus (Araneus diadematus fibroin-3/-4). Both proteins, ADF-3 and -4 belong to the class of MaSp II proteins (major ampullate spidroin II).

The silk fiber has crystalline regions of β-sheets interspersed with elastic amorphous segments similar to liquid crystalline polymers. These two segments are represented by two different protein classes, MaSp I (major ampullate spidroin I) and MaSp II (major ampullate spidroin II) coded by different genes.

In a further embodiment, the nucleic acid sequence provided is ADF-3 (SEQ ID NO:1) and/or ADF-4 (SEQ ID NO: 2), or a variant thereof.

It is noted that two different kinds of ADF-3 and ADF-4 coding sequences and proteins are contemplated in this invention: first, the already published sequence of ADF-3 and ADF-4 (herein: "wild type" sequence) and, second, a variant thereof, encoded by SEQ ID NO: 1 (ADF-3) and 2 (ADF-4). The wild type sequences were already published and are available under the accession numbers U47855 and U47856 (SEQ ID NO: 8 and 9).

Further spider silk proteins, which can be used in this invention (i.e. alone or in combination with further proteins) and their database accession numbers are:
spidroin 2 [*Araneus bicentenarius*]gi|2911272
major ampullate gland dragline silk protein-1 [*Araneus ventricosus*]gi|27228957
major ampullate gland dragline silk protein-2 [*Araneus ventricosus*]gi|27228959 ampullate
spidroin 1 [*Nephila madagascariensis*]gi|13562006
major ampullate spidroin 1 [*Nephila senegalensis*] gi|13562010
major ampullate spidroin 1 [*Latrodectus geometricus*] gi|13561998
major ampullate spidroin 1 [*Argiope trifasciata*]gi|13561984
major ampullate spidroin 1 [*Argiope aurantia*]gi|13561976
dragline silk protein spidroin 2 [*Nephila clavata*] gi|16974791
major ampullate spidroin 2 [*Nephila senegalensis*] gi|13562012
major ampullate spidroin 2 [*Nephila madagascariensis*] gi|13562008
major ampullate spidroin 2 [*Latrodectus geometricus*] gi|13562002

According to another preferred embodiment, the flagelliform protein is SEQ ID NO: 6 (Flag-N) and/or SEQ ID NO: 7 (Flag-C) or a variant thereof, which constitute novel sequences derived by the inventors.

However, also already known and published flagelliform sequences may be used herein, in particular the following:
Flagelliform silk protein partial cds [*Nephila clavipes*] gi|2833646
Flagelliform silk protein partial cds [*Nephila clavipes*] gi|2833648

In one preferred embodiment, the recombinant spider silk protein comprises one or more synthetic repetitive sequences containing one or more polyalanine containing consensus sequences. Those polyalanine sequences may contain from 6 to 9 alanine residues. See, for example SEQ ID NO: 1, containing several polyalanine motifs of 6 alanine residues.

Preferably, the polyalanine containing consensus sequence is derived from ADF-3 and has the amino acid sequence of SEQ ID NO: 3 (module A) or a variant thereof. Module A contains a polyalanine having 6 alanine residues. A further preferred polyalanine containing consensus sequence, derived from ADF-4, is module C (SEQ ID NO: 5), containing 8 alanine residues.

According to a further preferred embodiment, in the recombinant spider silk protein of the invention, the synthetic repetitive sequence is derived from ADF-3 and comprises one or more repeats of the amino acid sequence of SEQ ID NO: 4 (module Q) or a variant thereof.

In more general words, a synthetic repetitive sequence may also contain the general motifs: GGX or GPGXX, i.e. glycine rich regions. As mentioned above, these regions will provide flexibility to the protein and thus, to the thread formed from the recombinant spider silk protein containing said motifs.

It is noted that the specific modules for the synthetic repetitive sequence of the invention can also be combined with each other, i.e. modules (repeat units) combining A and Q, Q and C etc. are also encompassed by the present invention. Although the number of the modules to be introduced in the spider silk protein is not restricted, it is preferred to employ a number of modules of the synthetic repetitive sequence for each recombinant protein which number is preferably ranging from 5-50 modules, more preferably 10-40 and most preferably between 15-35 modules.

The synthetic repetitive sequence preferably comprises one or more of (AQ) and/or (QAQ) as repeat units. Even more preferred, the synthetic repetitive sequence is $(AQ)_{12}$, $(AQ)_{24}$, $(QAQ)_8$ or $(QAQ)_{16}$.

Whenever the synthetic repetitive sequence is derived from ADF-4, it may preferably comprise one or more repeats of the amino acid sequence of SEQ ID NO: 5 (module C) or a variant thereof, as mentioned above, wherein the overall synthetic repetitive sequence is $C_{16}$ or $C_{32}$.

Preferred embodiments for the complete recombinant spider silk proteins of the invention are $(QAQ)_8NR3$, $(QAQ)_{16}NR3$, $(AQ)_{12}NR3$, $(AQ)_{24}NR3$, $C_{16}NR4$ and $C_{32}NR4$ i.e. proteins which comprise or consist of said sequences.

It is noted that the above configuration of the synthethic repetitive sequence (using the A, Q and C system) also applies to all other repeat units disclosed above, for example all polyalanine containing sequences can be taken for A and/or C and all glycine rich sequences may be used as Q.

New modules for synthetic repetitive sequences derived from flagelliform sequences are modules K (SEQ ID NO: 35 and 36), sp (SEQ ID NO: 37 and 38), X (SEQ ID NO: 39 and 40), and Y (SEQ ID NO: 41 and 42):

The synthetic repetitive sequence also preferably comprises or consists of $Y_8$, $Y_{16}$, $X_8$, $X_{16}$, $K_8$, $K_{16}$.

Furthermore, it is also possible, to combine those sequences derived from ADF-3 and ADF-4 and Flag in one recombinant sequence.

As explained above, the amino acid sequences disclosed herein are not restricted to the exact sequences provided in the SEQ ID Nos. The amino acid sequences indicated herein also comprise variants. Thus, the amino acid sequences of the proteins of the present invention also encompass all sequences differing from the herein disclosed sequences by amino acid insertions, deletions, and substitutions.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1 to 5 amino acids, preferably about 1, 2 or 3 amino acids. Amino acid additions typically are not more than 100, preferably not more than 80, more preferably not more than 50, most preferred not more than 20 amino acids, which are added on and/or inserted into the proteins of the present invention. It is noted that only those additions are contemplated in this invention, which do not negatively affect the desired characteristics of the proteins disclosed herein.

The variation allowed may be experimentally determined by systematically making insertions, deletions, or substitutions of amino acids in a protein using recombinant DNA techniques and assaying the resulting recombinant variants for activity. This does not require more than routine experiments for the skilled artisan.

The present invention is, according to a second aspect, directed to a nucleic acid sequence, coding for a recombinant spider silk protein as disclosed above. Preferred sequences coding for preferred proteins are SEQ ID NO: 12 (ADF-3), 13 (ADF-4), 14 (NR3), 15 (NR4), 16 (FLAG-NT), 17 (FLAG-CT), 32 (FlagN-NR), 34 (FlagC-NR).

The invention also encompasses variants of those nucleic acids. These variants are each defined as having one or more substitutions, insertions and/or deletions as compared to the sequences of SEQ ID NO: 12-17, 32 and 34, provided that said variants hybridize under moderately stringent conditions to a nucleic acid which comprises the sequence of SEQ ID NO: 12-17, 32 and 34, or provided that said variants comprise nucleic acid changes due to the degeneracy of the genetic code, which code for the same or a functionally equivalent amino acid as the nucleic acid sequence of SEQ ID NO: 12-17, 32 and 34.

The term "nucleic acid sequence" refers to a heteropolymer of nucleotides or the sequence of these nucleotides. The terms "nucleic acid" and "polynucleotide" are used interchangeably herein to refer to a heteropolymer of nucleotides.

Stringency of hybridization, as used herein, refers to conditions under which polynucleotide duplexes are stable. As known to those of skill in the art, the stability of duplex is a function of sodium ion concentration and temperature (see, for example, Sambrook et al., Molecular Cloning: A Laboratory Manual $2^{nd}$ Ed. (Cold Spring Harbor Laboratory, (1989)). Stringency levels used to hybridize can be readily varied by those of skill in the art.

As used herein, the phrase "moderately stringent conditions" refers to conditions that permit DNA to bind a complementary nucleic acid that has about 60% identity, preferably about 75% identity, more preferably about 85% identity to the DNA; with greater than about 90% identity to said DNA being especially preferred. Preferably, moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C.

According to a third aspect, a vector is provided which comprises the above mentioned nucleic acids. Preferably, an expression vector is provided, which comprises said nucleic acids. This expression vector preferably comprises one or more regulatory sequences. The term "expression vector" generally refers to a plasmid or phage or virus or vector, for expressing a polypeptide/protein from a DNA (RNA) sequence. An expression vector can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an amino-terminal methionine residue. This residue may or may not be subsequently cleaved from the expressed recombinant protein to provide a final product.

According to a preferred embodiment, the vector is a plasmid or a viral vector, which preferably is a baculovirus system or a vaccinia virus vector system. Further viral vector systems may also be used in this invention. From case to case, a modification of the vector may be needed.

Examples for further viral vectors are adenoviruses and all negative-strand RNA-viruses, e.g. rabies, measles, RSV, etc.

Figure 6:
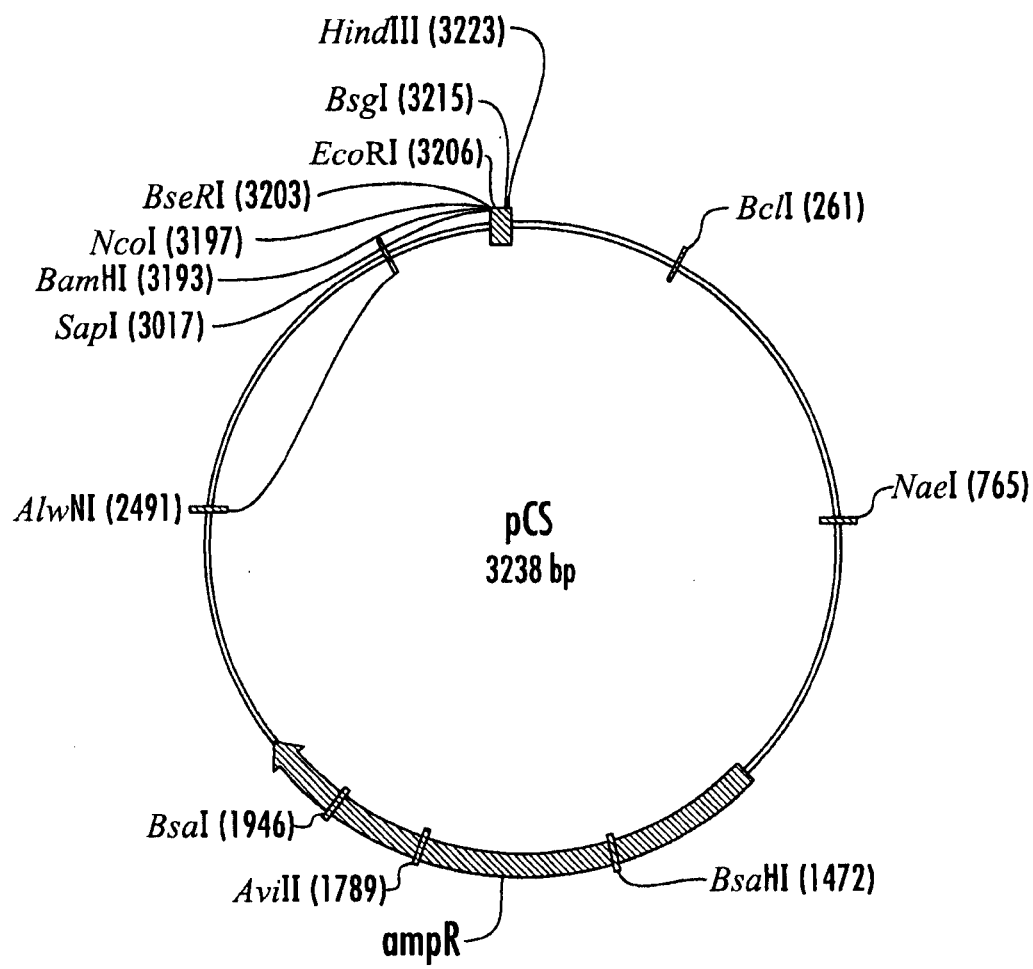

According to a preferred embodiment, the vector is the cloning vector pAZL as defined in FIG. 6 or in SEQ ID NO: 55, or a variant thereof as defined above. This vector is showing the following properties and advantages:
1. high amplification (higher than other cloning vectors)
2. allows controlled and seamless construction of synthetic genes (no other vector is known that provides this ability).

A fourth aspect of the invention comprises a host, which has been transformed with the vector as defined above.

The host may be a prokaryotic cell. In this case, *E. coli* or *Bacillus subtilis* are preferred.

Furthermore, the host may be a eukaryotic cell, preferably a mammalian cell, plant cell, yeast cell or an insect cell.

The mammalian cell preferably is a CHO, COS, HeLa, 293T, HEH or BHK cell.

It is also preferred to use a yeast cell as a host cell, which preferably is *Saccharomyces cerevisiae, Schizosaccharomyces pombe, Pichia pastoris, Candida albicans* or *Hansenula polymorpha*.

As insect cells *Lepidoptera* insect cells may preferably be used, more preferably cells from *Spodoptera frugiperda* and from *Trichoplusia ni*. Most preferably, the insect cell is a Sf9, Sf21 or high five cell.

One advantage of insect cell expression system, for example regarding bacterial systems, resides in the fact that the proteins produced are glycosylated, thereby being a target for degradation by microorganisms. This characteristic may be of importance, for example, in the field of medicine, whenever the silk proteins are intended for an in vivo use, in which biological degradation is desired. This characteristic may in particular find application in suture materials and wound closure and coverage systems.

Whenever the host is a plant cell, the plant cell preferably is derived from tobacco, potato, corn and tomato.

According to a fifth aspect, a method of aggregation of spider silk proteins is provided, comprising the following steps:
a) preparing a protein solution containing unoriented spider silk proteins as defined herein;
b) exposing the solution prepared in a) to an aggregation trigger; and
c) recovering the precipitated spider silk proteins.

Preferably, the spider silk proteins used in step a) are produced by transforming a suitable host as defined above with a vector or a nucleic acid disclosed herein, and expressing the spider silk gene under suitable conditions.

The aggregation trigger is preferably selected from acidification, preferably to a pH of about 1, potassium phosphate and mechanical stress, preferably rotating the protein solution and applying shearing forces. The triggering step turned out to be essential for performing the method of this invention.

It was surprisingly shown by the inventors that in particular the above mentioned trigger factors enhanced the aggregation of spider silk proteins, which is a highly wanted result in particular from an industrial point of view. Reference in this connection is made to the chapter "Results" below, in which the influence of these trigger factors on the recombinant spider silk proteins of the invention is explained: the influence of each trigger factor may vary between the different recombinant spider silk proteins of this invention, however, it can be seen as a general concept that those trigger factors in vitro show an unexpectedly high influence on all recombinant proteins, which comprise the components of the present invention, i.e. repetitive and/or non-repetitive regions. Furthermore, it can be derived from the results provided herein that not a single trigger factor, but also combinations of those may lead to the best way of aggregate spider silk proteins of the invention.

However, it should be noted that this method is not restricted to the spider silk proteins of the present invention, but can also be applied to all other spider silk proteins available, whether naturally occurring or synthetic.

The method further preferably comprises the step of spinning said proteins prepared in step a) or recovered in c) into filaments, nanofibers and threads by a suitable method.

For this purpose, spinning methods may be used, which are per se known in the art. For example, a dope solution of spider silk protein is extruded through a spinneret to form a biofilament. The resulting biofilament can be drawn or stretched. Whenever both crystalline and amorphous arrangements of molecules exist in biofilaments, drawing or stretching will apply shear stress sufficient to orient the molecules to make them more parallel to the walls of the filament and increase the tensile strength and toughness of the biofilament.

The dope solution may contain the recombinant silk proteins of the invention and/or authentic silk proteins from one or more spider species, or silk proteins from different silk-producing genera, for example, a mixture of silk proteins from spiders and *B. mori*. In the most preferred embodiments, the silk proteins are dragline and/or flagelliform silks from *N. clavipes* or *A. diadematus*, particularly the proteins MaSpI, MaSpII, ADF-3, ADF-4 and Flag. In alternate embodiments, the dope solution contains a mixture of silk proteins and one or more synthetic polymers or natural or synthetic biofilament proteins.

Preferably, the dope solution is at least 1%, 5%, 10%, 15% weight/volume (w/v) silk protein. More preferably, the dope solution is as much as 20%, 25%, 30%, 35%, 40%, 45%, or 50% w/v silk protein. In preferred embodiments, the dope solution contains substantially pure spider silk protein. In preferred embodiments, the dope has a pH of approximately 6.9.

By "dope solution" is meant any liquid mixture that contains silk protein and is amenable to extrusion for the formation of a biofilament or film casting. Dope solutions may also contain, in addition to protein monomers, higher order aggregates including, for example, dimers, trimers, and tetramers. Normally, dope solutions are aqueous solutions of pH 4.0-12.0 and having less than 40% organics or chaotropic agents (w/v). Preferably, the dope solutions do not contain any organic solvents or chaotropic agents, yet may include additives to enhance preservation, stability, or workability of the solution.

By "filament" is meant a fiber of indefinite length, ranging from nanoscale and microscopic length to lengths of a mile or greater. Silk is a natural filament, while nylon and polyester as an example are synthetic filaments.

Further information regarding how to spin spider silk protein fibers may be found in WO03060099 (Karatzas et al.), published Jul. 24, 2003, which is incorporated herein by reference.

Furthermore, the spider silk proteins of the present invention may be provided as films or the like, i.e. as a spider silk protein product, for which a spinning step is not required.

For a more detailed description of the process of making films it is referred to chapter Examples.

Additionally, the method of the present invention may preferably include in step a) and/or c) a purification method, comprising exposing the expressed spider silk proteins to heat denaturation at 60-90, preferably 70-80° C. followed by addition of ammonium sulphate of 600-1400 mM, preferably 800-1200 mM.

As already explained above, the proteins/threads as defined herein may be used in the field of biotechnology and/or medicine, preferably for the manufacture of wound closure or coverage systems, suture materials for use in neurosurgery or ophthalmic surgery.

Furthermore, the proteins/threads may preferably be used for the manufacture of replacement materials, preferably artificial cartilage or tendon materials.

Additionally, the threads/fibers of the invention can be used in the manufacture of medical devices such as medical adhesive strips, skin grafts, replacement ligaments, and surgical mesh; and in a wide range of industrial and commercial products, such as clothing fabric, bullet-proof vest lining, container fabric, bag or purse straps, cable, rope, adhesive binding material, non-adhesive binding material, strapping material, automotive covers and parts, aircraft construction material, weatherproofing material, flexible partition material, sports equipment; and, in fact, in nearly any use of fiber or fabric for which high tensile strength and elasticity are desired characteristics. Adaptability and use of the stable fiber product in other forms, such as a dry spray coating, bead-like particles, or use in a mixture with other compositions is also contemplated by the present invention.

It is explicitly noted that the most preferred applications of the spider silk proteins of the present invention are in the manufacture and processing of clothing fabric (textiles) and leather, automotive covers and parts, aircraft construction materials as well as in the manufacture and processing of paper.

The recombinant spider silk proteins of the present invention may be added to cellulose and keratin and collagen products and thus, the present invention is also directed to a paper or a skin care and hair care product, comprising cellulose and/or keratin and/or collagen and the spider silk proteins of the present invention. Papers and skin care and hair care products, in which the proteins of the present invention are incorporated are showing improved characteristics, in particular improved tensile strength or tear strength.

Furthermore, the recombinant spider silk proteins of the invention may be used as a coating for textile and leather products, thereby conferring stability and durability to the coated product. The silk proteins in particular show applicability for coating leather products, since in this case, tanning and its negative effectes for environment can be avoided or at least reduced.

Unless otherwise defined, all technical and scientific terms used herein have the same meaning as commonly understood by one of ordinary skill in the art to which this invention pertains. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention is now further illustrated by Examples and the accompanying drawings, which are showing the following:

FIG. 1 Cloning strategy for constructing synthetic spider silk genes. (A) The cloning cassette comprised restriction sites required for module multimerization (BsgI and BseRI) and for excising assembled genes (NcoI, BamHI, HindIII). During gene construction the spacer region was replaced by modules and module multimers. (B) Site-directed connecting of two modules was accomplished by ligating two appropriate plasmid fragments. The vector's ampicillin resistance gene ($Ap^r$) was reconstituted. (C) Nucleotides required for linking two modules were confined within the first codon of each module. (D) Module multimers were connected like single modules resulting in controlled assembly of synthetic genes. (E) Amino acid sequences of designed silk modules were derived from dragline silk proteins ADF-3 and ADF-4.

Figure 2:
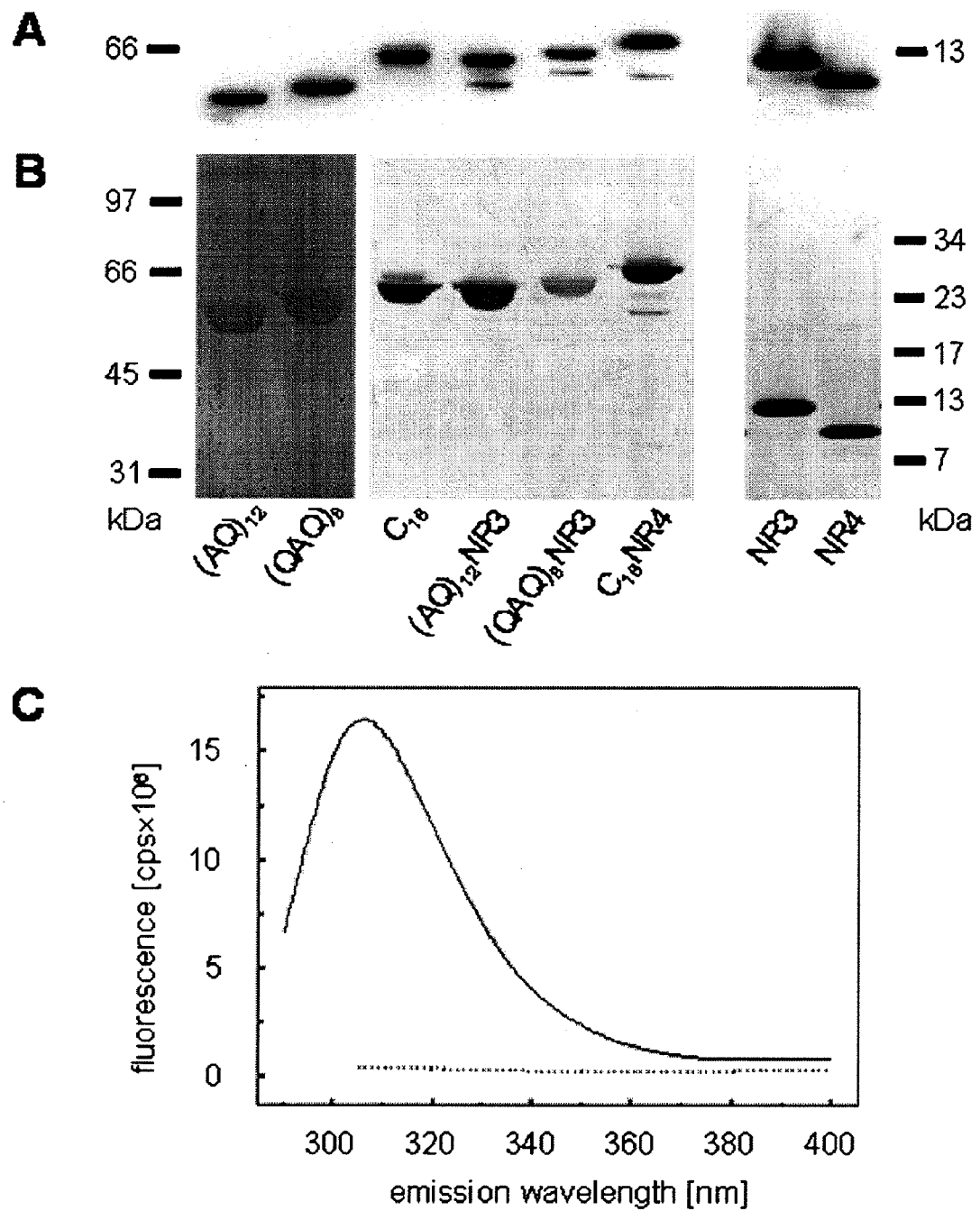

FIG. 2 Analysis of spider silk proteins. (A) T7-tags of recombinant silk proteins were detected after western blotting with an anti-T7-tag antibody. (B) Proteins were subjected to SDS-PAGE followed by silver staining. Due to weak staining of $(AQ)_{12}$ and $(QAQ)_8$ the contrast of the image was increased electronically. (C) Fluorescence emission spectra of purified $C_{16}NR4$ are shown with excitation wavelengths of 280 nm (straight line) or 295 nm (dotted line), respectively.

Figure 3:
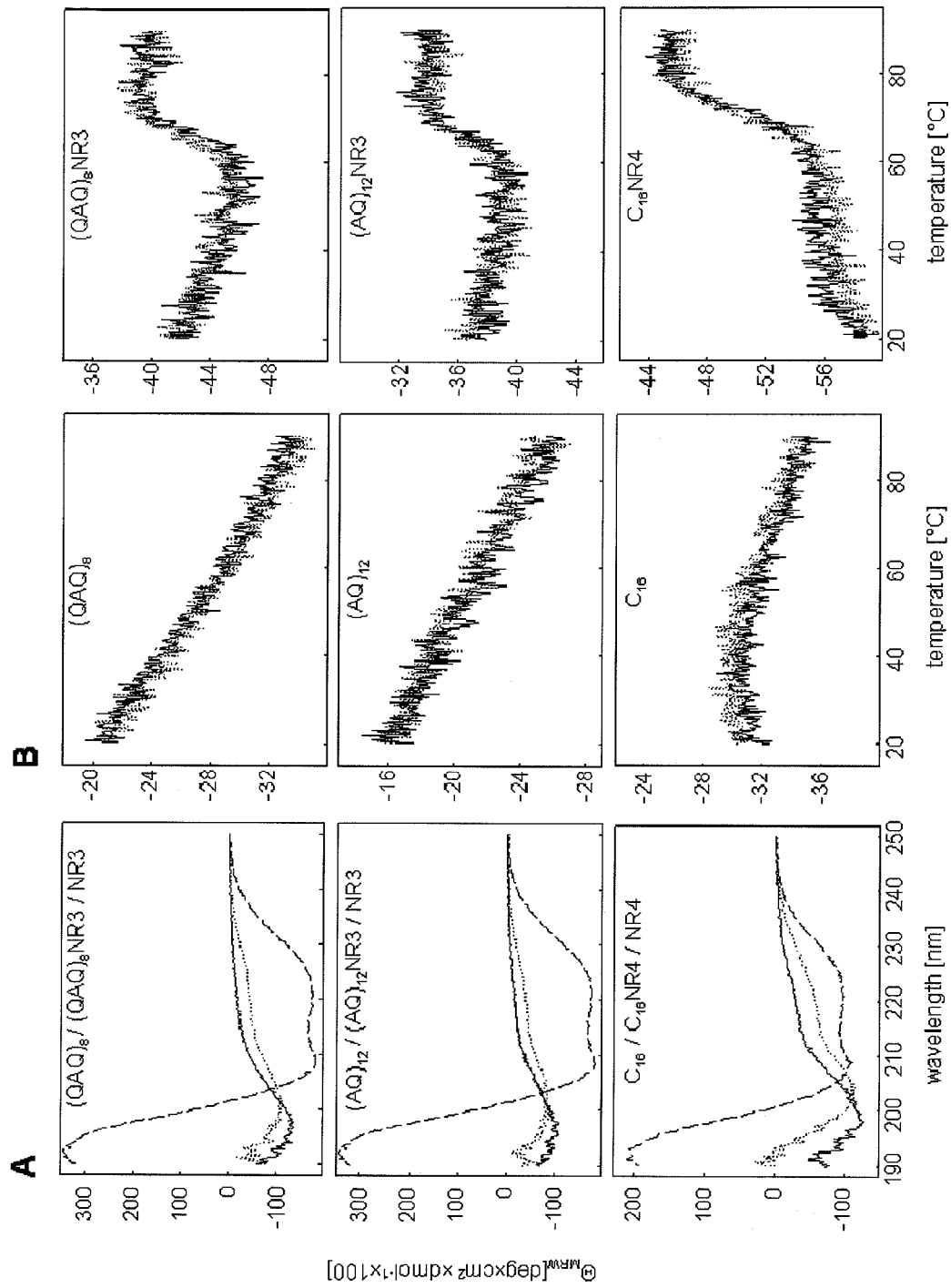

FIG. 3 Secondary structure and temperature transitions of spider silk proteins. (A) CD-spectra of rep-proteins (straight lines), repNR-proteins (dotted lines) and NR-proteins (long dashes) were recorded at 20° C. (B) Mean residue weight (MRW) ellipticities of soluble spider silk proteins were measured at 220 nm while heating synthetic silk proteins to 90° C. (straight line), followed by cooling to 20° C. (dotted line).

Figure 4:
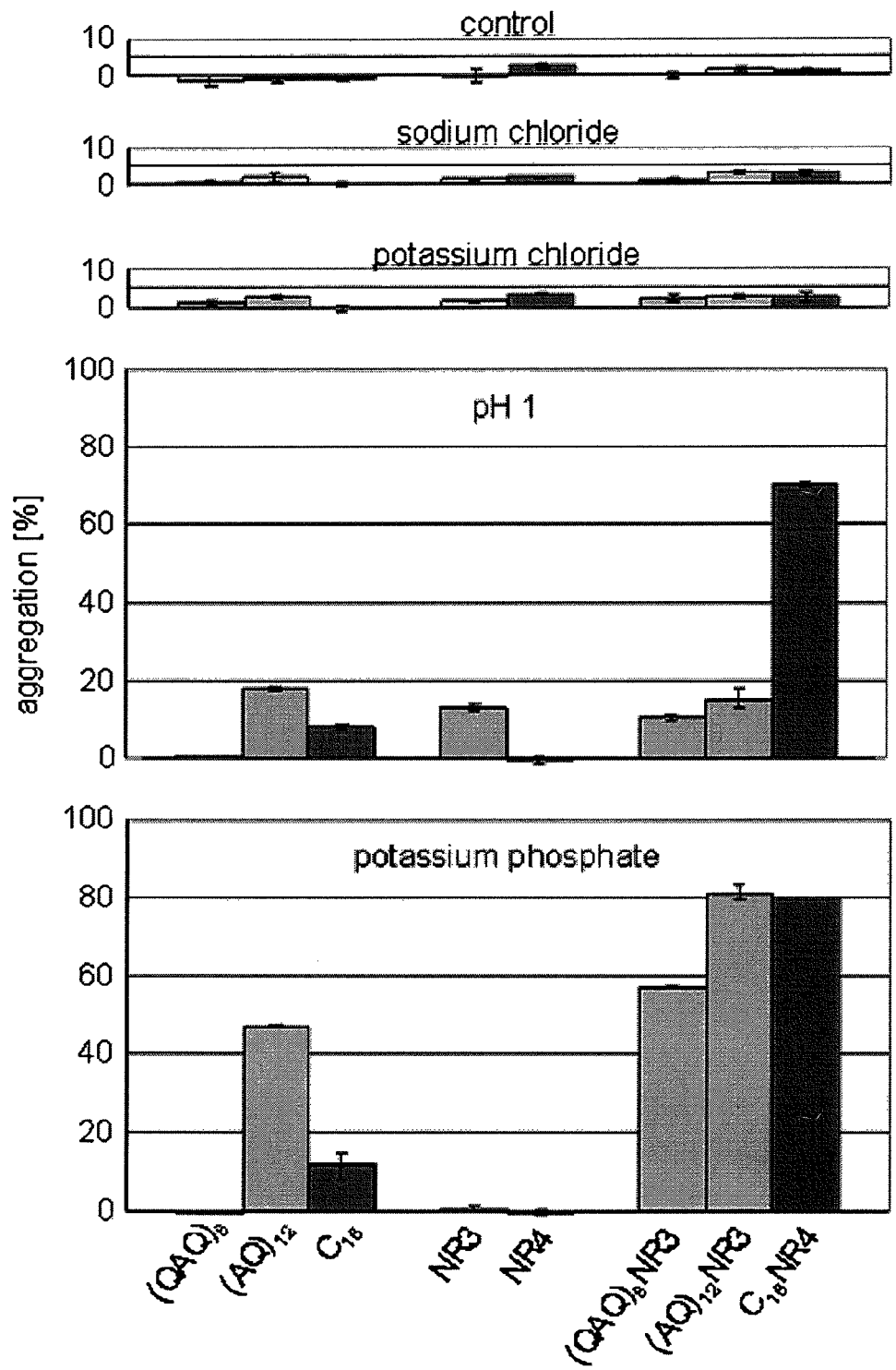

FIG. 4 Aggregation of synthetic spider silk proteins. Aggregation of proteins was determined after incubation for 1 hour in buffer (control), in the presence of 300 mM NaCl, or 300 mM KCl, at pH 1 or in the presence of 300 mM potassium phosphate. Bars for proteins derived from ADF-3: light grey; from ADF-4: dark grey.

Figure 5:
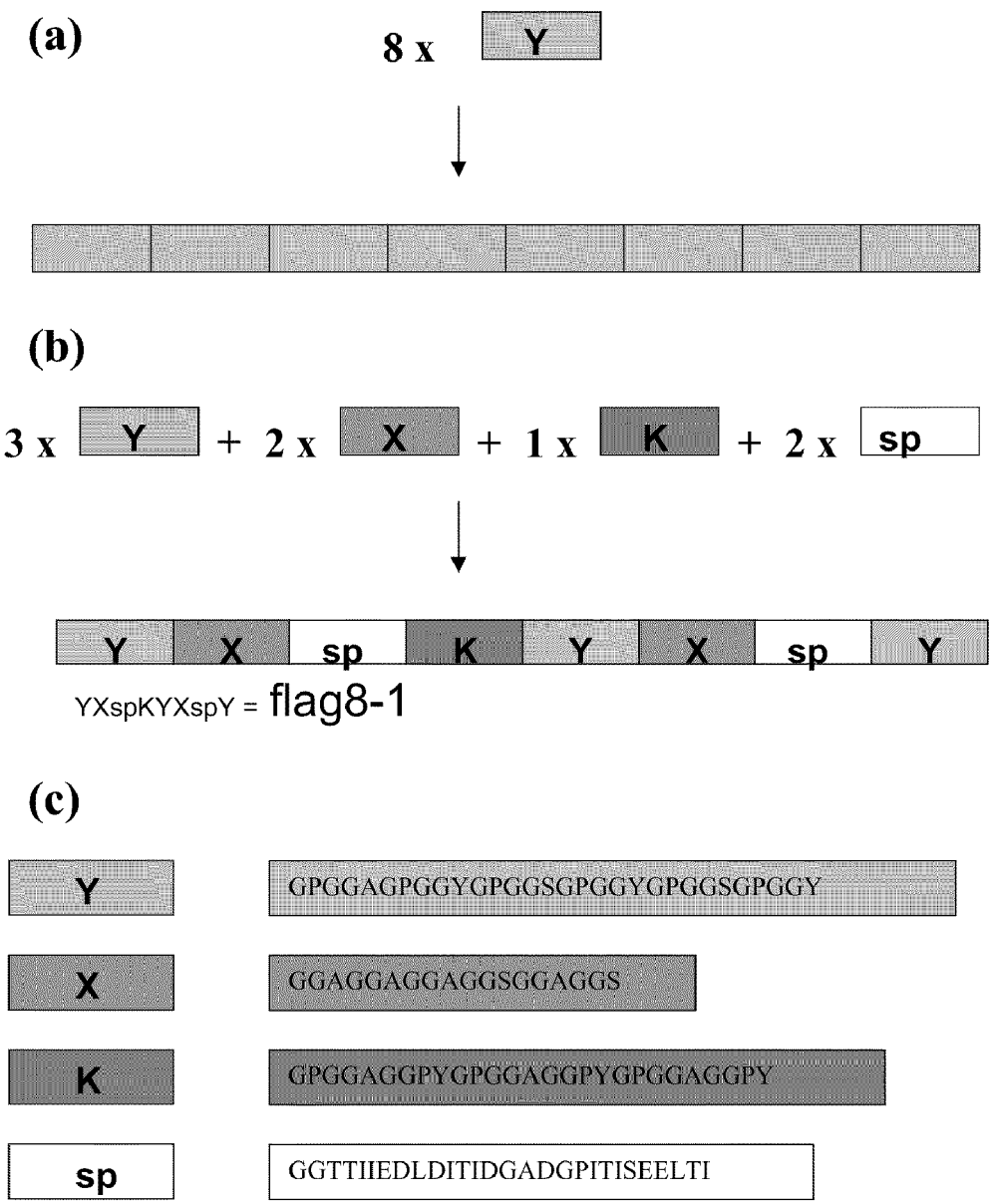

FIG. 5 Cloning strategy for constructing synthetic flagelliform spider silk genes (see FIG. 1). Single modules were connected to homo-multimeres (a) as well as hetero-multimeres (b). (c) shows the amino acid sequences of designed flagelliform silk modules derived from flagelliform silk protein (Flag) from *Nephila clavipes*.

FIG. 6 is showing a restriction map of vector pAZL.

Figure 7:
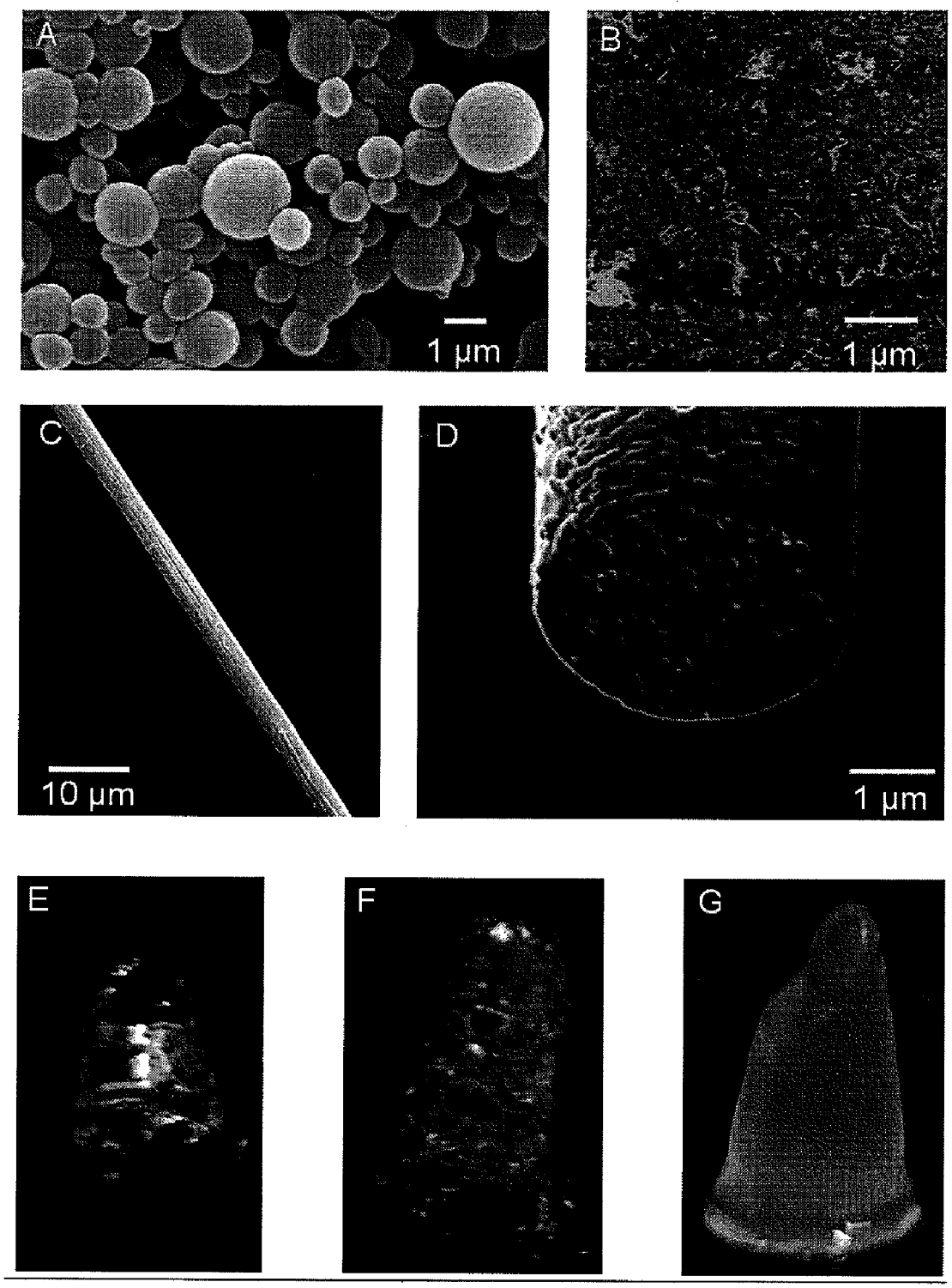

FIG. 7: Assembly forms of spider silk proteins. (A) Spheres formed by $C_{16}$ visualized by scanning electron microscopy (SEM). (B) Nanofibrils formed by $C_{16}NR4$ visualized by atomic force microscopy (height information). (C, D) Microfibril formed by $(AQ)_{24}NR3$ investigated by SEM (C). For cutting the fibril and subsequent visualization of the cross section a focused $Ga^+$ ion beam was used (D). (E) Foam generated from a (AQ)$_{24}$NR3 solution. (F) Foam generated from a C$_{16}$NR4 solution. (G) Crosslinked gel formed by C$_{16}$NR4 nanofibrils.

Figure 8:
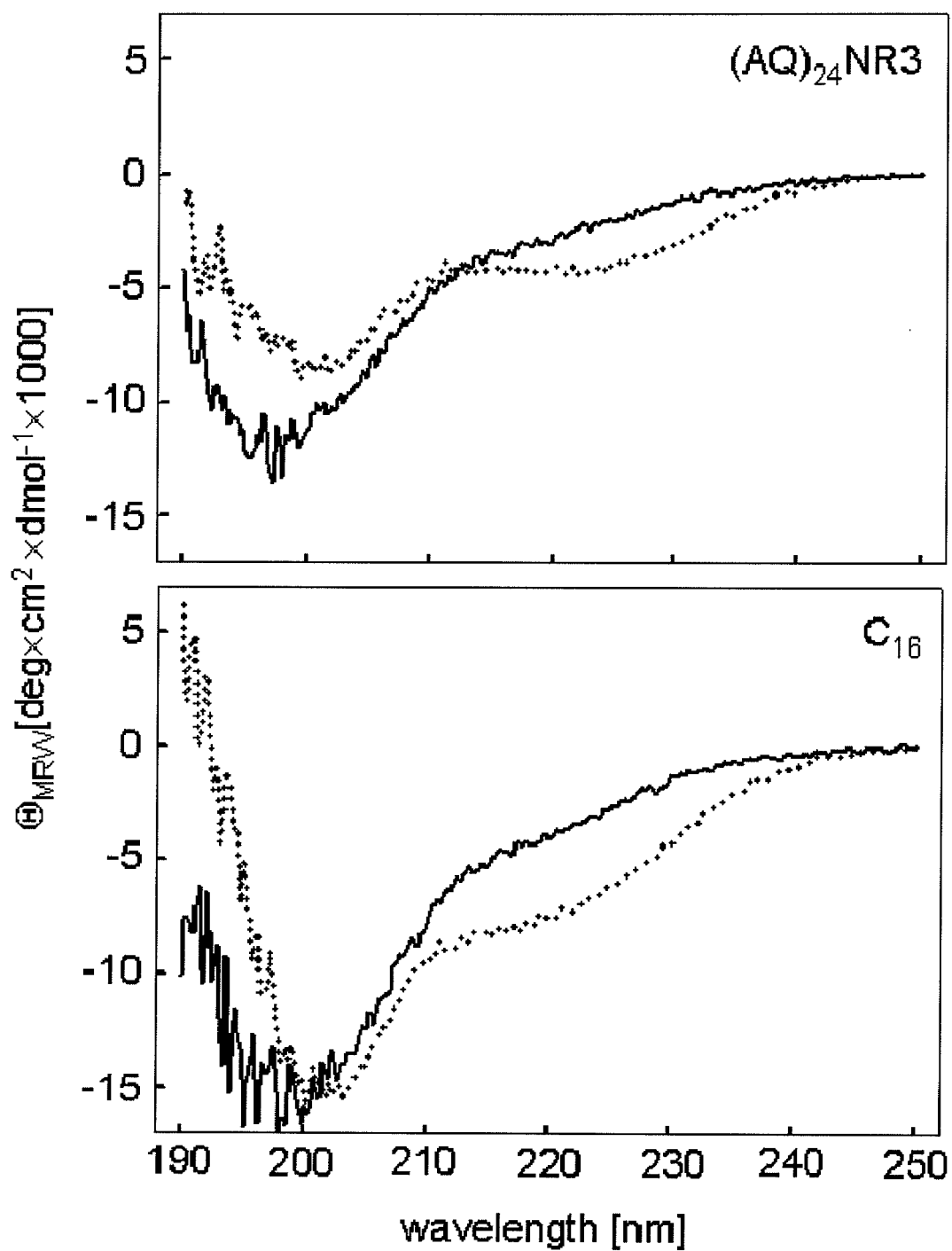

FIG. 8: CD-spectra of synthetic silk proteins (AQ)$_{24}$NR3 and C$_{16}$ dissolved in 6 M guanidinium thiocyanate followed by dialysis against 5 mM potassium phosphate pH 8.0 (straight line) or dissolved in HFIP (dotted line).

Figure 9:
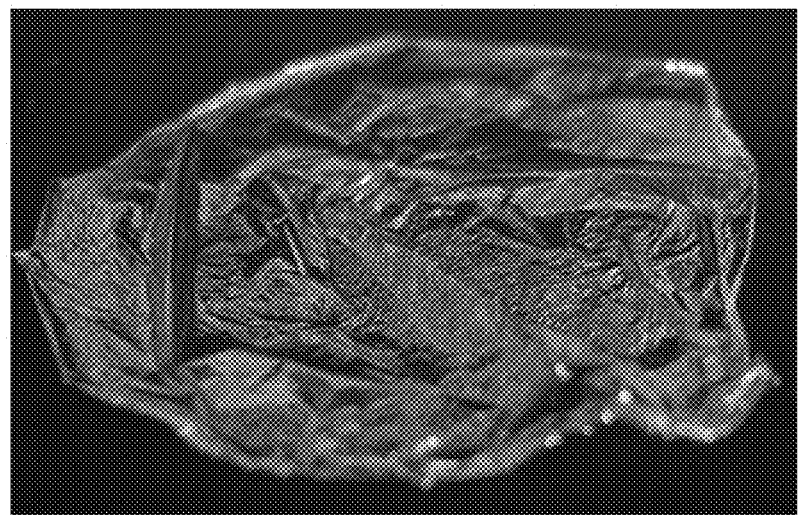

FIG. 9: C$_{16}$ film cast from a 2% w/v C$_{16}$ solution in HFIP.

Figure 10:
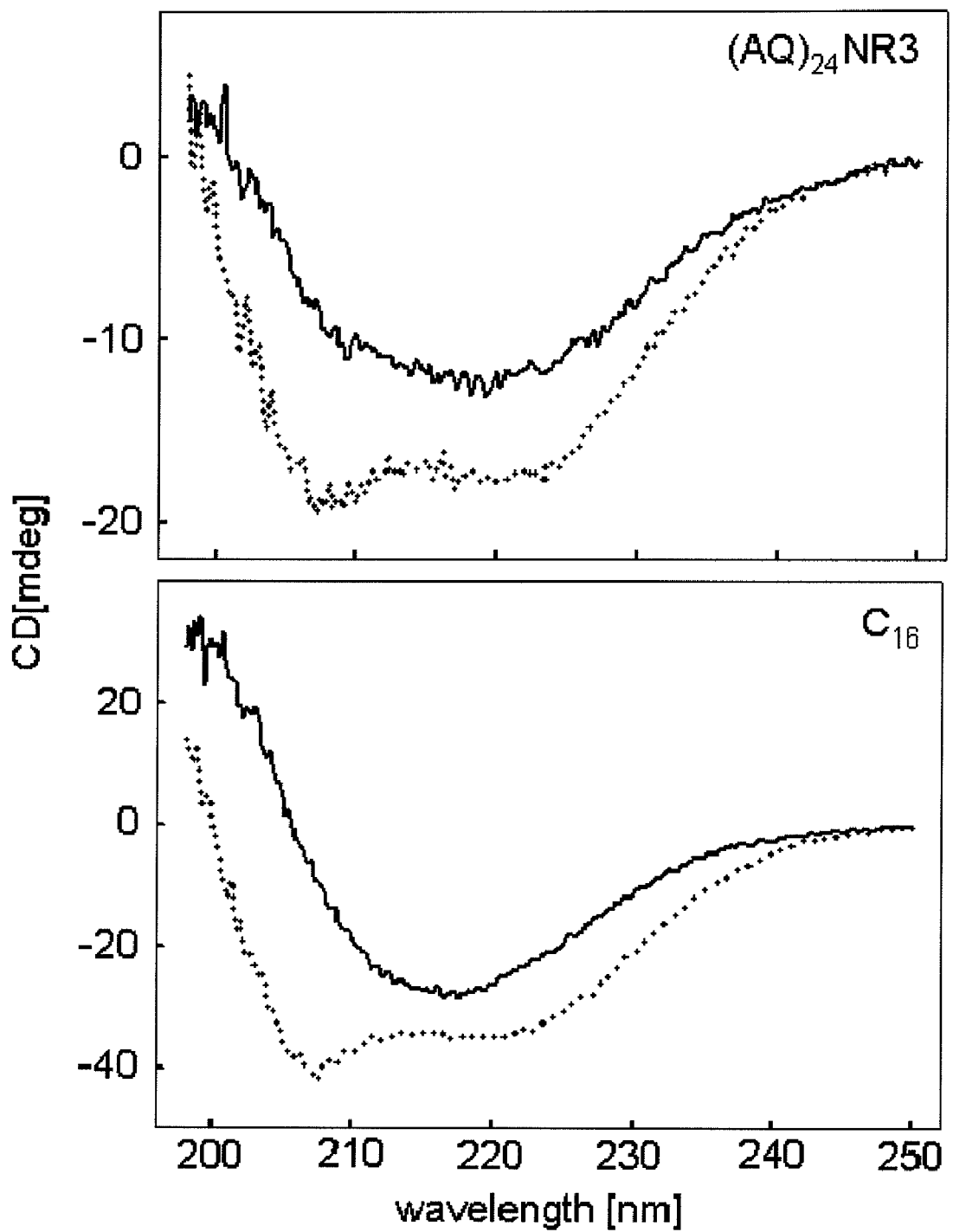

FIG. 10: CD-spectra of protein films made from (AQ)$_{24}$NR3 and C$_{16}$. Films were cast from a protein solution in HFIP directly on a plain quartz glass and analyzed by CD-spectroscopy (dotted line). The film was subsequently processed with 1 M potassium phosphate and re-analyzed. Due to inaccuracies in defining the thickness of the films, MRW could not be determined.

Figure 11:
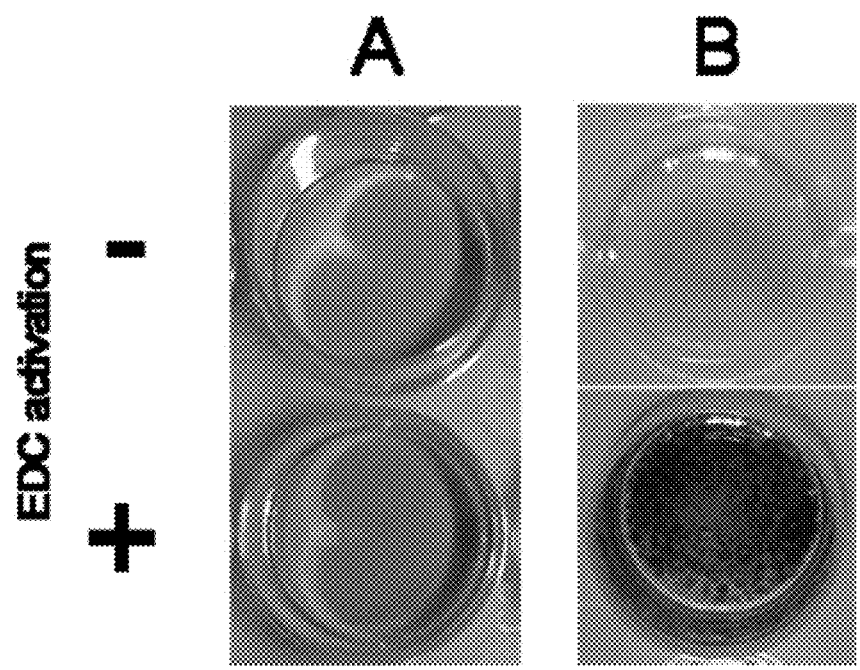

FIG. 11: Modification of C$_{16}$ films cast from a HFIP solution and processed with potassium phosphate. (A) Efficient coupling of fluorescein (yellow colour) only occurred when the carboxyl groups of C$_{16}$ were activated (+) using EDC. In contrast only little fluorescein bound to films without EDC activation (−). (B) Activity of coupled β-galactosidase was monitored using X-Gal as substrate. The occurrence of a blue precipitate indicated enzyme activity only on films that had been activated with EDC (+), while non-activated films only showed residual enzymatic activity (−).

Figure 12:
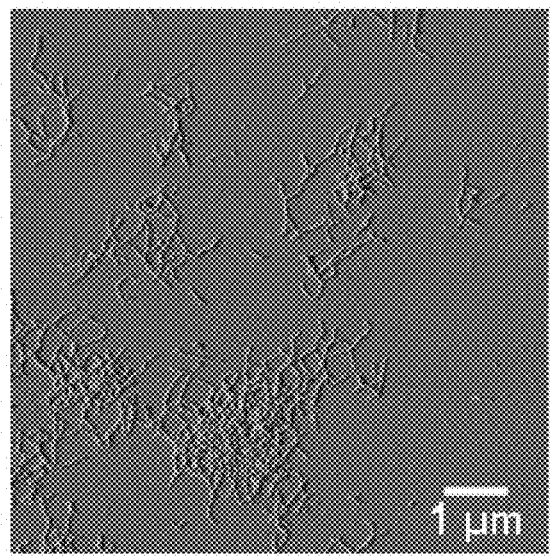

FIG. 12: AFM image of C$_{16}$ nanofibers.

Figure 13:
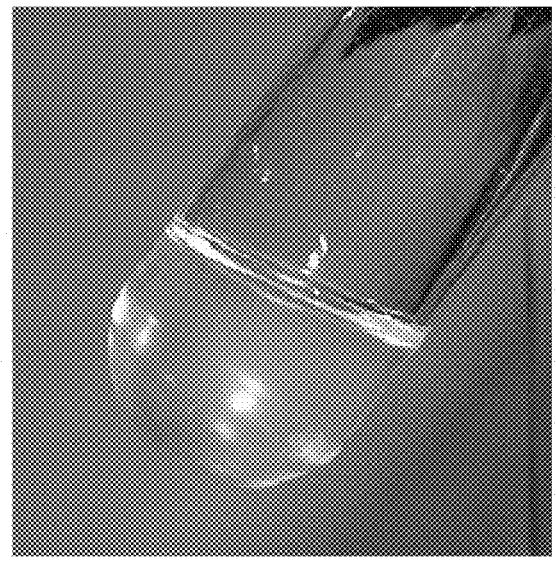

FIG. 13: Hydrogels prepared of C$_{16}$ nanofibers.

Figure 14:
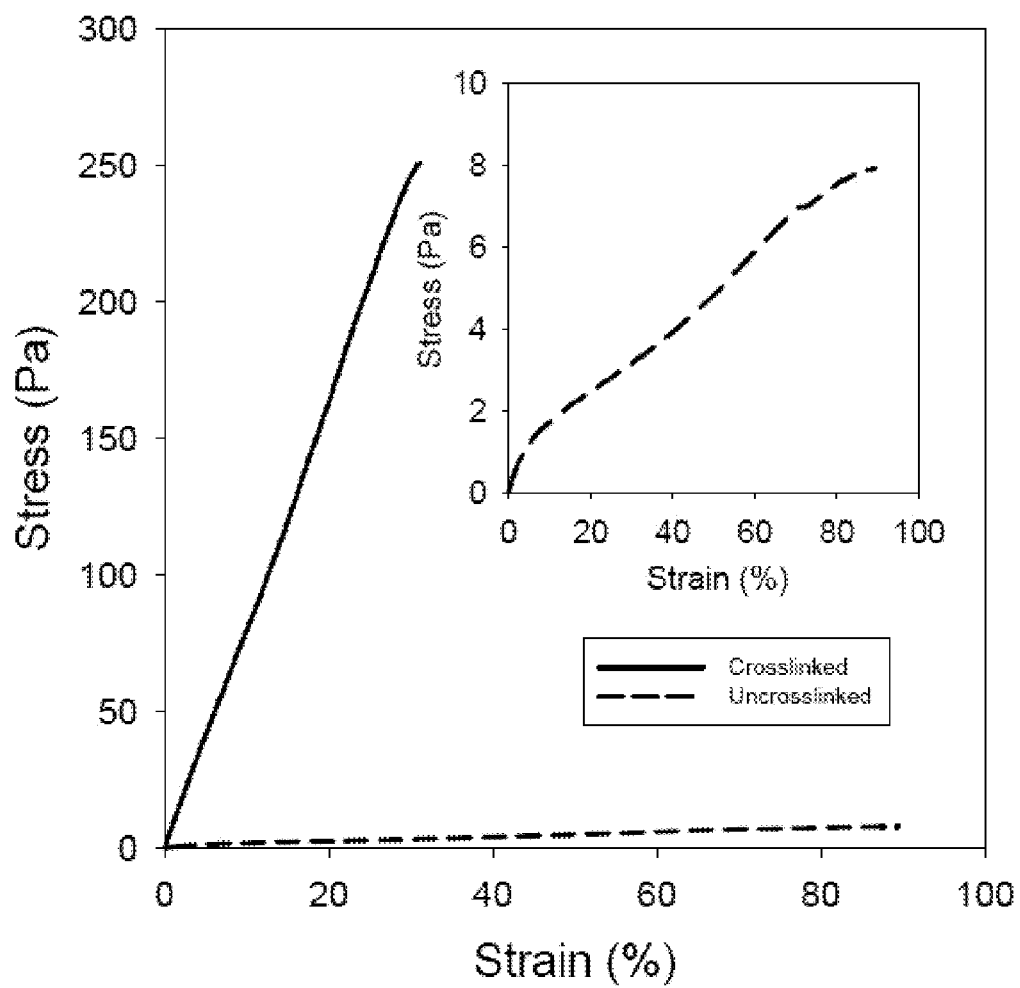

FIG. 14: The stress/strain behavior of the crosslinked and non-crosslinked hydrogels at a concentration of 10 mg/ml.

Figure 15:
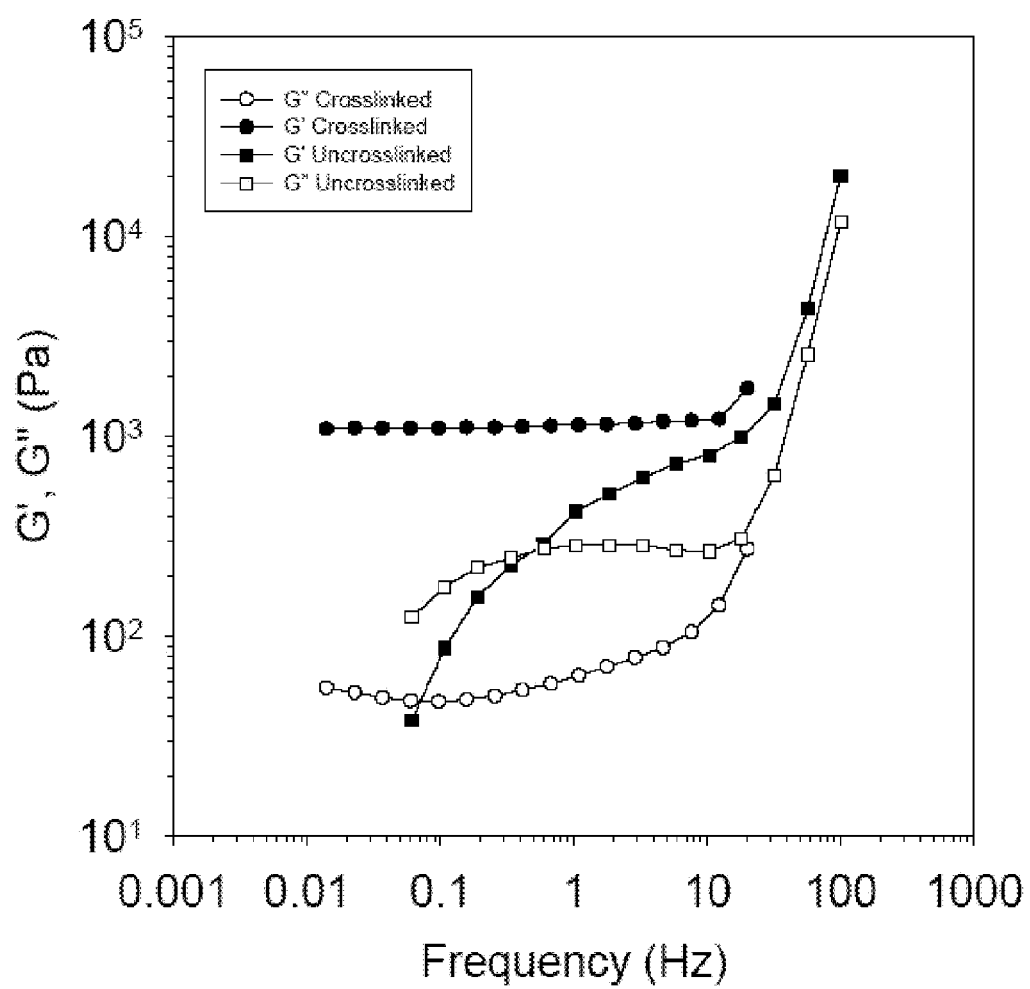

FIG. 15: Frequency dependence of the storage modulus (G') and loss modulus (G") for both the crosslinked and non-crosslinked fiber networks at a concentration of 20 mg/ml.

Figure 16:
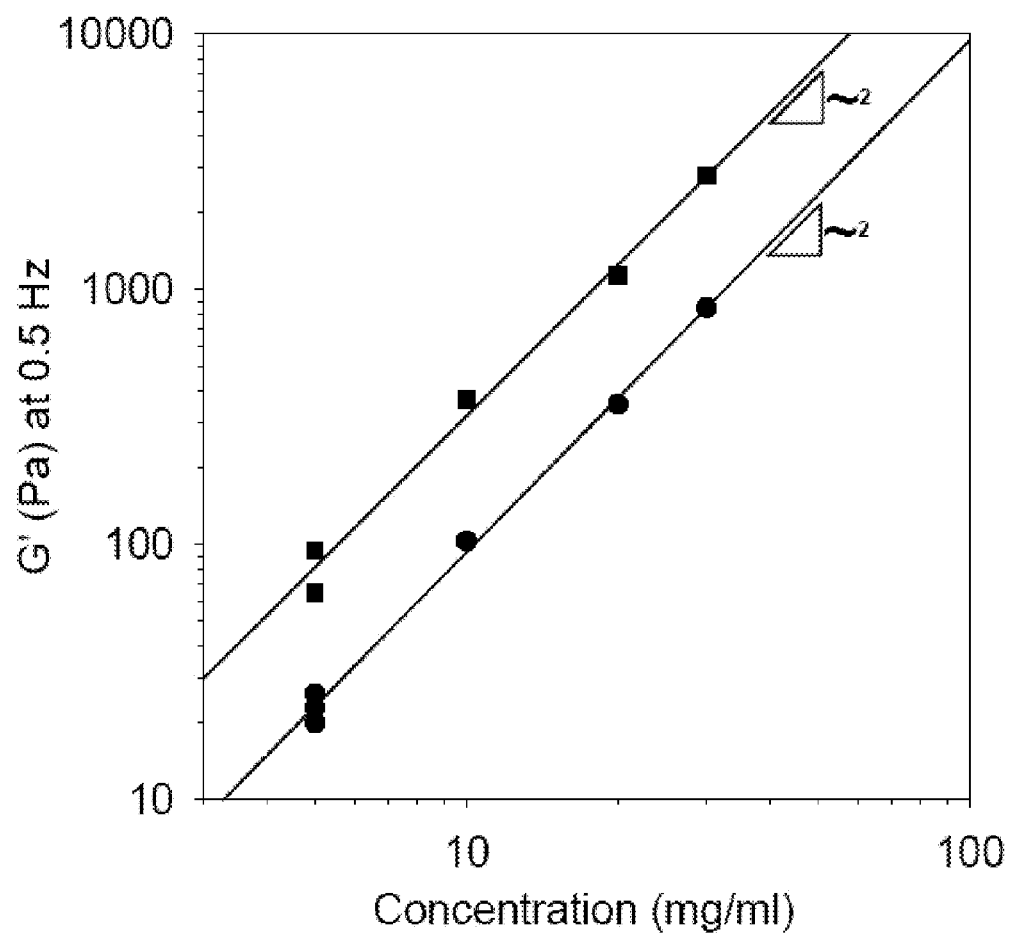

FIG. 16: Concentration dependence of the storage modulus at a frequency of 0.5 Hz for both the crosslinked and the non-crosslinked hydrogels. Both networks have storage moduli that are proportional to the concentration squared $[c]^2$.

EXAMPLES

Experimental Procedures

Materials. Chemicals were obtained from Merck KGaA (Darmstadt, Germany) if not otherwise stated. Manipulation and modification of DNA was performed as described previously (19). Restriction enzymes were obtained from New England Biolabs (Beverly, Mass., USA) and ligase from Promega Biosciences Inc. (San Luis Obispo, Calif., USA). DNA purification was performed using kits from Qiagen (Hilden, Germany). Synthetic oligonucleotides were obtained from MWG Biotech AG (Ebersberg, Germany). All cloning steps were performed in the *E. coli* strain DH10B from Novagen (Madison, Wis., USA).

Construction of the cloning vector pAZL. A cloning cassette with cohesive ends complementary to ones generated by BglII and HindIII was created by annealing two synthetic oligonucleotides CC1 (GATCGAGGAGGATCCATGGGA-CGAATTCACGGCTAATGAAAGCTTACTGCAC) (SEQ ID NO: 18) and CC2 (AGCTGTGCAGTAAGCTTTCATT-AGCCGTGAATTCGTCCCATGGATCCTCCTC) (SEQ ID NO: 19) Annealing was accomplished by decreasing the temperature of a 50 pmol/μl (each) oligonucleotide solution from 95° C. to 20° C. with an increment of 0.1° C./s. Mismatched double strands were denatured at 70° C. followed by another temperature decrease to 20° C. After repeating the 20° C.-70° C.-20° C. cycle ten times, ten additional cycles were performed with a denaturing temperature of 65° C. The resulting cloning cassette was ligated with a pFastbac1 vector (Invitrogen, Carlsbad, Calif., USA) digested with BglII and HindIII. Both restriction enzyme recognition sequences were destroyed upon this cloning step. The resulting new cloning vector was named pAZL.

Cloning of silk modules and NR-regions into the pAZL vector. Three amino acid modules derived from the dragline silk proteins ADF-3 and ADF-4 (FIG. 1E) were back translated into a DNA sequence considering bacterial codon usage. Corresponding complementary DNA oligonucleotides A1 (TCCGTACGGCCCAGGTGCTAGCGCCGCA-GCGGCAGCGGCTGGTGGCTACGGTCCGGGCTCTG-GCCAGCAGGG) (SEQ ID NO: 20) and A2 (CTGCTGGC-CAGAGCCCGGACCGTAGCCACCAGCCGCTGCCGC-TGCGGCGCTAGCACCTGGGCCGTACGGACC) (SEQ ID NO: 21), Q1 (TCCGGGCCAGCAGGGCCCGGGT-CAACAGGGTCCTGGCCAGCAAGGTCCGGGCCAGC-AGGG) (SEQ ID NO: 22) and Q2 (CTGCTGGCCCGGAC-CTTGCTGGCCAGGACCCTGTTGACCCGGGCCCTGC-TGGCCCGGACC) (SEQ ID NO: 23), C1 (TTCTAGCGCG-GCTGCAGCCGCGGCAGCTGCGTCCGGCCCGGGTG-GCTACGGTCCGGAAAACCAGGGTCCATCTGGCCC-GGGTGGCTACGGTCCTGGCGGTCCGGG) (SEQ ID NO: 24) and C2 (CGGACCGCCAGGACCGTAGCCAC-CCGGGCCAGATGGACCCTGGTTTTCCGGACCGTAG-CCACCCGGGCCGGACGCAGCTGCCGCGGCTGCAG-CCGCGCTAGAACC) (SEQ ID NO: 25) were synthesized and annealed as described above and ligated with the pAZL vector digested with BsgI and BseRI. NR-regions of spider silk genes adf-3 (gi|1263286) and adf-4 (gi|1263288) (obtained from Prof. Gosline, Vancouver, Canada) were amplified by PCR using the following primers:

```
                                            (SEQ ID NO: 26)
NR3f (GAAAAACCATGGGTGCGGCTTCTGCAGCTGTATCTG), (SEQ ID NO: 27)
NR3r (GAAAAGAAGCTTTCATTAGCCAGCAAGGGCTTGAGCTA
CAGATTG), (SEQ ID NO: 28)
NR4f (GAAAAACCATGGGAGCATATGGCCCATCTCCTTC)
and (SEQ ID NO: 29)
NR4r (GAAAAGAAGCTTTCATTAGCCTGAAAGAGCTTGGCTAA
TCATTTG).
```

For Flag sequences, the following primers and cassettes may be used:

PCR-Primer:

```
FLAG-N-chr-sense:
                                            (SEQ ID NO: 43)
5'-GAAAAACCATGGGCGAAAGCAGCGGAGGCGAT-3'

FLAG-N-chr-anti:
                                            (SEQ ID NO: 44)
5'-GAAAAGAAGCTTTCATTAGCCTGGGCTGTATGGTCC-3'

FLAG-C-chr-sense:
                                            (SEQ ID NO: 45)
5'-GAAAAACCATGGGTGCTTATTATCCTAGCTCGC-3'

FLAG-C-chr-anti:
                                            (SEQ ID NO: 46)
5'-GAAAAGAAGCTTTCATTAGCCATAAGCGAACATTCTTCCTAC-3'
```

Oligos for Repetitive Sequences from which Cassettes were Generated:

Module Y-(GPGGX)-ds:
(SEQ ID NO: 47)
5'-TCCGGGCGGTGCGGGCCCAGGTGGCTATGGTCCGGGCGGTTCTGGGC
CGGGTGGCTACGGTCCTGGCGGTTCCGGCCCGGGTGGCTACGG-3'

Module Y-(GPGGX)-cs:
(SEQ ID NO: 48)
5'-GTAGCCACCCGGGCCGGAACCGCCAGGACCGTAGCCACCCGGCCCAG
AACCGCCCGGACCATAGCCACCTGGGCCCGCACCGCCCGGACC-3'

Module sp-(spacer)-ds:
(SEQ ID NO: 49)
5'-TGGCACCACCATCATTGAAGATCTGGACATCACTATTGATGGTGCGG
ACGGCCCGATCACGATCTCTGAAGAGCTGACCATCGG-3'

Module sp-(spacer)-cs:
(SEQ ID NO: 50)
5'-GATGGTCAGCTCTTCAGAGATCGTGATCGGGCCGTCCGCACCATCAA
TAGTGATGTCCAGATCTTCAATGATGGTGGTGCCACC-3'

Module K-(GPGGAGGPY)-ds:
(SEQ ID NO: 51)
5'-TCCGGGCGGTGCTGGCGGTCCGTACGGCCCTGGTGGCGCAGGTGGGC
CATATGGTCCGGGCGGTGCGGGCGGTCCGTACGG-3'

Module K-(GPGGAGGPY)-cs:
(SEQ ID NO: 52)
5'-GTACGGACCGCCCGCACCGCCCGGACCATATGGCCCACCTGCGCCAC
CAGGGCCGTACGGACCGCCAGCACCGCCCGGACC-3'

Module X-(GGX)-ds:
(SEQ ID NO: 53)
5'-TGGCGCTGGTGGCGCCGGTGGCGCAGGTGGCTCTGGCGGTGCGGGCG
GTTCCGG-3'

Module X-(GGX)-cs:
(SEQ ID NO: 54)
5'-GGAACCGCCCGCACCGCCAGAGCCACCTGCGCCACCGGCGCCACCAG
CGCCACC-3'

PCR-products and pAZL vector were ligated after digestion with NcoI and HindIII. Cloning of synthetic modules as well as PCR-products resulted in the replacement of the cloning cassette's spacer, preserving the arrangement of its elements. For more efficient translation, the codon AGA (Arg), which is rarely translated in E. coli, was mutated to CGT (Arg) in NR3 and NR4 using PCR mutagenesis (19).

Construction of synthetic spider silk genes. Connecting of two gene fragments e.g. single modules, module multimers or NR-regions represented the basic step of the cloning strategy. For this purpose the pAZL vector, containing the designated 5'-terminal gene fragment was digested with BsaI and BsgI, while the vector comprising the 3'-terminal gene fragment was digested with BseRI and BsaI respectively (FIG. 1B). Ligation of the appropriate plasmid fragments yielded the connecting of the two gene fragments and led to the reconstitution of the pAZL vector's ampicillin resistance gene (Ap$^r$) which facilitated identification of correct constructs.

For gene construction, single modules were first connected to yield repeat units (FIG. 1D+FIG. 5). These were gradually multimerized and optionally linked with NR-regions. Finally, synthetic gene constructs as well as NR-regions were excised from the pAZL vector with BamHI and HindIII and ligated with the bacterial expression vector pET21a (Novagen) likewise digested, providing a T7-tag (MASMTGGQQMGR) (SEQ ID NO: 30) coding sequence (20). The fidelity of all constructs was confirmed by DNA sequencing.

Gene expression. All silk genes were expressed in the E. coli strain BLR [DE3] (Novagen). Cells were grown at 37° C. in LB medium to an $OD_{600}$=0.5. Before induction with 1 mM IPTG (Isopropyl-β-D-thiogalactosid), cells were shifted to 30° C. in the case of $(AQ)_{12}$, $(AQ)_{12}NR3$, $(QAQ)_8$, and $(QAQ)_8NR3$ and to 25° C. in the case of $C_{16}$, $C_{16}NR4$, NR3 and NR4 respectively. Alternatively cells were grown in a fermenter to an $OD_{600}$=40-50 using complex media (21) and the fed-batch technique (22). Again, before induction with 1 mM IPTG cells were shifted to 25° C. or 30° C., respectively. Cells expressing $(AQ)_{12}$, $(AQ)_{12}NR3$, $(QAQ)_8$, $(QAQ)_8NR3$, $C_{16}$ and $C_{16}NR4$ were harvested after 3-4 hours of induction while cells expressing NR3 and NR4 were harvested after 16 hours.

Protein purification. Cells were resuspended with 5 ml/g buffer containing 20 mM N-(2-hydroxyethyl)piperazine-N'-(2-ethanesulfonic acid) (HEPES) pH 7.5, 100 mM NaCl, 0.2 mg/ml lysozyme (Sigma-Aldrich, St. Louis, Mo., USA) and incubated at 4° C. for 30 min. Cells were lyzed by sonification using a HD/UW2200/KE76 ultrasonicator (Bandelin, Berlin, Germany) and genomic DNA was digested by incubating cell lysates with 0.1 mg/ml DNase I (Roche, Mannheim, Germany) and 3 mM $MgCl_2$ at 4° C. for 60 min. Insoluble cell fragments were sedimented at 50,000×g and 4° C. for 30 min. Soluble E. coli proteins of lysates containing $(AQ)_{12}$, $(AQ)_{12}NR3$, $(QAQ)_8$, $(QAQ)_8NR3$, $C_{16}$ and $C_{16}NR4$ were precipitated by heat denaturation at 80° C. for 20 min while lysates containing NR3 and NR4 were heated to 70° C. for the same length of time. Precipitated proteins were removed by sedimentation at 50,000×g for 30 min. Silk proteins, which remained soluble during heat denaturation, were precipitated with 20% ammonium sulphate (800 mM) ($(AQ)_{12}$, $(AQ)_{12}NR3$, $(QAQ)_8$, $(QAQ)_8NR3$, $C_{16}$ and $C_{16}NR4$) or 30% ammonium sulphate (1200 mM) (NR3 and NR4) at room temperature and harvested by centrifugation at 10,000×g for 10 min. Pellets of $(AQ)_{12}$, $(AQ)_{12}NR3$, $(QAQ)_8$, $(QAQ)_8NR3$, NR3 and NR4 were rinsed with a solution containing the same concentration of ammonium sulphate as used for precipitation and dissolved in 6 M guanidinium chloride (GdmCl). In contrast $C_{16}$ and $C_{16}NR4$ were washed with 8 M urea and dissolved in 6 M guanidinium thiocyanate (GdmSCN). All proteins were dialyzed against 10 mM $NH_4HCO_3$. Precipitates formed during dialysis were removed by sedimentation at 50,000×g for 30 min and the remaining soluble silk proteins were lyophilized. Prior to analysis lyophilized protein was dissolved in 6 M GdmSCN followed by dialysis against appropriate buffers. Aggregates were removed by sedimentation at 125,000×g for 30 min. Protein concentrations were determined photometrically in a 1 cm path length cuvette at 276 nm using calculated extinction coefficients (Table 1) (23). Identity of proteins was confirmed by sodium dodecylsulfate-polyacrylamide gel electrophoresis (SDS-PAGE; 10% Tris-Glycine gels for proteins>20 kDa and 10-20% Tris-Tricine gels (Invitrogen) for proteins<20 kDa) followed by blotting onto polyvinylidene fluoride (PVDF) membranes (Millipore, Billerica, Mass., USA) and detection using a mouse anti-T7 monoclonal antibody (Novagen, 1:10,000) as primary and anti-mouse IgG peroxidase conjugate (Sigma-Aldrich, 1:5,000) as secondary antibody. Peroxidase activity was visualized using the $ECL^{plus}$ western blot detection kit from Amersham Biosciences (Piscataway, N.J., USA).

Fluorescence. Fluorescence spectra were recorded on a FluoroMax Spectrofluorometer (Jobin Yvon Inc, Edison, N.J., USA). Spectra were taken using a protein concentration of 100 μg/ml in 10 mM Tris(hydroxymethyl)aminomethane (Tris)/HCl (pH 8.0) at room temperature. Integration time was 1 s, step size was 0.5 nm and band widths were 5 nm (excitation) and 5 nm (emission), respectively.

Secondary structure analysis. Far-UV circular dichroism (CD) spectra were obtained using a Jasco 715 spectropolarimeter equipped with a temperature control unit (Jasco International Co. Ltd., Tokyo, Japan). All spectra were taken at a protein concentration of 150 µg/ml in 5 mM Tris/HCl (pH 8.0) in a 0.1 cm path length quartz cuvette at 20° C. Scan speed was 20 nm/min, step size was 0.2 nm, integration time was set to 1 s and band width was 1 nm. Four scans were averaged and buffer-corrected. Thermal transitions were analyzed with a heating/cooling increment of 1° C./min at 220 nm.

Solubility assay. To determine the maximal concentration of soluble proteins, a 1 mg/ml (=0.1% (w/v)) solution in 10 mM Tris/HCl pH 8.0 was concentrated by ultra filtration using a 10,000 Da molecular weight cut off polyether sulfone membrane (Vivascience AG, Hannover, Germany). At distinct intervals samples were taken from the solution until the protein started to precipitate. Samples were diluted in 10 mM Tris pH 8.0 to determine protein concentration photometrically.

Aggregation assay. All samples were adjusted to 1 mg/ml in 10 mM Tris/HCl pH 8.0. For testing ionic effects on silk protein aggregation, salts were added to final concentrations of 300 mM. The effect of acidification was investigated by adding HCl to a final concentration of 100 mM (pH=1). All samples were incubated at room temperature for 1 hour. Protein precipitates were removed from all samples by sedimentation at 125,000×g for 25 min and the amount of the remaining soluble protein was determined photometrically. Since the sum of soluble and aggregated protein had to equal the initial amount of soluble protein, the percentage of aggregated protein could be calculated by subtracting the amount of soluble protein from the initially used amount of protein.

Results

A cloning strategy for designing silk-like proteins. Expression of authentic spider silk genes in bacterial hosts is inefficient (24) since some gene sections contain codons not efficiently translated in bacteria. In addition, gene manipulation and amplification by PCR is difficult due to the repetitive nature of silks. In order to investigate properties of spider silk proteins, cloning strategies have been employed using synthetic DNA modules with a codon usage adapted to the corresponding expression host. Synthetic genes were obtained which coded for proteins resembling the repetitive regions of spider silks (25-28). Importantly, none of these protein designs included the carboxyl terminal NR-regions that are found in all dragline silks.

The inventors developed a seamless cloning strategy (29) that allowed controlled combination of different synthetic DNA modules as well as authentic gene fragments. The cloning vector pAZL was designed comprising a cloning cassette with a spacer acting as placeholder for synthetic genes, and recognition sites for the restriction enzymes BseRI and BsgI (FIG. 1A). Since recognition and cleavage sites of these enzymes are 8 (BseRI) or 12 (BsgI) nucleotides apart, translation start and stop codons as well as additional restriction sites required for the excision of assembled genes could be positioned close to the spacer.

In a first cloning step the spacer region of pAZL was replaced by a synthesized DNA module (for module design see below). Subsequently two modules could be joined in a site-directed way (see materials and methods and FIG. 1B). The complementary 3'-single strand extensions GG (sense) and CC (antisense) generated by cleavage with BsgI and BseRI were used for connecting two modules (FIG. 1C). Thus the DNA sequence required to link two modules was confined to a glycine codon (GGX). Glycine is naturally abundant in spider silk proteins (~30%), therefore modules could be designed without the need to search for restriction endonuclease recognition sites which, after translation, match authentic amino acid sequences. Since the arrangement of the cloning cassette's elements remained unchanged upon cloning and multimerization, a variety of module combinations could be constructed (FIG. 1D).

Design, synthesis and purification of synthetic spider silks. The inventors chose the dragline silk proteins ADF-3 and ADF-4 (3) from the garden spider Araneus diadematus as templates for the synthetic constructs. The partially identified primary structure of ADF-3 largely consists of repeat units, which all comprise a consensus sequence including a poly-alanine motif. Length of individual repeat units is determined by varying numbers of the motif GPGQQ. To mimic the repetitive sequence of ADF-3 we designed two modules. One module, termed A, was derived from the poly-alanine containing consensus sequence (FIG. 1E). A second module termed Q contained four repeats of the GPGQQ motif. To study different length repeat units, one or two Q modules were combined with one A module to obtain (AQ) or (QAQ). These repeat units were multimerized to generate synthetic genes coding for the repetitive proteins (rep-proteins) $(AQ)_{12}$ and $(QAQ)_8$.

The repetitive part of ADF-4 is generally composed of a single conserved repeat unit displaying only slight variations. The inventors combined these variations and designed one consensus module termed C (FIG. 1E), which the inventors multimerized to obtain the rep-protein $C_{16}$. The number of module repeats in all synthetic genes was chosen to code for proteins of similar molecular mass (~50 kDa).

ADF-3 and ADF-4 both display homologous NR-regions at their carboxyl termini, comprising 124 and 109 amino acids respectively. Gene sequences coding for these regions were amplified by PCR, and codons problematic for bacterial expression were changed to more suitable codons by site directed mutagenesis (see materials and methods). Therefore, all of the synthetic genes used could be combined with the appropriate authentic NR-regions yielding genes coding for the repNR-proteins $(AQ)_{12}NR3$, $(QAQ)_8NR3$ and $C_{16}NR4$. Additionally NR3 and NR4 could be expressed alone.

After bacterial synthesis silk proteins were purified by a heat step followed by an ammonium sulfate precipitation. The identity of the proteins was confirmed by immunoblotting, using antibodies directed against T7 peptide tag sequences, attached to the amino-terminal end of all silk proteins (FIG. 2A). Although all rep-proteins and all repNR-proteins had similar molecular weights (Table 1) they displayed different migration velocities when subjected to SDS-PAGE. This effect might be caused by aberrant binding of dodecylsulfate to the proteins due to different amino acid composition, leading to variation of the proteins' net charges. Besides full length proteins, immunoblotting revealed traces of proteins with lower molecular weight within preparations of repNR-proteins. Binding of the anti T7-tag antibody to these proteins identified them as silk proteins lacking part of their carboxyl-terminal end. Analyzing each purified protein by SDS-PAGE and silver staining, no further proteins were detected in all protein preparations (FIG. 2B). Protein purity additionally was determined by measuring fluorescence emission. Incident light of 280 nm wavelength leads to excitation and fluorescence emission of tyrosines and tryptophanes while light of 295 nm exclusively excites the latter. Since none of the designed spider silk proteins comprised tryptophanes, fluorescence emission upon excitation with 295 nm would have been indicative for contaminating E. coli proteins, which on average contain 1.5% of tryptophane (30). Fluorescence measurements of all silk protein preparations revealed emission spectra akin to the spectrum of tyrosine, which occurs abundantly in the silk proteins. In contrast, no tryptophane fluorescence could be detected, indicating high purity of the protein preparations (data exemplarily shown for $C_{16}$NR4 in FIG. 2B).

Bacterial production of synthetic silk proteins in Erlenmeyer flasks yielded similar protein amounts for all constructs. Yields of individual preparations ranged from 10 to 30 mg of purified protein per liter of culture medium. Fermentation of cells was employed in order to investigate the possibility to up-scale protein synthesis. Yields of $(QAQ)_8$NR3 and $C_{16}$NR4 thus could be increased to 140 and 360 mg/l, respectively.

RepNR-proteins consist of a poorly structured repetitive region and a highly structured non-repetitive domain. Secondary structure was investigated by CD spectroscopy. Rep-proteins unveiled spectra typical for intrinsically unstructured proteins. In contrast NR-proteins revealed spectra indicative of high secondary structure content. These regions seem to represent independently folding protein domains. Spectra of repNR-proteins roughly corresponded to a combination of the rep- and NR-spectra weighted according to their share in the repNR-proteins. Although a minor structural change within the rep-regions or NR-domains upon mutual linking can not be excluded it is likely that the repNR-proteins are composed of a region displaying mostly random coil structure and a carboxyl terminal folded protein domain. Strikingly spectra of repNR-proteins were similar to CD-spectra obtained from the major ampullate silk dope directly extracted from spiders (*Nephila clavipes*) (9).

Silk proteins refold after thermal and chemical denaturation. Investigating structural changes by CD-spectroscopy upon heating, no cooperative temperature transitions were observed for rep-proteins between 20° C. and 90° C., an effect which has also been observed for other intrinsically unfolded proteins (31; 32) (FIG. 3). Since repNR-proteins were at least partially structured, thermal unfolding of the structured region should be detectable at elevated temperatures. Accordingly, cooperative thermal transitions were observed. Midpoints of temperature transitions were 67° C. ($(QAQ)_8$NR3), 66° C. ($(AQ)_{12}$NR3) and 72° C. ($C_{16}$NR4), respectively (FIG. 3B and Table 1). Furthermore, all thermal transitions were completely reversible. The reversibility of the structural changes upon heating explained the high recovery of soluble silk proteins after the heat step employed during protein purification. Tris was used to buffer all solutions investigated by CD spectroscopy, because of good spectral properties and little capacity to promote silk protein aggregation. Due to the strong temperature dependence of Tris buffered solutions, the pH of the samples was expected to shift from pH 8 to pH 6 upon heating from 20° C. to 90° C. (19). However, temperature transitions of silk proteins in phosphate buffer at pH 8, displaying a temperature independent pK-value, revealed equal midpoint temperatures (data not shown) although they were not entirely reversible probably due to protein aggregation (see below). This indicated that thermal transitions of silk proteins were not influenced by thermally induced changes of the pH in Tris-buffered solutions.

The effect of chemical de- and renaturation on secondary structure was investigated by measuring circular dichroism of repNR-proteins in Tris buffer, after dialysis against 6 M GuaHCl and renaturation by dialysis against Tris Buffer. The identical spectra of the initial and the refolded proteins indicated that chemical denaturation is reversible (data not shown).

The solubility of silk proteins is determined by their repetitive sequences. In order to gain high protein concentrations in the dope, silk proteins have to be highly soluble. We tested the maximum concentrations at which rep- and repNR-proteins remained soluble to identify primary structure elements determining solubility. All proteins comprising the modules A and Q could be concentrated by ultra filtration to more than 30% w/v without forming visible aggregates, regardless of the presence of the NR-domain. In contrast, proteins containing the module C could only be concentrated to 8% w/v ($C_{16}$) and 9% w/v ($C_{16}$NR4), respectively (Table 1). Both proteins formed a gel-like solid upon further concentration (data not shown). Thus, solubility of the silk proteins was solely determined by their repetitive sequences and was not influenced by the NR-domain.

Potassium does not promote aggregation of synthetic silk proteins, independent of their primary structure. pH, ions, such as potassium and phosphate, and mechanical stress are involved in natural silk assembly. Here we wanted to investigate how these factors promote the assembly of synthetic silk proteins. Since we were unable to imitate the authentic assembly process, which requires pre-orientation of the involved proteins as found in the liquid crystalline dope (33), we performed an aggregation assay starting with protein solutions not displaying orientational order. None of the tested rep-, repNR- and NR-proteins displayed significant aggregation (<5%) when incubated in buffer, indicating that all proteins were intrinsically soluble under the testing conditions (FIG. 4). To investigate whether addition of ions caused aggregation by increasing the ionic strength, proteins were incubated with sodium chloride. However no aggregation was observed. In contrast to sodium, potassium has previously been reported to specifically promote silk aggregation (34). Yet, potassium chloride also showed no influence on solubility of the synthetic silk proteins (FIG. 4).

Acidification and addition of phosphate initiate aggregation of rep proteins depending on their primary structure. The exact function of acidification during spider silk assembly has not yet been determined. However it seems likely that negatively charged groups (e.g. posphoryl groups) are protonated thus reducing the net charge and repulsion of spider silk proteins. Since the synthetic silk proteins did not contain chemical groups displaying a $pK_A$-value within the range of the pH-shift observed during the spinning process, the inventors aimed to mimic this effect by protonating all terminal and side chain carboxyl-groups. $(QAQ)_8$ and $(AQ)_{12}$, displaying only the terminal carboxyl group, showed no (<5%) and weak (18%) aggregation at pH 1. Interestingly protonation $C_{16}$'s 16 glutamate residues also caused only weak aggregation (8%) (FIG. 4). Phosphate which has been described to be added to the dope during the spinning process caused no aggregation of $(QAQ)_8$ and weak precipitation of $C_{16}$ (12%). In contrast, $(AQ)_{12}$ displayed an increased tendency to aggregate (47%) after treatment with potassium phosphate. Similar results were obtained using sodium phosphate, indicating that the effect is specifically caused by phosphate ions (data not shown).

NR-domains amplify the response to factors that promote aggregation. To investigate the influence of NR-domains, aggregation of repNR-proteins as well as NR-proteins at low pH and upon treatment with phosphate was tested. Acidification of $(QAQ)_8$NR3 and $(AQ)_{12}$NR3, as well as NR3 caused weak aggregation (10%, 15% and 13%), which was in the range displayed by the corresponding rep-proteins. Interestingly, although the NR4-domain did not precipitate at pH 1 (0%), $C_{16}$NR4 showed strong aggregation at pH 1 (70%). Thus the combination of the repetitive $C_{16}$ and the NR4-domain, which did not significantly aggregate upon acidification, led to a protein highly sensitive to this aggregation promoting factor. Similar results were obtained for the addition of phosphate. While neither NR3 nor NR4 showed aggregation in the presence of phosphate (1% and 0%), the addition of the NR-domains to the repetitive regions caused an increased aggregation of the repNR-proteins in comparison to rep-proteins ((QAQ)$_8$NR3: 57%, (AQ)$_{12}$NR3: 81%, C$_{16}$NR4: 80%).

Using a cloning strategy that allows seamless and controlled assembly of DNA modules, synthetic genes were constructed coding for spider silk-like proteins. The design of proteins yielded different combinations of repeat units and naturally occurring NR-regions, to systematically test the properties of such single primary structure elements. Structural analysis by CD-spectroscopy revealed that repetitive regions are mostly unstructured in their soluble state, displaying properties common to other intrinsically unfolded proteins (31 ;32). The same conformational state as been proposed for the largest part of the major ampullate content (10) which is dominated by repetitive protein sequences. In contrast NR-regions were found to represent independently folding protein domains that adopt their conformation after heat denaturation as well as treatment with chaotropic agents. Because of their relative small size compared to repetitive regions the influence on overall structural properties was small in repNR-proteins.

In natural spider silks displaying repetitive regions of several hundred kDa the structural contribution of the NR-regions can be expected to be even smaller, explaining the missing evidence for their presence in investigations of major ampullate content. Because of the reversibility of thermal and chemical denaturation of repNR-proteins and the similarity of CD data presented in this work and obtained from natural silk dope, it can be assumed that even after treatment with heat and chaotropic reagents during purification and sample preparation all investigated spider silk components in aqueous solutions were in a conformational state comparable to that of natural silk proteins within the dope.

According to Uversky et al. intrinsic unfolding of proteins can be predicted based on their net charge and mean hydropathicity. The net charge of a protein is used to calculate a "boundary" hydropathicity. If the mean hydropathicity of the protein is below the "boundary" value, the protein is predicted to be intrinsically unfolded (35 ;36). In accordance with the presented results the repetitive sequences (QAQ)$_8$ and (AQ)$_{12}$ are predicted to be intrinsically unfolded (Table 1). Intrinsic unfolding of a protein means that interactions of the amino acid residues with the surrounding solvent are more favourable than with amino acids of the same or other polypeptide chains. Accordingly, (QAQ)$_8$ and (AQ)$_{12}$ are soluble even at high concentrations. In contrast, C$_{16}$ displays a hydropathicity slightly above the boundary value. While still revealing properties of intrinsically unfolded proteins interactions between polypeptide chains are becoming more favorable at high concentrations leading to aggregation of the protein and resulting in a lower solubility compared with (QAQ)$_8$ and (AQ)$_{12}$ (Table 1).

As repetitive sequences constitute the largest fraction of spider silk proteins, they likely determine many of the proteins' properties. Accordingly solubilities of repNR-proteins do not significantly differ from rep-proteins. The solubility and calculated hydropathicity of (QAQ)$_8$ and (AQ)$_{12}$ correlate well with the values of authentic ADF-3 (Table 1). C$_{16}$ and ADF-4 both display lower solubility, although C$_{16}$ does not share the high intrinsic insolubility of ADF-4. This difference can be explained by higher hydropathicity and lower net charge of ADF-4 compared to C$_{16}$.

In contrast to repetitive regions, NR-domains represent only a small fraction of spider silk proteins. Both NR-domains revealed a structure rich in α-helices. Due to the high similarity between the NR-domains of ADF-3 and ADF-4 (81% similarity and 67% identity) it can be assumed, that both might fulfill related functions. Further information about the function of the NR-domains was obtained when investigating aggregation of the silk proteins upon treatment with factors known to induce the assembly of silk proteins in vivo. Reducing negative charges by protonation of the silk proteins' carboxyl groups was expected to mainly affect proteins comprising the C module. Accordingly, proteins composed of modules A and Q, which do not contain aspartates or glutamates, did not show more than weak aggregation. C$_{16}$ even after neutralization of its 16 negative charges remained mostly soluble. Strikingly the combination of the NR4-domain, which did not show any response to acidification by itself, and the weakly aggregating C$_{16}$ resulted in a protein highly sensitive to protonation. Thus charge reduction of the repetitive region and the presence of the NR-domain are required for efficient aggregation. Similar results were obtained when phosphate was added to the protein solutions. Phosphate, like other lyotropic ions is known to increase the surface tension of water, promoting hydrophobic interactions (37). In the case of spider silk proteins it is likely that the addition of phosphate initiates interactions between the hydrophobic poly-alanine motifs, causing the aggregation of the proteins. Accordingly aggregation of (AQ)$_{12}$ was higher than of (QAQ)$_8$ which contains one third less poly-alanine motifs than (AQ)$_{12}$. C$_{16}$ displaying the longest and highest number of poly-alanine motifs however did not show the strongest aggregation upon phosphate treatment. A possible explanation for this unexpected result might be the repulsion of the negatively charged glutamate side chains and phosphate ions leading to their exclusion from the surrounding solvent and a weakening of their lyotropic effect. Even though both NR-domains did not respond to the addition of phosphate, their addition to the rep-proteins strongly increased phosphate sensitivity. Although the presented data is not sufficient to draw a final conclusion it seems likely that the NR-domains function as unspecific enhancers of sensitivity to aggregation promoting factors. For efficient aggregation their presence is as important as the ability of repetitive regions to respond to these factors.

The mechanism of this enhancement might involve changes in the oligomeric status of the silk proteins. NR-domains have been found to form disulfide bridged dimers (38). Further oligomerization might lead to increased local concentrations of polypeptide sequences required for initiating aggregation which is assisted by solvent conditions that favour the formation of intermolecular interactions.

The present protein engineering approach, which combines synthetic repetitive sequences with authentic NR-regions, reveals that proteins closely resembling authentic silk proteins can be produced at high yields. The bacterial expression system as well as the simple and cheap purification process, which can easily be scaled up, provides the basis for cost-efficient industrial scale production of spider silk-like proteins. Based on the present studies, the molecular mechanisms of spider silk assembly can be further investigated, which will provide the knowledge required for artificially spinning silk threads from recombinant proteins and for gaining new materials for biotechnological and medical applications.

Assembly of Spider Silk Derived Proteins

The following experiments were performed to demonstrate that proteins derived from spider silk sequences ADF-3 (SEQ ID NO:1) or ADF-4 (SEQ ID NO:2) can be assembled into morphological distinct forms. Proteins (AQ)$_{24}$NR3 and $C_{16}$NR4 were constructed, produced and prepared in aqueous solutions as described in *Biochemistry* 2004 Vol. 43 pp. 13604-11362. If not otherwise mentioned protein solutions contained 10 mM Tris-(hydroxymethyl)-aminomethan (Tris) pH 8.0.

1. Spheres

Protein spheres displaying diameters ranging between 0.5 and 2 µm (FIG. 7a) were generated by adding 0.8 M ammonium sulphate to a 0.2% (w/v) $C_{16}$ solution.

2. Nanofibrils

Nanofibrils displaying diameters between 0.7 and 4 nm (FIG. 7b) were formed by incubating a 1% (w/v) $C_{16}$NR4 solution at room temperature for 2 weeks.

3. Microfibrils

For the formation of microfibrils 5-10 µl of a 25% (w/v) $(AQ)_{24}$NR3 solution were slowly injected into 0.5 M potassium phosphate pH 8.0, forming a stable drop of protein solution. After incubation for 1 min the protein drop was removed from the solution using tweezers. After an additional incubation time of 1 min in air a protein fibril could be drawn from the protein drop at a rate of approximately 2 cm/s using a second set of tweezers. The fibrils displayed a round cross section with a diameter of 4 µm (FIG. 7c,d).

4. Foams

Protein foams (FIG. 7e,f) were generated from solutions containing 2.5 mM ammonium peroxodisulfate (APS), 100 µM tris(2,2'-bipyridyl)dichlororuthenium(II) (Rubpy) and 10% (w/v) $(AQ)_{24}$NR3 or 2% (w/v) $C_{16}$NR4. The protein solutions were frothed up with air. To stabilize the resulting foam structure proteins were crosslinked by exposition to visible light from a tungsten lamp for 1 min (Protocol: *PNAS* 1999 Vol. 96 pp. 6020-6024). Foams were subsequently dried at 95° C.

5. Gels $C_{16}$NR4 nanofibrils at 1% (w/v) concentration displayed a gel like appearance which easily could be disrupted by agitation or shearing. To improve the mechanical properties of the gel APS and Rubpy were allowed to enter the gel by diffusion to yield final concentrations of 10 mM APS and 100 µM Rubpy. After light induced crosslinking (see section 4) dimensionally stable gels could be obtained (FIG. 7g).

6. Films 6.1 Soluble State of Spider Silk Proteins

In order to cast films the inventors used the two synthetic silk proteins, $(AQ)_{24}$NR3 and $C_{16}$, which are derived from the dragline silk proteins ADF-3 and ADF-4 from the garden spider Araneus diadematus (see also above for further explanations). They chose these two different proteins based on previous observations that ADF-3 and ADF-4 as well as its derivatives display a markedly different behaviour regarding solubility and assembly. Aqueous solutions of both proteins could be prepared by dissolving lyophilized proteins in 6 M guanidinium thiocyanate and subsequent removal of the salt by dialysis against a low salt buffer such as 5 mM potassium phosphate pH 8.0. Lyophilized proteins could also be directly dissolved in HFIP. Measuring circular dichroism (CD) of protein solutions revealed a different influence of the two solvents on secondary structure. In aqueous solution both proteins displayed a CD-spectrum with a single minimum at a wavelength below 200 nm which is indicative of a mainly random coiled protein (FIG. 8). In contrast, the spectra of both proteins in HFIP displayed one minimum at 201-202 nm and an additional minimum $((AQ)_{24}NR3)$ or shoulder $(C_{16})$ at 220 nm which is indicative of an increased α-helical content (FIG. 8).

6.2 Film Formation

Films were cast on a polystyrene surface (or on quartz glass for CD-measurements) from HFIP solutions containing 2% w/v protein. After evaporation of the solvent, $(AQ)_{24}$NR3 and $C_{16}$ both formed transparent films that could easily be peeled off the surface (FIG. 9 and data not shown). Assuming complete evaporation of the solvent and the density of the protein film to be identical with the reported value of 1.3 g/cm³ for spider dragline silk, the thickness of the films was calculated to range from 0.5 to 1.5 µm. As-cast (freshly prepared) films made of either protein dissolved upon contact with water. Since water insolubility is a prerequisite for most applications of protein films, the inventors looked for a processing method in order to render films insoluble. Potassium phosphate has been known to induce aggregation and formation of chemically stable structures of the employed silk proteins. Accordingly, processing (incubating) of as-cast films with 1 M potassium phosphate resulted in the conversion of films into a water insoluble state.

6.3 Secondary Structure

To investigate the structural properties of the protein films, their secondary structure was investigated by CD-spectroscopy. As-cast films revealed a spectrum with two minima at 208 nm and 220 nm, indicative of a high α-helical content (FIG. 10). After processing with 1 M potassium phosphate, films revealed spectra with a single minimum at 218 nm which is typical for a β-sheet rich structure. Thus, the transition from water solubility to water insolubility paralleled a conversion of the protein's secondary structure from α-helix to β-sheet.

6.4 Chemical Stability

To test the chemical stability, films were exposed to 8 M urea, 6 M guanidinium hydrochloride and 6 M guanidinium thiocyanate (Table 2). As-cast films of both proteins as well as processed films of $(AQ)_{24}$NR3 were soluble in these denaturants. In contrast, processed films of $C_{16}$ could only be dissolved in guanidinium thiocyanate. This remarkable chemical stability of $C_{16}$ films is identical to that of recombinantly produced and assembled ADF-4 and that of natural dragline silk. Previous studies correlated assembly properties and stabilities of assembled structures directly with the amino acid sequences of the silk proteins. It therefore can be concluded, that properties of spider silk films can directly be modified by altering the primary structure of the silk protein via manipulation of the corresponding silk gene.

6.5 Film Modification

Many applications of protein films require the presence of specific functionalities on the film's surface. In order to demonstrate, that our spider silk protein films can be modified with small organic molecules as well as biological macromolecules like proteins, the chromophor fluorescein and the enzyme β-galactosidase were chemically coupled to processed $C_{16}$ films. The coupling was achieved by activating surface exposed carboxyl groups of $C_{16}$ using 1-ethyl-3-(3-dimethylaminopropyl)carbodiimide (EDC) (for details of the reactions see supplementary material indicated below). The films were then incubated with ethylenediamine leading to the formation of an amide. The remaining free amino group of ethylenediamine was subsequently coupled to fluorescein-isothiocyanate resulting in the efficient covalent linkage of the fluorescein (FIG. 11A) via formation of a stable thiourea derivative. Similarly, incubation of (3-galactosidase with EDC-activated $C_{16}$ films led to the formation of amide bonds between carboxyl groups of $C_{16}$ and primary amines (e.g. from lysine residues) of β-galactosidase which were accessible at the enzyme's surface. After repeated washing of such modified films, β-galactosidase activity could be detected using 5-bromo-4-chloro-3-indolyl-β-D-galactopyranoside (X-Gal) as a substrate (FIG. 11B).

6.6 Conclusion

Herein, it could be demonstrated that protein films can be obtained from synthetic spider silk proteins. The films, which initially were water soluble, can be processed with potassium phosphate leading to water-insolubility which is a major requirement for many applications. Comparison of the chemical stabilities of films made from two different synthetic spider silk proteins suggests that the properties of the films are based on the primary structure of the proteins. Thus, it will be possible to generate silk proteins that form films displaying specific properties. Since different functional molecules can be covalently attached to the film's surface, a great variety of technical or medical applications can be approached in the future.

6.7 Supplementary Materials and Results
Preparation of Protein Solutions

Protein production and purification was performed as described previously. To obtain aqueous solutions of $(AQ)_{24}$ NR3 and $C_{16}$, lyophilized protein was dissolved in 6 M guanidinium thiocyanate at a concentration of 10 mg/ml and subsequently dialyzed against 5 mM potassium phosphate pH 8.0. Aggregates were removed by sedimentation at 15,000×g for 10 min. Protein concentrations were determined photometrically in a 1 cm path length cuvette at 276 nm using calculated extinction coefficients of 73950 $M^{-1}$ $cm^{-1}$ for $(AQ)_{24}NR3$ and 46400 $M^{-1}$ $cm^{-1}$ for $C_{16}$. Alternatively, lyophilized silk proteins were dissolved directly in hexafluoroisopropanol (HFIP).

Secondary Structure Analysis

Far-UV circular dichroism (CD) spectra were obtained using a Jasco 715 spectropolarimeter (Jasco International Co. Ltd., Tokyo, Japan). Spectra of soluble proteins were taken at a protein concentration of 200 μg/ml in 5 mM potassium phosphate (pH 8.0) or HFIP in a 0.1 cm path length quartz cuvette at 20° C. For measuring films, 100 μl of a 2 mg/ml protein solution in HFIP were spread on a plain quartz glass of 4 cm² and air-dried before CD-measurement. Scan speed was 20 nm/min, step size was 0.2 nm, integration time was set to 1 s and band width was 1 nm. Four scans were averaged.

Film Modification

1. Coupling of Fluorescein to $C_{16}$ Film Surfaces

Films were prepared by spreading 15 μl per well of 20 mg/ml $C_{16}$ in HFIP on the bottom of a 24-well plate. After evaporation of HFIP, films were incubated for 5 minutes with 1 M potassium phosphate. After rinsing with water, carboxyl groups were activated by incubation for 15 min with 100 mM 2-(N-morpholino)ethanesulfonic acid (MES) pH 5.0, 100 mM 1-ethyl-3-(3-dimethylaminopropyl)carbodiimide (EDC) and 20 mM N-hydroxysulfo-succinimide (NHS). Subsequently ethylenediamine was added to yield a final concentration of 500 mM. After 2 h of incubation films were thoroughly rinsed with water. Finally, films were incubated for 1 h with 1 mg/ml fluoresceinisothiocyanate in 100 mM sodium carbonate pH 9.0, followed by rinsing with water and air-drying.

2. Coupling of β-galactosidase to $C_{16}$ film surfaces

Films were prepared and activated as described above. After 15 min of incubation with EDC/NHS, films were rinsed with water and subsequently incubated for 2 h with a solution containing 100 μg/ml β-galactosidase, 4 mM $KH_2PO_4$, 16 mM $Na_2HPO_4$, 115 mM NaCl (PBS). After thorough rinsing with PBS, enzymatic activity was tested on the film surface.

β-Galactosidase Assay

β-galactosidase coupled films were incubated for 16 h at room temperature with a solution containing 100 mM sodium phosphate pH 7.0, 10 mM potassium chloride, 1 mM magnesium sulfate, 50 mM β-mercaptoethanol and 2 mg/ml 5-bromo-4-chloro-3-indolyl-β-D-galactopyranoside (X-Gal).

7. Additional Hydrogels

The repetitive part of ADF-4 is generally composed of a single conserved repeat unit displaying only slight variations. The inventors combined these variations and designed one consensus module termed C (GSSAAAAAAAASGPG-GYGPENQGPSGPGGYGPGGP) (SEQ ID NO: 5), which was multimerized to obtain the rep-protein $C_{16}$, which will result in a protein of a molecular mass of 48 kDa.

$C_{16}$ silk gene was expressed in the E. coli strain BLR [DE3](Novagen). Cells were grown at 37° C. in LB medium to an $OD_{600}$=0.5. Before induction with 1 mM IPTG (Isopropyl-β-D-thiogalactosid), cells were shifted to 25° C. Cells were harvested after 3-4 hours of induction.

$C_{16}$ protein was purified as described in Huemmerich et at (40). Pellets of $C_{16}$ were washed with 8 M urea and dissolved in 6 M guanidinium thiocyanate (GdmSCN) before dialysis against 10 mM $NH_4HCO_3$. Precipitates formed during dialysis were removed by sedimentation at 50,000×g for 30 min and the remaining soluble silk proteins were lyophilized. Prior to analysis lyophilized protein was dissolved in 6 M GdmSCN followed by dialysis against 10 mM Tris/HCl. Aggregates were removed by sedimentation at 125,000×g for 30 min. Protein concentrations were determined photometrically in a 1 cm path length cuvette at 276 nm using calculated extinction coefficient (40).

$C_{16}$ self-assembled into nanofibers at concentrations between 5 and 30 mg/ml after the addition of 10% w/v of methanol (FIG. 12). Strikingly, at the concentrations used the nanofibers led to the formation of fiber network representing hydrogels. $C_{16}$ hydrogels could easily be disrupted by agitation or shearing. To improve the mechanical properties of the gel ammonium peroxodisulfate (APS), and Tris(2,2'-bipyridyl)dichlororuthenium(II) (Rubpy) were allowed to enter the gel by diffusion to yield final concentrations of 10 mM APS and 100 μM Rubpy. To gain dimensionally stable gels proteins were crosslinked by exposition to visible light from a tungsten lamp for 1 min (IV) (FIG. 13).

Dynamic rheological measurements of the crosslinked and non-crosslinked hydrogels were performed using a Physica MCR 301 with a 25 mm Plate-Plate geometry. The gap between the upper plate and the sample dish was set by first moving the upper plate approximately 2 mm above the surface of the sample. The upper plate was lowered very slowly (5 μm/s), while monitoring the normal force and was stopped at a limit normal force of 0.1 N.

After finding adequate gap sizes for the samples, the samples were sheered at 0.5 Hz and 1% deformation until the normal force equilibrated to a constant value. The dynamic rheology measurements were performed at room temperature by applying a constant stress to the sample. Rheological measurements were conducted on samples with protein concentrations ranging from 5 to 30 mg/ml.

AFM images of the dried hydrogels indicate that the nanofibers are approximately 3 nm in diameter and appear to be semiflexible, with a persistence length on the same order of magnitude as their length (FIG. 12). Many of the nanofibers also appear to have a branched structure. From the AFM images it could not be determined, if the branch-like structures are physical branches in each polymer fiber or are a result of nanofiber bundling.

Similar to most concentrated polymer networks the hydrogel of recombinant $C_{16}$ spider silk protein demonstrates viscoelastic behavior. When a stress is applied to the viscoelastic $C_{16}$ silk networks the strain changes slowly with time and is proportional to the applied stress. FIG. 14 shows the stress/strain behavior of the crosslinked and non-crosslinked hydrogels at a concentration of 10 mg/ml. The non-crosslinked $C_{16}$ silk hydrogel has an initial shear modulus of 38 Pa. However, as stress is increased the non-crosslinked hydrogel shows a higher deformation response to stress, and after a strain of 20% the response is relatively linear. With increasing stress the network continues to deform until a strain of 90% is reached, where the non-crosslinked hydrogel ruptures and flows. Unlike the non-crosslinked fiber networks, the crosslinked networks show a linear viscoelastic response over all strains, has a much higher shear modulus of 820 Pa, and ruptures at a lower strain of 30%.

Dynamic viscoelastic measurements of the non-crosslinked fiber networks at a polymer concentration of 20 mg/ml reveal that the storage modulus (G') and the loss modulus (G") are very dependent on the oscillation frequency ($\omega$) in both the high w and low w range (FIG. 15). The network demonstrates viscous behavior at low frequencies and elastic behavior at moderate frequencies with a crossover at 0.49 Hz. The observed behavior of the hydrogel is similar to that expected for an entangled polymer network and not similar to what would be expected from a liquid crystalline solution or viscous fluid.

The non-crosslinked $C_{16}$ silk hydrogel also displays dynamic viscoelastic behavior that is much different than that which is observed in the chemically crosslinked hydrogels (FIG. 15). Unlike the behavior of the non-crosslinked fiber network, the storage modulus of the crosslinked fiber network is nearly constant at all frequencies, except at the highest frequencies tested. The crosslinked $C_{16}$ silk hydrogel also demonstrates a higher storage and lower loss modulus than that which is observed in the non-crosslinked network.

As would be expected, the storage modulus of the crosslinked hydrogel is higher than that of the non-crosslinked network for all concentrations tested (FIG. 16). However, unexpectedly the storage moduli of both crosslinked and non-crosslinked networks increase with concentration [c] and have a $[c]^2$ dependence. In the case of crosslinked linear semiflexible biopolymer networks, where the persistence length is larger than the mesh size, the storage modulus of the polymer network is expected to have a dependence of [c], which is close to that of the crosslinked $C_{16}$ silk hydrogel. In the case of linear semiflexible biopolymer networks that are entangled but not crosslinked, the storage modulus is expected to have a much lower concentration dependence of [c]. Such a dependency has been shown to be valid for other biopolymers such as F-actin, but does not describe the dependency of the non-crosslinked silk hydrogel.

This discrepancy could be explained if the branch-like structures observed in the AFM images are real physical branches in the polymer network. The storage modulus of a branched semiflexible polymer network would be expected to show a concentration dependency between what would be expected for the crosslinked and non-crosslinked polymer network.

The AFM images and rheology data is consistent with from the model of a branched semiflexible polymer network. However, the storage modulus scaling behavior of the hydrogels can not be explained within the framework of the most widely excepted models for linear semiflexible polymer networks.

TABLE 1

Selected properties of synthetic silk constructs and authentic spider silk proteins ADF-3 and ADF-4.

| | $QAQ_8$ | $AQ_{12}$ | $C_{16}$ | NR3 | NR4 | $QAQ_8NR3$ | $AQ_{12}NR3$ | $C_{16}NR4$ | ADF-3 | ADF-4 |
|---|---|---|---|---|---|---|---|---|---|---|
| molecular mass [kDa][a] | 47.5 | 48.1 | 47.7 | 13.3 | 11.9 | 59.3 | 59.8 | 58.1 | 56.1 | 34.9 |
| extinction coefficient (276 nm) [$M^{-1} cm^{-1}$][b] | 23200 | 34800 | 46400 | 4423 | 1523 | 27550 | 39150 | 47850 | n.d. | n.d. |
| charged amino acid residues[c] (positive/negative) | 0/0 | 0/0 | 0/16 | 2/2 | 2/2 | 2/2 | 2/2 | 2/18 | 4/2 | 3/6 |
| grand average of hydropathicity (GRAVY)[d] | -1.252 | -0.987 | -0.464 | 0.401 | 0.438 | -0.918 | -0.710 | -0.294 | -0.628 | -0.075 |
| normalized hydropathicity and "boundary" mean hydropathicity[e] | 0.361 0.413 | 0.390 0.413 | 0.448 0.440 | 0.545 0.413 | 0.548 0.413 | n.d. | n.d. | n.d. | 0.399 0.415 | 0.464 0.417 |
| midpoint temperature of thermal unfolding[f] | no | no | no | n.d. | n.d. | 67° C. | 66° C. | 72° C. | n.d. | n.d. |
| solubility (w/v)[g] | >30% | >30% | 8% | n.d. | n.d. | >30% | >30% | 7% | >30% | <1% | aMolecular mass of engineered proteins includes the T7-tag.

bExtinction coefficients were calculated according to Gill & Hippel (23).

cCharged amino acid residues refer to silk gene sequences only;

T7-tags comprise an additional arginine.

d Hydropathicity was calculated as described previously (39). Hydrophobicity increases with hydropathicity values.

eHydropathicity was normalized to a range between 0 and 1. "Boundary" hydropathicity was calculated according to Uversky et al. (35; 36). If normalized hydropathicity values are below the "boundary" value proteins are predicted to be intrinsically unfolded. Values of ADF-3 and ADF-4 refer to their repetitive sequences only.

fMidpoint temperatures were determined by CD spectroscopy.

gValues for ADF-3 and ADF-4 were taken from (18) and unpublished results.

TABLE 2

Solubility of protein films in denaturants.

| | water | 8 M urea | 6 M guanidinium hydrochloride | 6 M guanidinium thiocyanate |
|---|---|---|---|---|
| (AQ)$_{24}$NR3 as-cast | + | + | + | + |
| (AQ)$_{24}$NR3 processed | − | + | + | + |
| C$_{16}$ as-cast | + | + | + | + |
| C$_{16}$ processed | − | − | − | + |

Films were regarded to be insoluble (−), in case complete immersion in the respective agent and repeated shaking over a period of five minutes did not result in a change of optical appearance. In contrast, solubility (+) was marked by the complete disintegration of the film under the same conditions.

REFERENCES

1. Gosline, J. M., Guerette, P. A., Ortlepp, C. S., and Savage, K. N. (1999) The mechanical design of spider silks: from fibroin sequence to mechanical function, *J. Exp. Biol.* 202 Pt 23, 3295-3303.
2. Vollrath, F. and Knight, D. P. (2001) Liquid crystalline spinning of spider silk, *Nature* 410, 541-548.
3. Guerette, P. A., Ginzinger, D. G., Weber, B. H., and Gosline, J. M. (1996) Silk properties determined by gland-specific expression of a spider fibroin gene family, *Science* 272, 112-115.
4. Gatesy, J., Hayashi, C., Motriuk, D., Woods, J., and Lewis, R. (2001) Extreme diversity, conservation, and convergence of spider silk fibroin sequences, *Science* 291, 2603-2605.
5. Simmons, A. H., Ray, E., and Jelinski, L. W. (1994) Solid-State $^{13}$C NMR of *Nephila clavipes* Dragline Silk Establishes Structure and Identity of Crystalline Regions, *Macromolecules* 27, 5235-5237.
6. Parkhe, A. D., Seeley, S. K., Gardner, K., Thompson, L., and Lewis, R. V. (1997) Structural studies of spider silk proteins in the fiber, *J. Mol. Recognit.* 10, 1-6.
7. van Beek, J. D., Hess, S., Vollrath, F., and Meier, B. H. (2002) The molecular structure of spider dragline silk: folding and orientation of the protein backbone, *Proc. Natl. Acad. Sci. U.S.A* 99, 10266-10271.
8. Hijirida, D. H., Do, K. G., Michal, C., Wong, S., Zax, D., and Jelinski, L. W. (1996) $^{13}$C NMR of *Nephila clavipes* major ampullate silk gland, *Biophys. J.* 71, 3442-3447.
9. Kenney, J. M., Knight, D., Wise, M. J., and Vollrath, F. (2002) Amyloidogenic nature of spider silk, *Eur. J. Biochem.* 269, 4159-4163.
10. Hronska, M., van Beek, J. D., Williamson, P. T., Vollrath, F., and Meier, B. H. (2004) NMR characterization of native liquid spider dragline silk from *Nephila edulis*, *Biomacromolecules.* 5, 834-839.
11. Kerkam, K., Viney, C., Kaplan, D., and Lombardi, S. (1991) Liquid crystallinity of natural silk secretions, *Nature* 349, 596-598.
12. Knight, D. P. and Vollrath, F. (1999) Liquid crystals and flow elongation in a spider's silk production line, *Proc. R. Soc. Lond.* 519-523.
13. Willcox, J., Gido, S., Muller, W., and Kaplan, D. (1996) Evidence of a Cholesteric Liquid Crystalline Phase in Natural Silk Spinning Processes, *Macromolecules* 29, 5106-5110.
14. Knight, D. P. and Vollrath, F. (2001) Changes in element composition along the spinning duct in a Nephila spider, *Naturwissenschaften* 88, 179-182.
15. Vollrath, F., Knight, D., and Hu, X. W. (1998) Silk production in a spider involves acid bath treatment, *Proc. R. Soc. Lond B Biol. Sci.* 265, 817-820.
16. Tillinghast, E. K., Chase, S. F., and Townley, M. A. (1984) Water extraction by the major ampullate duct during silk formation in the spider, *Argiope aurantia* Lucas, *J. Insect Physiol.* 30, 591-596.
17. Knight, D. P., Knight, M. M., and Vollrath, F. (2000) Beta transition and stress-induced phase separation in the spinning of spider dragline silk, *Int. J. Biol. Macromol.* 27, 205-210.
18. Lazaris, A., Arcidiacono, S., Huang, Y., Zhou, J. F., Duguay, F., Chretien, N., Welsh, E. A., Soares, J. W., and Karatzas, C. N. (2002) Spider silk fibers spun from soluble recombinant silk produced in mammalian cells, *Science* 295, 472-476.
19. Sambrook, J. and Russell, D. (2001) *Molecular Cloning.*
20. Kroll, D. J., Abdel-Malek Abdel-Hafiz, H., Marcell, T., Simpson, S., Chen, C. Y., Gutierrez-Hartmann, A., Lustbader, J. W., and Hoeffler, J. P. (1993) A multifunctional prokaryotic protein expression system: overproduction, affinity purification, and selective detection, *DNA Cell Biol.* 12, 441-453.
21. Reiling, H. E., Laurila, H., and Fiechter, A. (1985) Mass-Culture of *Escherichia*-Coli—Medium Development for Low and High-Density Cultivation of *Escherichia Coli*-B/R in Minimal and Complex Media, *Journal of Biotechnology* 2, 191-206.
22. Yee, L. and Blanch, H. W. (1992) Recombinant protein expression in high cell density fed-batch cultures of *Escherichia coli*, *Biotechnology* (N.Y.) 10, 1550-1556.
23. Gill, S. C. and von Hippel, P. H. (1989) Calculation of Protein Extinction Coefficients from Amino-Acid Sequence Data, *Analytical Biochemistry* 182, 319-326.
24. Arcidiacono, S., Mello, C., Kaplan, D., Cheley, S., and Bayley, H. (1998) Purification and characterization of recombinant spider silk expressed in *Escherichia coli*, *Appl. Microbiol. Biotechnol.* 49, 31-38.
25. Prince, J. T., McGrath, K. P., DiGirolamo, C. M., and Kaplan, D. L. (1995) Construction, cloning, and expression of synthetic genes encoding spider dragline silk, *Biochemistry* 34, 10879-10885.
26. Fahnestock, S. R. and Irwin, S. L. (1997) Synthetic spider dragline silk proteins and their production in *Escherichia coli*, *Appl. Microbiol. Biotechnol.* 47, 23-32.
27. Lewis, R. V., Hinman, M., Kothakota, S., and Fournier, M. J. (1996) Expression and purification of a spider silk protein: a new strategy for producing repetitive proteins, *Protein Expr. Pur* 7, 400-406.
28. Scheller, J., Guhrs, K. H., Grosse, F., and Conrad, U. (2001) Production of spider silk proteins in tobacco and potato, *Nat. Biotechnol.* 19, 573-577.
29. Padgett, K. A. and Sorge, J. A. (1996) Creating seamless junctions independent of restriction sites in PCR cloning, *Gene* 168, 31-35.
30. Blattner, F. R., Plunkett, G., III, Bloch, C. A., Perna, N. T., Burland, V., Riley, M., Collado-Vides, J., Glasner, J. D., Rode, C. K., Mayhew, G. F., Gregor, J., Davis, N. W., Kirkpatrick, H. A., Goeden, M. A., Rose, D. J., Mau, B., and Shao, Y. (1997) The complete genome sequence of *Escherichia coli* K-12, *Science* 277, 1453-1474.
31. Kim, T. D., Ryu, H. J., Cho, H. I., Yang, C. H., and Kim, J. (2000) Thermal behavior of proteins: heat-resistant proteins and their heat-induced secondary structural changes, *Biochemistry* 39, 14839-14846.
32. Uversky, V. N., Lee, H. J., Li, J., Fink, A. L., and Lee, S. J. (2001) Stabilization of partially folded conformation during alpha-synuclein oligomerization in both purified and cytosolic preparations, *J. Biol. Chem.* 276, 43495-43498.
33. Knight, D. P. and Vollrath, F. (2002) Biological liquid crystal elastomers, *Philos. Trans. R. Soc. Lond B Biol. Sci.* 357, 155-163.
34. Chen, X., Knight, D. P., and Vollrath, F. (2002) Rheological characterization of *nephila* spidroin solution, *Biomacromolecules.* 3, 644-648.
35. Uversky, V. N., Gillespie, J. R., and Fink, A. L. (2000) Why are "natively unfolded" proteins unstructured under physiologic conditions?, *Proteins* 41, 415-427.
36. Uversky, V. N. (2002) Natively unfolded proteins: a point where biology waits for physics, *Protein Sci.* 11, 739-756.
37. Arakawa, T. and Timasheff, S. N. (1985) Theory of protein solubility, *Methods Enzymol.* 114, 49-77.
38. Sponner, A., Unger, E., Grosse, F., and Weisshart, K. (2004) Conserved C-termini of Spidroins are secreted by the major ampullate glands and retained in the silk thread, *Biomacromolecules.* 5, 840-845.
39. Kyte, J. and Doolittle, R. F. (1982) A simple method for displaying the hydropathic character of a protein, *J. Mol. Biol.* 157, 105-132.
40. Huemmerich, D., Helsen, C. W., Oschmann, J., Rudolph, R. and Scheibel, T. (2004) Primary structure elements of dragline silks and their contribution to protein solubility and assembly, *Biochemistry* 43, 13604-13612.

The invention claimed is:

1. A recombinant spider silk protein comprising one or more synthetic repetitive spider silk protein sequences, wherein the synthetic repetitive sequence comprises between 5 to 50 repeat units, and wherein
   (i) the repeat unit consists of the amino acid sequence of SEQ ID NO: 3 (module A) or variants thereof,
   (ii) the repeat unit consists of the amino acid sequence of SEQ ID NO: 4 (module Q) or variants thereof,
   (iii) the repeat unit consists of the amino acid sequence of SEQ ID NO: 3 (module A) or variants thereof and is combined with the repeat unit consisting of the amino acid sequence of SEQ ID NO: 4 (module Q) or variants thereof, or
   (iv) the repeat unit consists of the amino acid sequence of SEQ ID NO: 4 (module Q) or variants thereof and is combined with the repeat unit consisting of the amino acid sequence of SEQ ID NO: 3 (module A) or variants thereof and is combined with the repeat unit consisting of the amino acid sequence of SEQ ID NO: 4 (module Q) or variants thereof,
wherein the variants in each case have up to 5 amino acid substitutions, deletions, insertions, and/or additions, which do not negatively affect tensile strength and elasticity of a thread formed from the recombinant spider silk protein.

2. The recombinant spider silk protein of claim 1, wherein the synthetic repetitive sequence is $(AQ)_{12}$, $(AQ)_{24}$, $(QAQ)_8$ or $(QAQ)_{16}$.

3. A method of aggregation of spider silk proteins, comprising the following steps:
   a) preparing a protein solution containing unoriented spider silk proteins as defined in claim 1;
   b) exposing the solution prepared in a) to an aggregation trigger; and
   c) recovering the precipitated spider silk proteins.

4. The method of claim 3, wherein the aggregation trigger is selected from acidification, potassium phosphate and mechanical stress.

5. The method of claim 3, which further comprises the step of spinning said proteins provided in step a) or recovered in step c) into filaments, nanofibers and threads by a suitable method or forming a film.

6. A method for closing a wound or for providing a replacement material to a wound, comprising employing the recombinant spider silk protein of claim 1 to close a wound or to provide a replacement material to a wound.

7. A method for the manufacture of wound closure or coverage systems, comprising employing the recombinant spider silk protein of claim 1.

8. The method of claim 7, wherein the wound closure system comprises suture materials.

9. The method of claim 8, wherein the suture materials comprise neurosurgery or ophthalmic surgery suture materials.

10. A method for the manufacture of replacement materials, comprising employing the recombinant spider silk protein of claim 1.

11. A method for the manufacture of automotive and aircraft parts, comprising employing the recombinant spider silk protein of claim 1.

12. Wound closure or coverage systems, suture materials, replacement materials, artificial cartilage, tendon materials, automotive parts or parts used in the aircraft construction, which comprise the protein of claim 1.

13. A recombinant spider silk protein comprising one or more authentic non-repetitive spider silk protein sequences, wherein the authentic non-repetitive sequences are selected from the group consisting of the amino acid sequence according to SEQ ID NO: 10 (NR3) devoid of the amino acid sequence of SEQ ID NO: 30 (T7-tag), the amino acid sequence according to SEQ ID NO: 11 (NR4) devoid of the amino acid sequence of SEQ ID NO: 30 (T7-tag), and variants thereof, wherein the variants in each case have up to 5 amino acid substitutions, deletions, insertions, and/or additions, which do not negatively affect tensile strength and elasticity of a thread formed form the recombinant spider silk protein.

14. The recombinant spider silk protein of claim 13, wherein the authentic non-repetitive sequence is the amino acid sequence according to SEQ ID NO: 11 (NR4) devoid of the amino acid sequence of SEQ ID NO: 30 (T7-tag).

15. The recombinant spider silk protein of claim 13, wherein the authentic non-repetitive sequence is the amino acid sequence according to SEQ ID NO: 10 (NR3) devoid of the amino acid sequence of SEQ ID NO: 30 (T7-tag).

16. A method of aggregation of spider silk proteins, comprising the following steps:
   a) preparing a protein solution containing unoriented spider silk proteins as defined in claim 13;
   b) exposing the solution prepared in a) to an aggregation trigger; and
   c) recovering the precipitated spider silk proteins.

17. The method of claim 16, wherein the aggregation trigger is selected from acidification, potassium phosphate and mechanical stress.

18. The method of claim 16, which further comprises the step of spinning said proteins provided in step a) or recovered in step c) into filaments, nanofibers and threads by a suitable method or forming a film.

19. A method for closing a wound or for providing a replacement material to a wound, comprising employing the recombinant spider silk protein of claim 13 to close a wound or to provide a replacement material to a wound.

20. A method for the manufacture of wound closure or coverage systems, comprising employing the recombinant spider silk protein of claim 13 in the preparation of wound closure or coverage systems.

21. The method of claim 20, wherein the wound closure system comprises suture materials.

22. The method of claim 21, wherein the suture materials comprise neurosurgery or ophthalmic surgery suture materials.

23. A method for the manufacture of replacement materials, comprising employing the recombinant spider silk protein of claim 13 in the preparation of replacement materials.

24. A method for the manufacture of automotive and aircraft parts, comprising employing the recombinant spider silk protein of claim 13 in the preparation of automotive and aircraft parts.

25. Wound closure or coverage systems, suture materials, replacement materials, artificial cartilage, tendon materials, automotive parts or parts used in the aircraft construction, which comprise the protein of claim 13.

26. A wound closure or coverage system, suture material, replacement material, artificial cartilage, tendon material, automotive part, or part used in aircraft construction, which comprise the protein obtained by the method of claim 16.

27. A wound closure or coverage system, suture material, replacement material, artificial cartilage, tendon material, automotive part, or part used in aircraft construction, which comprise the protein obtained by the method of claim 3.

28. The method of claim 4, wherein acidification is to a pH of about 1, and mechanical stress is rotating the protein solution and applying shearing forces.

29. The method of claim 17, wherein acidification is to a pH of about 1, and mechanical stress is rotating the protein solution and applying shearing forces.

* * * * *

SEQUENCE LISTING

```
<160> NUMBER OF SEQ ID NOS: 55

<210> SEQ ID NO 1
<211> LENGTH: 653
<212> TYPE: PRT
<213> ORGANISM: Araneus diadematus

<400> SEQUENCE: 1

Met Ala Ser Met Thr Gly Gly Gln Gln Met Gly Arg Asp Pro Asn Ser
1               5                   10                  15

Ala Arg Ala Gly Ser Gln Gln Gly Pro Gly Gln Gln Gly Pro Gly
            20                  25                  30

Gln Gln Gly Pro Gly Gln Gln Gly Pro Tyr Gly Pro Gly Ala Ser Ala
        35                  40                  45

Ala Ala Ala Ala Ala Gly Gly Tyr Gly Pro Gly Ser Gly Gln Gln Gly
    50                  55                  60

Pro Ser Gln Gln Gly Pro Gly Gln Gln Gly Pro Gly Gly Gln Gly Pro
65                  70                  75                  80

Tyr Gly Pro Gly Ala Ser Ala Ala Ala Ala Ala Gly Gly Tyr Gly
                85                  90                  95

Pro Gly Ser Gly Gln Gln Gly Pro Gly Gln Gln Gly Pro Tyr Gly Pro
            100                 105                 110

Gly Ser Ser Ala Ala Ala Ala Ala Gly Gly Asn Gly Pro Gly Ser
        115                 120                 125

Gly Gln Gln Gly Pro Gly Gln Gln Gly Pro Gly Gln Gln Gly Pro Gly
    130                 135                 140

Ala Ser Ala Ala Ala Ala Ala Gly Gly Tyr Gly Pro Gly Ser Gly
145                 150                 155                 160

Gln Gln Gly Pro Gly Gln Gln Gly Pro Gly Gly Gln Gly Pro Tyr Gly
                165                 170                 175

Pro Gly Ala Ser Ala Ala Ala Ala Ala Gly Gly Tyr Gly Pro Gly
            180                 185                 190

Ser Gly Gln Gln Gly Pro Gly Gln Gln Gly Pro Gly Gln Gly Pro
        195                 200                 205

Tyr Gly Pro Gly Ala Ser Ala Ala Ala Ala Ala Gly Gly Tyr Gly
    210                 215                 220

Pro Gly Ser Gly Gln Gln Gly Pro Gly Gln Gln Gly Pro Gly Gln Gln
225                 230                 235                 240

Gly Pro Gly Gly Gln Gly Pro Tyr Gly Pro Gly Ala Ser Ala Ala Ala
                245                 250                 255

Ala Ala Ala Gly Gly Tyr Gly Pro Gly Tyr Gly Gln Gln Gly Pro Gly
            260                 265                 270
```

Gln Gln Gly Pro Gly Gly Gln Gly Pro Tyr Gly Pro Gly Ala Ser Ala
            275                 280                 285

Ala Ser Ala Ala Ser Gly Gly Tyr Gly Pro Gly Ser Gly Gln Gln Gly
        290                 295                 300

Pro Gly Gln Gln Gly Pro Gly Gly Gln Gly Pro Tyr Gly Pro Gly Ala
305                 310                 315                 320

Ser Ala Ala Ala Ala Ala Gly Gly Tyr Gly Pro Gly Ser Gly Gln
                325                 330                 335

Gln Gly Pro Gly Gln Gln Gly Pro Gly Gln Gln Gly Pro Gly Gln Gln
            340                 345                 350

Gly Pro Gly Gly Gln Gly Pro Tyr Gly Pro Gly Ala Ser Ala Ala Ala
            355                 360                 365

Ala Ala Ala Gly Gly Tyr Gly Pro Gly Ser Gln Gln Gly Pro Gly
        370                 375                 380

Gln Gln Gly Pro Gly Gln Gln Gly Pro Gly Gln Gln Gly Pro Gly Gln
385                 390                 395                 400

Gln Gly Pro Gly Gln Gln Gly Pro Gly Gln Gln Gly Pro Gly Gln Gln
            405                 410                 415

Gly Pro Gly Gln Gln Gly Pro Gly Gly Gln Gly Ala Tyr Gly Pro Gly
            420                 425                 430

Ala Ser Ala Ala Ala Gly Ala Ala Gly Gly Tyr Gly Pro Gly Ser Gly
        435                 440                 445

Gln Gln Gly Pro Gly Gln Gln Gly Pro Gly Gln Gln Gly Pro Gly Gln
            450                 455                 460

Gln Gly Pro Gly Gln Gln Gly Pro Gly Gln Gln Gly Pro Gly Gln Gln
465                 470                 475                 480

Gly Pro Gly Gln Gln Gly Pro Tyr Gly Pro Gly Ala Ser Ala Ala Ala
                485                 490                 495

Ala Ala Ala Gly Gly Tyr Gly Pro Gly Ser Gly Gln Gln Gly Pro Gly
        500                 505                 510

Gln Gln Gly Pro Gly Gln Gln Gly Pro Val Gly Gln Gly Pro Tyr Gly
            515                 520                 525

Pro Gly Ala Ala Ser Ala Ala Val Ser Val Gly Gly Tyr Gly Pro Gln
        530                 535                 540

Ser Ser Ser Ala Pro Val Ala Ser Ala Ala Ser Arg Leu Ser Ser
545                 550                 555                 560

Pro Ala Ala Ser Ser Arg Val Ser Ser Ala Val Ser Ser Leu Val Ser
                565                 570                 575

Ser Gly Pro Thr Asn Gln Ala Ala Leu Ser Asn Thr Ile Ser Ser Val
        580                 585                 590

Val Ser Gln Val Ser Ala Ser Asn Pro Gly Leu Ser Gly Cys Asp Val
            595                 600                 605

Leu Val Gln Ala Leu Leu Glu Val Val Ser Ala Leu Val Ser Ile Leu
            610                 615                 620

Gly Ser Ser Ser Ile Gly Gln Ile Asn Tyr Gly Ala Ser Ala Gln Tyr
625                 630                 635                 640

Thr Gln Met Val Gly Gln Ser Val Ala Gln Ala Leu Ala
                645                 650

<210> SEQ ID NO 2
<211> LENGTH: 671
<212> TYPE: PRT
<213> ORGANISM: Araneus diadematus

```
<400> SEQUENCE: 2

Met Ala Ser Met Thr Gly Gly Gln Gln Met Gly Arg Ala Ala Arg Ala
1               5                   10                  15

Gly Ser Ser Ala Ala Ala Ala Ala Ala Ser Gly Ser Gly Gly Tyr
            20                  25                  30

Gly Pro Glu Asn Gln Gly Pro Ser Gly Pro Val Ala Tyr Gly Pro Gly
            35                  40                  45

Gly Pro Val Ser Ser Ala Ala Ala Ala Ala Ala Gly Ser Gly Pro
        50                  55                  60

Gly Gly Tyr Gly Pro Glu Asn Gln Gly Pro Ser Gly Pro Gly Gly Tyr
65                  70                  75                  80

Gly Pro Gly Gly Ser Gly Ser Ser Ala Ala Ala Ala Ala Ala Ala Ala
                85                  90                  95

Ser Gly Pro Gly Gly Tyr Gly Pro Gly Ser Gln Gly Pro Ser Gly Pro
            100                 105                 110

Gly Gly Ser Gly Gly Tyr Gly Pro Gly Ser Gln Gly Pro Ser Gly Pro
            115                 120                 125

Gly Ala Ser Ala Ala Ala Ala Ala Ala Ser Gly Pro Gly
            130                 135                 140

Gly Tyr Gly Pro Gly Ser Gln Gly Pro Ser Gly Pro Gly Ala Tyr Gly
145                 150                 155                 160

Pro Gly Gly Pro Gly Ser Ser Ala Ala Ala Ser Gly Pro Gly Tyr
                165                 170                 175

Gly Pro Gly Ser Gln Gly Pro Ser Gly Pro Gly Gly Ser Gly Gly Tyr
            180                 185                 190

Gly Pro Gly Ser Gln Gly Pro Ser Gly Pro Gly Gly Pro Gly Ala Ser
            195                 200                 205

Ala Ala Ala Ala Ala Ala Ala Ser Gly Pro Gly Gly Tyr Gly
210                 215                 220

Pro Gly Ser Gln Gly Pro Ser Gly Pro Gly Ala Tyr Gly Pro Gly Gly
225                 230                 235                 240

Pro Gly Ser Ser Ala Ala Ala Ser Gly Pro Gly Gly Tyr Gly Pro Gly
                245                 250                 255

Ser Gln Gly Pro Ser Gly Pro Gly Ala Tyr Gly Pro Gly Gly Pro Gly
            260                 265                 270

Ser Ser Ala Ala Ala Ala Ala Gly Ser Gly Pro Gly Gly Tyr
            275                 280                 285

Gly Pro Gly Asn Gln Gly Pro Ser Gly Pro Gly Gly Tyr Gly Pro Gly
            290                 295                 300

Gly Pro Gly Ser Ser Ala Ala Ala Ala Ala Ala Ser Gly Pro Gly
305                 310                 315                 320

Gly Tyr Gly Pro Gly Ser Gln Gly Pro Ser Gly Pro Gly Val Tyr Gly
            325                 330                 335

Pro Gly Gly Pro Gly Ser Ser Ala Ala Ala Ala Ala Ala Gly Ser
            340                 345                 350

Gly Pro Gly Gly Tyr Gly Pro Gly Asn Gln Gly Pro Ser Gly Pro Gly
            355                 360                 365

Gly Tyr Gly Pro Gly Gly Ser Gly Ser Ser Ala Ala Ala Ala Ala
            370                 375                 380

Ala Ala Ser Gly Pro Gly Gly Tyr Gly Pro Gly Ser Gln Gly Pro Ser
385                 390                 395                 400

Gly Pro Gly Gly Ser Gly Gly Tyr Gly Pro Gly Ser Gln Gly Pro Ser
            405                 410                 415
```

```
Gly Pro Gly Ala Ser Ser Ala Ala Ala Ala Ala Ala Ala Ser Gly
                420                 425                 430

Pro Gly Gly Tyr Gly Pro Gly Ser Gln Gly Pro Ser Pro Gly Ala
            435                 440                 445

Tyr Gly Pro Gly Gly Pro Gly Ser Ser Ala Ala Ala Ser Pro Gly
450                 455                 460

Gly Tyr Gly Pro Gly Ser Gln Gly Pro Ser Gly Pro Gly Ala Tyr Gly
465                 470                 475                 480

Pro Gly Gly Pro Gly Ser Ser Ala Ala Ala Ala Ala Ala Ser Gly
            485                 490                 495

Pro Gly Gly Tyr Gly Pro Gly Ser Gln Gly Pro Ser Gly Pro Gly Gly
                500                 505                 510

Ser Arg Gly Tyr Gly Pro Gly Ser Gln Gly Pro Gly Gly Pro Gly Ala
            515                 520                 525

Ser Ala Ala Ala Ala Ala Ala Ala Ala Ser Gly Pro Gly Gly Tyr
    530                 535                 540

Gly Pro Gly Ser Gln Gly Pro Ser Gly Pro Gly Tyr Gln Gly Pro Ser
545                 550                 555                 560

Gly Pro Gly Ala Tyr Gly Pro Ser Pro Ser Ala Ser Ala Ser Val Ala
                565                 570                 575

Ala Ser Arg Leu Ser Ser Pro Ala Ala Ser Ser Arg Val Ser Ser Ala
            580                 585                 590

Val Ser Ser Leu Val Ser Ser Gly Pro Thr Asn Gly Ala Ala Val Ser
            595                 600                 605

Gly Ala Leu Asn Ser Leu Val Ser Gln Ile Ser Ala Ser Asn Pro Gly
            610                 615                 620

Leu Ser Gly Cys Asp Ala Leu Val Gln Ala Leu Leu Glu Leu Val Ser
625                 630                 635                 640

Ala Leu Val Ala Ile Leu Ser Ser Ala Ser Ile Gly Gln Val Asn Val
                645                 650                 655

Ser Ser Val Ser Gln Ser Thr Gln Met Ile Ser Gln Ala Leu Ser
            660                 665                 670

<210> SEQ ID NO 3
<211> LENGTH: 24
<212> TYPE: PRT
<213> ORGANISM: Artificial sequence
<220> FEATURE:
<223> OTHER INFORMATION: Module A (ADF-3)

<400> SEQUENCE: 3

Gly Pro Tyr Gly Pro Gly Ala Ser Ala Ala Ala Ala Ala Ala Gly Gly
1               5                   10                  15

Tyr Gly Pro Gly Ser Gly Gln Gln
            20

<210> SEQ ID NO 4
<211> LENGTH: 20
<212> TYPE: PRT
<213> ORGANISM: Artificial sequence
<220> FEATURE:
<223> OTHER INFORMATION: Module Q (ADF-3)

<400> SEQUENCE: 4

Gly Pro Gly Gln Gln Gly Pro Gly Gln Gln Gly Pro Gly Gln Gln Gly
1               5                   10                  15

Pro Gly Gln Gln
            20
```

```
<210> SEQ ID NO 5
<211> LENGTH: 35
<212> TYPE: PRT
<213> ORGANISM: Artificial sequence
<220> FEATURE:
<223> OTHER INFORMATION: Module C (ADF-4)

<400> SEQUENCE: 5

Gly Ser Ser Ala Ala Ala Ala Ala Ala Ala Ser Gly Pro Gly Gly
1               5                   10                  15

Tyr Gly Pro Glu Asn Gln Gly Pro Ser Gly Pro Gly Gly Tyr Gly Pro
            20                  25                  30

Gly Gly Pro
        35

<210> SEQ ID NO 6
<211> LENGTH: 942
<212> TYPE: PRT
<213> ORGANISM: Nephila clavipes

<400> SEQUENCE: 6

Ala Cys Phe Thr Ser Ala Val Ile Phe Leu Phe Leu Ala Gln Cys Ala
1               5                   10                  15

Ser Thr Tyr Gly Arg Gly Ile Ile Ala Asn Ser Pro Phe Ser Asn Pro
            20                  25                  30

Asn Thr Ala Glu Ala Phe Ala Arg Ser Phe Val Ser Asn Ile Val Ser
        35                  40                  45

Ser Gly Glu Phe Gly Ala Gln Gly Ala Glu Asp Phe Asp Asp Ile Ile
    50                  55                  60

Gln Ser Leu Ile Gln Ala Gln Ser Met Gly Lys Gly Arg His Asp Thr
65                  70                  75                  80

Lys Ala Lys Ala Lys Ala Met Gln Val Ala Leu Ala Ser Ser Ile Ala
                85                  90                  95

Glu Leu Val Ile Ala Glu Ser Ser Gly Gly Asp Val Gln Arg Lys Thr
            100                 105                 110

Asn Val Ile Ser Asn Ala Leu Arg Asn Ala Leu Met Ser Thr Thr Gly
        115                 120                 125

Ser Pro Asn Glu Glu Phe Val His Glu Val Gln Asp Leu Ile Gln Met
    130                 135                 140

Leu Ser Gln Glu Gln Ile Asn Glu Val Asp Thr Ser Gly Pro Gly Gln
145                 150                 155                 160

Tyr Tyr Arg Ser Ser Ser Gly Gly Gly Gly Gly Gln Gly Gly
                165                 170                 175

Pro Val Val Thr Glu Thr Leu Thr Val Thr Val Gly Gly Ser Gly Gly
            180                 185                 190

Gly Gln Pro Ser Gly Ala Gly Pro Ser Gly Thr Gly Gly Tyr Ala Pro
        195                 200                 205

Thr Gly Tyr Ala Pro Ser Gly Ser Gly Ala Gly Val Arg Pro Ser
    210                 215                 220

Ala Ser Gly Pro Ser Gly Ser Gly Pro Ser Gly Ser Arg Pro Ser
225                 230                 235                 240

Ser Ser Gly Pro Ser Gly Thr Arg Pro Ser Pro Asn Gly Ala Ser Gly
                245                 250                 255

Ser Ser Pro Gly Gly Ile Ala Pro Gly Gly Ser Asn Ser Gly Gly Ala
            260                 265                 270

Gly Val Ser Gly Ala Thr Gly Gly Pro Ala Ser Ser Gly Ser Tyr Gly
        275                 280                 285
```

-continued

```
Pro Gly Ser Thr Gly Gly Thr Tyr Gly Pro Ser Gly Ser Glu Pro
        290                 295                 300

Phe Gly Pro Gly Val Ala Gly Gly Pro Tyr Ser Pro Gly Gly Ala Gly
305                 310                 315                 320

Pro Gly Gly Ala Gly Gly Ala Tyr Gly Pro Gly Gly Val Gly Thr Gly
                325                 330                 335

Gly Ala Gly Pro Gly Gly Tyr Gly Pro Gly Gly Ala Gly Pro Gly Gly
            340                 345                 350

Tyr Gly Pro Gly Gly Ala Gly Pro Gly Gly Tyr Gly Pro Gly Gly Ala
        355                 360                 365

Gly Pro Gly Gly Tyr Gly Pro Gly Gly Ala Gly Pro Gly Gly Tyr Gly
    370                 375                 380

Pro Gly Gly Ala Gly Pro Gly Gly Tyr Gly Pro Gly Gly Ala Gly Pro
385                 390                 395                 400

Gly Gly Tyr Gly Pro Gly Gly Thr Gly Pro Gly Gly Tyr Gly Pro Gly
                405                 410                 415

Gly Thr Gly Pro Gly Gly Val Gly Pro Gly Gly Ala Gly Pro Gly Gly
            420                 425                 430

Tyr Gly Pro Gly Gly Ala Gly Pro Gly Gly Ala Gly Pro Gly Gly Ala
        435                 440                 445

Gly Pro Gly Gly Ala Gly Pro Gly Gly Ala Gly Pro Gly Gly Ala Gly
    450                 455                 460

Pro Gly Gly Tyr Gly Pro Gly Gly Ser Gly Pro Gly Gly Ala Gly Pro
465                 470                 475                 480

Ser Gly Ala Gly Leu Gly Gly Ala Gly Pro Gly Gly Ala Gly Leu Gly
                485                 490                 495

Gly Ala Gly Pro Gly Gly Ala Gly Thr Ser Gly Ala Gly Pro Gly Gly
            500                 505                 510

Ala Gly Pro Gly Gly Ala Gly Gln Gly Asp Ala Gly Pro Gly Gly Ala
        515                 520                 525

Gly Arg Gly Gly Ala Gly Arg Gly Gly Val Gly Arg Gly Gly Ala Gly
    530                 535                 540

Arg Gly Gly Ala Gly Arg Gly Gly Ala Arg Gly Ala Gly Gly Ala Gly
545                 550                 555                 560

Gly Ala Gly Gly Ala Gly Gly Ser Gly Gly Thr Thr Ile Val Glu Asp
                565                 570                 575

Leu Asp Ile Thr Ile Asp Gly Ala Asp Gly Pro Ile Thr Ile Ser Glu
            580                 585                 590

Glu Leu Thr Ile Gly Gly Ala Gly Ala Gly Gly Ser Gly Pro Gly Gly
        595                 600                 605

Ala Gly Pro Gly Asn Val Gly Pro Gly Arg Ser Gly Pro Gly Gly Val
    610                 615                 620

Gly Pro Gly Gly Ser Gly Pro Gly Gly Val Gly Pro Gly Ser Phe Gly
625                 630                 635                 640

Pro Gly Gly Val Gly Pro Gly Gly Ser Gly Pro Gly Gly Val Gly Ser
                645                 650                 655

Gly Gly Ser Gly Gln Gly Gly Val Arg Pro Ser Gly Ser Gly Pro Gly
            660                 665                 670

Gly Val Gly Thr Gly Gly Val Gly Pro Gly Gly Ala Gly Gly Pro Tyr
        675                 680                 685

Gly Pro Gly Gly Ser Gly Pro Gly Gly Ala Gly Ser Ala Gly Gly Thr
    690                 695                 700

Tyr Gly Pro Gly Gly Phe Gly Gly Pro Gly Gly Phe Gly Gly Pro Gly
705                 710                 715                 720
```

-continued

Gly Ala Gly Gly Pro Tyr Gly Pro Gly Gly Ala Gly Pro Tyr Gly
                    725                 730                 735

Pro Gly Gly Ala Gly Gly Pro Tyr Gly Pro Gly Gly Ala Gly Pro
                740                 745                 750

Tyr Gly Pro Gly Gly Ala Gly Gly Pro Tyr Gly Pro Gly Gly Ala Gly
            755                 760                 765

Gly Ser Tyr Gly Leu Gly Gly Ala Gly Gly Ser Gly Gly Val Gly Pro
        770                 775                 780

Gly Gly Ser Gly Pro Gly Gly Tyr Gly Pro Gly Gly Ala Gly Pro Gly
785                 790                 795                 800

Gly Tyr Gly Pro Gly Gly Ser Gly Pro Gly Gly Tyr Gly Pro Gly Gly
            805                 810                 815

Ser Gly Ser Gly Gly Tyr Gly Pro Gly Gly Ser Gly Pro Gly Gly Ser
            820                 825                 830

Gly Pro Gly Gly Tyr Gly Pro Gly Gly Thr Gly Pro Gly Gly Ser Glu
            835                 840                 845

Ser Gly Gly Tyr Gly Pro Gly Gly Ser Gly Pro Gly Gly Ser Gly Pro
        850                 855                 860

Gly Gly Ser Gly Pro Gly Gly Ser Gly Pro Gly Gly Tyr Gly Pro Gly
865                 870                 875                 880

Gly Ser Gly Pro Ser Ser Phe Val Pro Gly Gly Ser Gly Pro Gly Gly
            885                 890                 895

Ser Gly Pro Gly Gly Ala Gly Pro Gly Gly Ala Gly Pro Gly Gly Val
            900                 905                 910

Gly Leu Gly Gly Ala Gly Arg Gly Gly Ala Gly Arg Gly Gly Ala Gly
        915                 920                 925

Ser Val Gly Ala Gly Arg Gly Gly Ala Gly Arg Gly Gly Thr
        930                 935                 940

<210> SEQ ID NO 7
<211> LENGTH: 907
<212> TYPE: PRT
<213> ORGANISM: Nephila clavipes

<400> SEQUENCE: 7

Gly Pro Gly Gly Val Gly Pro Gly Gly Ser Gly Pro Gly Gly Tyr Gly
1               5                   10                  15

Pro Gly Gly Ala Gly Pro Gly Gly Tyr Gly Pro Gly Gly Ser Gly Pro
                20                  25                  30

Gly Gly Tyr Gly Pro Gly Gly Ser Gly Pro Gly Gly Tyr Gly Pro Gly
            35                  40                  45

Gly Ser Gly Pro Gly Gly Tyr Gly Pro Gly Gly Ser Gly Pro Gly Gly
        50                  55                  60

Tyr Gly Pro Gly Gly Ser Gly Pro Gly Gly Tyr Gly Pro Gly Gly Tyr
65                  70                  75                  80

Gly Pro Gly Gly Ser Gly Pro Gly Gly Tyr Gly Pro Gly Gly Thr Gly
                85                  90                  95

Pro Gly Gly Ser Gly Pro Gly Gly Tyr Gly Pro Gly Gly Ser Gly Pro
            100                 105                 110

Gly Gly Ser Gly Pro Gly Gly Tyr Gly Pro Gly Gly Ser Gly Pro Gly
        115                 120                 125

Gly Phe Gly Pro Gly Gly Ser Gly Pro Gly Gly Tyr Gly Pro Gly Gly
        130                 135                 140

Ser Gly Pro Gly Gly Ala Gly Pro Gly Gly Val Gly Pro Gly Gly Phe
145                 150                 155                 160

-continued

Gly Pro Gly Gly Ala Gly Pro Gly Gly Ala Gly Pro Gly Gly Ala Gly
            165                 170                 175
Pro Gly Gly Ala Gly Pro Gly Gly Ala Gly Pro Gly Gly Ala Gly Pro
            180                 185                 190
Gly Gly Ala Gly Pro Gly Gly Ala Gly Pro Gly Gly Ala Gly Pro Gly
            195                 200                 205
Gly Ala Gly Pro Gly Gly Ala Gly Gly Ala Gly Ala Gly Gly Ala
        210                 215                 220
Gly Gly Ser Gly Gly Ala Gly Gly Ser Gly Gly Thr Thr Ile Ile Glu
225                 230                 235                 240
Asp Leu Asp Ile Thr Ile Asp Gly Ala Asp Gly Pro Ile Thr Ile Ser
            245                 250                 255
Glu Glu Leu Thr Ile Ser Gly Ala Gly Gly Ser Gly Pro Gly Gly Ala
            260                 265                 270
Gly Pro Gly Gly Val Gly Pro Gly Gly Ser Gly Pro Gly Gly Val Gly
            275                 280                 285
Pro Gly Gly Ser Gly Pro Gly Gly Val Gly Pro Gly Gly Ser Gly Pro
            290                 295                 300
Gly Gly Val Gly Pro Gly Gly Ala Gly Pro Tyr Gly Pro Gly Gly
305                 310                 315                 320
Ser Gly Pro Gly Gly Ala Gly Ala Gly Pro Gly Gly Ala Tyr
            325                 330                 335
Gly Pro Gly Gly Ser Tyr Gly Pro Gly Gly Ser Gly Gly Pro Gly Gly
            340                 345                 350
Ala Gly Gly Pro Tyr Gly Pro Gly Gly Glu Gly Pro Gly Gly Ala Gly
            355                 360                 365
Gly Pro Tyr Gly Pro Gly Gly Ala Gly Gly Pro Tyr Gly Pro Gly Gly
            370                 375                 380
Ala Gly Gly Pro Tyr Gly Pro Gly Gly Glu Gly Gly Pro Tyr Gly Pro
385                 390                 395                 400
Gly Gly Ser Tyr Gly Pro Gly Gly Ala Gly Gly Pro Tyr Gly Pro Gly
            405                 410                 415
Gly Pro Tyr Gly Pro Gly Gly Glu Gly Pro Gly Gly Ala Gly Gly Pro
            420                 425                 430
Tyr Gly Pro Gly Gly Val Gly Pro Gly Gly Ser Gly Pro Gly Gly Tyr
            435                 440                 445
Gly Pro Gly Gly Ser Gly Pro Gly Gly Tyr Gly Pro Gly Gly Ala Gly
            450                 455                 460
Pro Gly Gly Tyr Gly Pro Gly Gly Ser Gly Pro Gly Gly Tyr Gly Pro
465                 470                 475                 480
Gly Gly Ser Gly Pro Gly Gly Tyr Gly Pro Gly Gly Ser Gly Pro Gly
            485                 490                 495
Gly Tyr Gly Pro Gly Gly Ser Gly Pro Gly Gly Tyr Gly Ser Gly Gly
            500                 505                 510
Ala Gly Pro Gly Gly Tyr Gly Pro Gly Gly Ser Gly Pro Gly Gly Tyr
            515                 520                 525
Gly Pro Gly Gly Ser Gly Pro Gly Gly Tyr Gly Pro Gly Gly Thr Gly
            530                 535                 540
Pro Gly Gly Thr Gly Pro Gly Gly Ser Gly Pro Gly Gly Tyr Gly Pro
545                 550                 555                 560
Gly Gly Ser Gly Pro Gly Gly Ser Gly Pro Gly Gly Ser Gly Pro Gly
            565                 570                 575
Gly Tyr Gly Pro Ser Gly Ser Gly Pro Gly Gly Tyr Gly Pro Ser Gly
            580                 585                 590

```
Ser Gly Pro Gly Gly Tyr Gly Pro Gly Gly Ser Gly Pro Gly Gly Tyr
            595                 600                 605
Gly Pro Gly Gly Ser Gly Ala Gly Gly Thr Gly Pro Gly Gly Ala Gly
        610                 615                 620
Gly Ala Gly Gly Ala Gly Gly Ser Gly Gly Ala Gly Gly Ser Gly Gly
625                 630                 635                 640
Ala Gly Gly Ser Gly Gly Ala Gly Gly Ser Gly Gly Val Gly Gly Ser
                645                 650                 655
Gly Gly Thr Thr Ile Thr Glu Asp Leu Asp Ile Thr Ile Asp Gly Ala
        660                 665                 670
Asp Gly Pro Ile Thr Ile Ser Glu Glu Leu Thr Ile Ser Gly Ala Gly
            675                 680                 685
Gly Ser Gly Pro Gly Gly Ala Gly Pro Gly Gly Val Gly Pro Gly Gly
        690                 695                 700
Ser Gly Pro Gly Gly Val Gly Pro Gly Val Ser Gly Pro Gly Gly Val
705                 710                 715                 720
Gly Pro Gly Gly Ser Gly Pro Gly Val Gly Ser Gly Gly Ser Gly
                725                 730                 735
Pro Gly Gly Val Gly Pro Gly Gly Tyr Gly Pro Gly Gly Ser Gly Ser
            740                 745                 750
Gly Gly Val Gly Pro Gly Gly Tyr Gly Pro Gly Gly Ser Gly Gly Phe
        755                 760                 765
Tyr Gly Pro Gly Gly Ser Glu Gly Pro Tyr Gly Pro Ser Gly Thr Tyr
770                 775                 780
Gly Ser Gly Gly Gly Tyr Gly Pro Gly Ala Gly Gly Pro Tyr Gly
785                 790                 795                 800
Pro Gly Ser Pro Gly Gly Ala Tyr Gly Pro Gly Ser Pro Gly Gly Ala
            805                 810                 815
Tyr Tyr Pro Ser Ser Arg Val Pro Asp Met Val Asn Gly Ile Met Ser
            820                 825                 830
Ala Met Gln Gly Ser Gly Phe Asn Tyr Gln Met Phe Gly Asn Met Leu
        835                 840                 845
Ser Gln Tyr Ser Ser Gly Ser Gly Thr Cys Asn Pro Asn Asn Val Asn
    850                 855                 860
Val Leu Met Asp Ala Leu Leu Ala Ala Leu His Cys Leu Ser Asn His
865                 870                 875                 880
Gly Ser Ser Ser Phe Ala Pro Ser Pro Thr Pro Ala Ala Met Ser Ala
                885                 890                 895
Tyr Ser Asn Ser Val Gly Arg Met Phe Ala Tyr
            900                 905

<210> SEQ ID NO 8
<211> LENGTH: 636
<212> TYPE: PRT
<213> ORGANISM: Araneus diadematus

<400> SEQUENCE: 8

Ala Arg Ala Gly Ser Gly Gln Gln Gly Pro Gly Gln Gln Gly Pro Gly
1               5                   10                  15
Gln Gln Gly Pro Gly Gln Gln Gly Pro Tyr Gly Pro Gly Ala Ser Ala
            20                  25                  30
Ala Ala Ala Ala Ala Gly Gly Tyr Gly Pro Gly Ser Gly Gln Gln Gly
        35                  40                  45
Pro Ser Gln Gln Gly Pro Gly Gln Gln Gly Pro Gly Gly Gln Gly Pro
    50                  55                  60
```

```
Tyr Gly Pro Gly Ala Ser Ala Ala Ala Ala Gly Gly Tyr Gly
65                  70                  75                  80

Pro Gly Ser Gly Gln Gln Gly Pro Gly Gln Gly Pro Tyr Gly Pro
                85                  90                  95

Gly Ser Ser Ala Ala Ala Ala Ala Gly Gly Asn Gly Pro Gly Ser
            100                 105                 110

Gly Gln Gln Gly Ala Gly Gln Gly Pro Gly Gln Gln Gly Pro Gly
            115                 120                 125

Ala Ser Ala Ala Ala Ala Ala Gly Gly Tyr Gly Pro Gly Ser Gly
        130                 135                 140

Gln Gln Gly Pro Gly Gln Gln Gly Pro Gly Gln Gln Gly Pro Tyr Gly
145                 150                 155                 160

Pro Gly Ala Ser Ala Ala Ala Ala Ala Gly Gly Tyr Gly Pro Gly
                165                 170                 175

Ser Gly Gln Gly Pro Gly Gln Gln Gly Pro Gly Gln Gln Gly Pro Tyr
            180                 185                 190

Gly Pro Gly Ala Ser Ala Ala Ala Ala Ala Gly Gly Tyr Gly Pro
            195                 200                 205

Gly Ser Gly Gln Gln Gly Pro Gly Gln Gln Gly Pro Gly Gln Gln Gly
210                 215                 220

Pro Gly Gln Gly Pro Tyr Gly Pro Gly Ala Ser Ala Ala Ala Ala
225                 230                 235                 240

Ala Ala Gly Gly Tyr Gly Pro Gly Tyr Gly Gln Gly Pro Gly Gln
                245                 250                 255

Gln Gly Pro Gly Gln Gly Pro Tyr Gly Pro Gly Ala Ser Ala Ala
            260                 265                 270

Ser Ala Ala Ser Gly Gly Tyr Gly Pro Gly Ser Gly Gln Gln Gly Pro
        275                 280                 285

Gly Gln Gln Gly Pro Gly Gln Gly Pro Tyr Gly Pro Gly Ala Ser
    290                 295                 300

Ala Ala Ala Ala Ala Ala Gly Gly Tyr Gly Pro Gly Ser Gly Gln Gln
305                 310                 315                 320

Gly Pro Gly Gln Gln Gly Pro Gly Gln Gln Gly Pro Gly Gln Gln Gly
            325                 330                 335

Pro Gly Gly Gln Gly Pro Tyr Gly Pro Gly Ala Ser Ala Ala Ala Ala
            340                 345                 350

Ala Ala Gly Gly Tyr Gly Pro Gly Ser Gly Gln Gln Gly Pro Gly Gln
            355                 360                 365

Gln Gly Pro Gly Gln Gln Gly Pro Gly Gln Gln Gly Pro Gly Gln Gln
    370                 375                 380

Gly Pro Gly Gln Gln Gly Pro Gly Gln Gln Gly Pro Gly Gln Gln Gly
385                 390                 395                 400

Pro Gly Gln Gln Gly Pro Gly Gly Gln Gly Ala Tyr Gly Pro Gly Ala
            405                 410                 415

Ser Ala Ala Ala Gly Ala Ala Gly Gly Tyr Gly Pro Gly Ser Gly Gln
                420                 425                 430

Gln Gly Pro Gly Gln Gln Gly Pro Gly Gln Gln Gly Pro Gly Gln Gln
    435                 440                 445

Gly Pro Gly Gln Gln Gly Pro Gly Gln Gln Gly Pro Gly Gln Gln Gly
450                 455                 460

Pro Gly Gln Gln Gly Pro Tyr Gly Pro Gly Ala Ser Ala Ala Ala Ala
465                 470                 475                 480

Ala Ala Gly Gly Tyr Gly Pro Gly Ser Gly Gln Gln Gly Pro Gly Gln
                485                 490                 495
```

Gln Gly Pro Gly Gln Gly Pro Gly Gln Gly Pro Tyr Gly Pro
            500                 505                 510

Gly Ala Ala Ser Ala Ala Val Ser Val Gly Gly Tyr Gly Pro Gln Ser
            515                 520                 525

Ser Ser Val Pro Val Ala Ser Ala Val Ala Ser Arg Leu Ser Ser Pro
530                 535                 540

Ala Ala Ser Ser Arg Val Ser Ser Ala Val Ser Ser Leu Val Ser Ser
545                 550                 555                 560

Gly Pro Thr Lys His Ala Ala Leu Ser Asn Thr Ile Ser Ser Val Val
                565                 570                 575

Ser Gln Val Ser Ala Ser Asn Pro Gly Leu Ser Gly Cys Asp Val Leu
            580                 585                 590

Val Gln Ala Leu Leu Glu Val Val Ser Ala Leu Val Ser Ile Leu Gly
            595                 600                 605

Ser Ser Ser Ile Gly Gln Ile Asn Tyr Gly Ala Ser Ala Gln Tyr Thr
610                 615                 620

Gln Met Val Gly Gln Ser Val Ala Gln Ala Leu Ala
625                 630                 635

<210> SEQ ID NO 9
<211> LENGTH: 410
<212> TYPE: PRT
<213> ORGANISM: Araneus diadematus

<400> SEQUENCE: 9

Ala Gly Ser Ser Ala Ala Ala Ala Ala Ser Gly Ser Gly Gly
1               5                   10                  15

Tyr Gly Pro Glu Asn Gln Gly Pro Ser Gly Pro Val Ala Tyr Gly Pro
            20                  25                  30

Gly Gly Pro Val Ser Ser Ala Ala Ala Ala Ala Ala Gly Ser Gly
            35                  40                  45

Pro Gly Gly Tyr Gly Pro Glu Asn Gln Gly Pro Ser Gly Pro Gly Gly
    50                  55                  60

Tyr Gly Pro Gly Gly Ser Gly Ser Ser Ala Ala Ala Ala Ala Ala
65                  70                  75                  80

Ala Ser Gly Pro Gly Gly Tyr Gly Pro Gly Ser Gln Gly Pro Ser Gly
                85                  90                  95

Pro Gly Gly Ser Gly Gly Tyr Gly Pro Gly Ser Gln Gly Ala Ser Gly
            100                 105                 110

Pro Gly Gly Pro Gly Ala Ser Ala Ala Ala Ala Ala Ala Ala Ala
            115                 120                 125

Ala Ser Gly Pro Gly Gly Tyr Gly Pro Gly Ser Gln Gly Pro Ser Gly
130                 135                 140

Pro Gly Ala Tyr Gly Pro Gly Gly Pro Gly Ser Ser Ala Ala Ala Ala
145                 150                 155                 160

Ala Ala Ala Ala Ser Gly Pro Gly Gly Tyr Gly Pro Gly Ser Gln Gly
                165                 170                 175

Pro Ser Gly Pro Gly Val Tyr Gly Pro Gly Gly Pro Gly Ser Ser Ala
            180                 185                 190

Ala Ala Ala Ala Ala Gly Ser Gly Pro Gly Gly Tyr Gly Pro Glu
            195                 200                 205

Asn Gln Gly Pro Ser Gly Pro Gly Gly Tyr Gly Pro Gly Gly Ser Gly
            210                 215                 220

Ser Ser Ala Ala Ala Ala Ala Ala Ala Ser Gly Pro Gly Gly Tyr
225                 230                 235                 240

-continued

```
Gly Pro Gly Ser Gln Gly Pro Ser Gly Pro Gly Ser Gly Gly Tyr
            245                 250                 255

Gly Pro Gly Ser Gln Gly Gly Ser Gly Pro Gly Ala Ser Ala Ala
            260                 265                 270

Ala Ala Ala Ala Ala Ser Gly Pro Gly Gly Tyr Gly Pro Gly Ser Gln
        275                 280                 285

Gly Pro Ser Gly Pro Gly Tyr Gln Gly Pro Ser Gly Pro Gly Ala Tyr
        290                 295                 300

Gly Pro Ser Pro Ser Ala Ser Ala Ser Val Ala Ala Ser Val Tyr Leu
305                 310                 315                 320

Arg Leu Gln Pro Arg Leu Glu Val Ser Ser Ala Val Ser Ser Leu Val
            325                 330                 335

Ser Ser Gly Pro Thr Asn Gly Ala Ala Val Ser Gly Ala Leu Asn Ser
            340                 345                 350

Leu Val Ser Gln Ile Ser Ala Ser Asn Pro Gly Leu Ser Gly Cys Asp
            355                 360                 365

Ala Leu Val Gln Ala Leu Leu Glu Leu Val Ser Ala Leu Val Ala Ile
        370                 375                 380

Leu Ser Ser Ala Ser Ile Gly Gln Val Asn Val Ser Ser Val Ser Gln
385                 390                 395                 400

Ser Thr Gln Met Ile Ser Gln Ala Leu Ser
            405                 410

<210> SEQ ID NO 10
<211> LENGTH: 140
<212> TYPE: PRT
<213> ORGANISM: Artificial sequence
<220> FEATURE:
<223> OTHER INFORMATION: NR3 (ADF-3)

<400> SEQUENCE: 10

Met Ala Ser Met Thr Gly Gly Gln Gln Met Gly Arg Gly Ser Met Gly
1               5                   10                  15

Ala Ala Ser Ala Ala Val Ser Val Gly Gly Tyr Gly Pro Gln Ser Ser
            20                  25                  30

Ser Ala Pro Val Ala Ser Ala Ala Ser Arg Leu Ser Ser Pro Ala
        35                  40                  45

Ala Ser Ser Arg Val Ser Ser Ala Val Ser Ser Leu Val Ser Ser Gly
    50                  55                  60

Pro Thr Asn Gln Ala Ala Leu Ser Asn Thr Ile Ser Ser Val Val Ser
65                  70                  75                  80

Gln Val Ser Ala Ser Asn Pro Gly Leu Ser Gly Cys Asp Val Leu Val
            85                  90                  95

Gln Ala Leu Leu Glu Val Val Ser Ala Leu Val Ser Ile Leu Gly Ser
            100                 105                 110

Ser Ser Ile Gly Gln Ile Asn Tyr Gly Ala Ser Ala Gln Tyr Thr Gln
            115                 120                 125

Met Val Gly Gln Ser Val Ala Gln Ala Leu Ala Gly
    130                 135                 140

<210> SEQ ID NO 11
<211> LENGTH: 125
<212> TYPE: PRT
<213> ORGANISM: Artificial sequence
<220> FEATURE:
<223> OTHER INFORMATION: NR4 (ADF-4)
```

-continued

<400> SEQUENCE: 11

Met Ala Ser Met Thr Gly Gly Gln Gln Met Gly Arg Gly Ser Met Gly
1               5                   10                  15

Ala Tyr Gly Pro Ser Pro Ser Ala Ser Ala Ser Val Ala Ala Ser Arg
            20                  25                  30

Leu Ser Ser Pro Ala Ala Ser Ser Arg Val Ser Ser Ala Val Ser Ser
        35                  40                  45

Leu Val Ser Ser Gly Pro Thr Asn Gly Ala Ala Val Ser Gly Ala Leu
    50                  55                  60

Asn Ser Leu Val Ser Gln Ile Ser Ala Ser Asn Pro Gly Leu Ser Gly
65                  70                  75                  80

Cys Asp Ala Leu Val Gln Ala Leu Leu Glu Leu Val Ser Ala Leu Val
                85                  90                  95

Ala Ile Leu Ser Ser Ala Ser Ile Gly Gln Val Asn Val Ser Ser Val
            100                 105                 110

Ser Gln Ser Thr Gln Met Ile Ser Gln Ala Leu Ser Gly
        115                 120                 125

<210> SEQ ID NO 12
<211> LENGTH: 1959
<212> TYPE: DNA
<213> ORGANISM: Araneus diadematus

<400> SEQUENCE: 12
atggctagca tgactggtgg acagcaaatg ggtcgggatc cgaattcggc acgagccgga      60
tctggacaac aaggacccgg acaacaagga cccggacaac aaggacccgg acaacaagga     120
ccatatggac cggtgcatc cgccgcagca gcagccgctg gaggttatgg acccggatct     180
ggacaacaag gacccagcca acaaggacct ggccaacaag acccggtgg tcaaggacca     240 tatggacccg gtgcatccgc cgccgcagca gccgctggtg atatggacc cggttccgga     300 caacaaggac caggaggtca aggaccatat ggacctggtt catccgctgc cgcagcagcc     360
gctggaggta atggacccgg atctggacaa caagggcccg gtcaacaagg tcctggacaa     420
caaggacccg gtgcatccgc cgccgcagca gccgctggag gatacggacc cggatctgga     480
caacaaggac ccggacaaca aggaccagga ggtcaaggac catatggacc tggtgcatcc     540
gccgctgcag cagccgctgg aggatacgga cccggatctg gacaacaagg acccggacaa     600
caaggaccag gaggtcaagg accatatgga cccggtgcat ccgctgcagc agcagccgct     660
ggaggttatg gacccggatc tgacaacaa ggacccggac aacaaggacc tggacaacaa     720
ggacccggtg gtcaaggacc atatggaccc ggtgcatccg ccgccgcagc agccgctgga     780
ggatacggac ccggttatgg acagcaagga ccaggacaac aaggaccagg aggtcaagga     840
ccatatggac ctggtgcatc cgccgcctca gcagcctctg gaggatacgg acccggatct     900
ggacaacaag gacccggaca acaaggacct ggaggtcaag gaccatatgg acctggtgca     960
tccgccgcag cagcagccgc tggaggttat ggacccggat ctggacaaca aggaccaggc    1020
caacaaggac ccgtcaaca aggacctgga caacaaggac ccgtggtca aggaccatat    1080 ggacctggtg catccgccgc agcagcagcc gctggaggtt atggacccgg atctggacaa    1140
caaggacccg gtcaacaagg acccggtcaa caaggacccg gtcaacaagg acccggtcaa    1200
caaggacccg gccaacaagg acccggtcaa caaggacccg gccaacaagg acctggtcaa    1260
caaggtcccg gtggtcaagg gcatatgga cctggtgcat ccgccgcagc aggagccgct    1320
ggaggttatg gacccggatc tgacaacaa ggacccggac aacaaggacc cggacaacaa    1380

```
ggacccggac aacaaggacc cggacaacaa ggacccggac aacaaggacc cggacaacaa    1440
ggacccggac aacaaggacc atatggacct ggtgcatccg ccgcagcagc agccgctgga    1500
ggttatggac ccggatctgg acaacaagga cccggccaac aaggacctgg acaacaagga    1560
cccgttggtc aaggaccata tggacctggt gcggcttctg cagctgtatc tgttggagga    1620
tatggaccac aaagctcctc ggctcctgtt gcatcagcag ccgcttctcg cctttcttct    1680
ccagcggcca gttctagagt ttcatcggct gtatcatctt tggtatctag tggacctact    1740
aatcaagctg cactttctaa tactatcagt agcgttgtat cgcaagttag tgcaagtaat    1800
cctggtcttt ctggttgcga tgtacttgtg caagcattgc tcgaagttgt atcggccctg    1860
gtatctatcc ttggatcttc tagtatcggg caaattaact atggtgcctc tgctcagtac    1920
acccaaatgg taggtcaatc tgtagctcaa gcccttgct                           1959

<210> SEQ ID NO 13
<211> LENGTH: 2013
<212> TYPE: DNA
<213> ORGANISM: Araneus diadematus

<400> SEQUENCE: 13
atggctagca tgactggtgg acagcaaatg ggtcgcgcgg cacgagcagg atcttcagca      60
gcagcggccg cggcagcaag tggatctgga ggatacggac ctgaaaacca aggaccatct     120
ggacctgtag catatggacc tggtggaccc gtatcttcag ctgcagcagc agccgctgca     180
ggaagtggac ctggtggata cggacctgaa aaccaaggac catctggacc cggaggatat     240
ggacctggtg gttccggatc ttcagcagca gcagcagccg ctgcagcaag tggacctgga     300
ggatatggac ctggaagcca aggaccatct ggacctggtg gatccggagg atatggtccc     360
ggaagccaag ggccatctgg acctggtgca tcttcggcag cagcagcagc cgctgcagca     420
agtggacctg gaggatatgg acctggaagc caaggaccat ctggacctgg agcatatgga     480
cctggtggac ccggatcttc agctgcagca agtggacctg gaggatatgg acctggaagc     540
caaggaccat ctggacctgg tgatccggga ggatatggtc ccggaagcca agggccatct     600
ggacctggtg ggcctggtgc atctgcggca gcagcagcag ccgctgcagc aagtggacct     660
ggaggatatg gacctggaag ccaaggacca tctggacctg gagcatatgg acctggtgga     720
cccggatctt cagctgcagc aagtggacct ggaggatatg gacctggaag ccaaggacca     780
tctggacctg gagcatatgg acctggtgga cccggatctt cagctgcagc agcagccgct     840
gcaggaagtg gacctggtgg atacggacct ggaaaccaag gaccatctgg acccggagga     900
tatggacctg gtggtcccgg atcttcagca gcagccgctg cagcaagtgg acctgga         960 ggatatggac ctggaagcca aggaccatct ggacctggag tatatggacc tggtggaccc    1020
ggatcttcag ctgcagcagc agccgctgca ggaagtggac ctggtggata cggacctgga    1080
aaccaaggac catctggacc cggaggatat ggacctggtg gttccggatc ttcagcagca    1140
gcagcagccg ctgcagcaag tggacctgga ggatatggac ctggaagcca aggaccatct    1200
ggacctggtg gatccggagg atatggtccc ggaagccaag ggccatctgg acctggtgca    1260
tcttcggcag cagcagcagc cgctgcagca agtggacctg gaggatatgg acctggaagc    1320
caaggaccat ctggacctgg agcatatgga cctggtggac ccggatcttc agctgcagca    1380
agtggacctg gaggatatgg acctggaagc caaggaccat ctggtcctgg agcatatgga    1440
cctggtggac ccggatcttc agctgcagca gccgctgcag caagtggacc tggaggatat    1500
ggacctggaa gccaaggacc atctggacct ggtggatccc gaggatatgg tcccggaagc    1560
```

```
caaggacctg gtgggcctgg agcatctgcg gcagcagcag cagccgctgc agcaagtgga    1620
cctggaggat atggacctgg aagccaagga ccatctggac ctggatatca aggccctagt    1680
ggtcctggag catatggccc atctccttct gcttccgcat ccgttgcagc ctctcgttta    1740
tcttcgcctg cagcctcgtc tagagtgtct tccgctgtat cgtctttagt gtctagcgga    1800
cctacgaatg tgctgctgt ttctggagct ttgaatagtt tagtatctca gattagtgca     1860
agtaatccag gtttatcggg atgtgatgct cttgtgcagg cattattgga attagtgtct    1920
gctcttgtgg caattctttc atctgcaagt attggccaag tcaacgtcag ctctgttagt    1980
cagtcaactc aaatgattag ccaagctctt tca                                 2013

<210> SEQ ID NO 14
<211> LENGTH: 420
<212> TYPE: DNA
<213> ORGANISM: Artificial sequence
<220> FEATURE:
<223> OTHER INFORMATION: NR3 (ADF-3)

<400> SEQUENCE: 14
atggctagca tgactggtgg acagcaaatg ggtcgcggat ccatgggtgc ggcttctgca      60
gctgtatctg ttggaggata tggaccacaa agctcctcgg ctcctgttgc atcagcagcc    120
gcttctcgcc tttcttctcc agcggccagt tctcgtgttt catcggctgt atcatctttg    180
gtatctagtg gacctactaa tcaagctgca ctttctaata ctatcagtag cgttgtatcg    240
caagttagtg caagtaatcc tggtctttct ggttgcgatg tacttgtgca agcattgctc    300
gaagttgtat cggccctggt atctatcctt ggatcttcta gtatcgggca aattaactat    360
ggtgcctctg ctcagtacac ccaaatggta ggtcaatctg tagctcaagc ccttgctggc    420

<210> SEQ ID NO 15
<211> LENGTH: 375
<212> TYPE: DNA
<213> ORGANISM: Artificial sequence
<220> FEATURE:
<223> OTHER INFORMATION: NR4 (ADF-4)

<400> SEQUENCE: 15
atggctagca tgactggtgg acagcaaatg ggtcgcggat ccatgggagc atatggccca     60
tctccttctg cttccgcatc cgttgcagcc tctcgtttat cttcgcctgc agcctcgtct    120
cgtgtgtctt ccgctgtatc gtctttagtg tctagcggac ctacgaatgg tgctgctgtt    180
tctggagctt tgaatagttt agtatctcag attagtgcaa gtaatccagg tttatcggga    240
tgtgatgctc ttgtgcaggc attattggaa ttagtgtctg ctcttgtggc aattctttca    300
tctgcaagta ttggccaagt caacgtcagc tctgttagtc agtcaactca aatgattagc    360
caagctcttt caggc                                                     375

<210> SEQ ID NO 16
<211> LENGTH: 2828
<212> TYPE: DNA
<213> ORGANISM: Nephila clavipes

<400> SEQUENCE: 16
gcttgcttta cctcggcagt gatatttctt ttcttagcgc agtgtgcgtc gacgtacgga     60 aggggatta tagccaactc cccttttctca aaccctaaca cagcggaagc ttttgcacga    120
tctttcgtga gcaatattgt ttctagtgga gaatttggag cccaaggagc gaagacttc     180 gatgacataa ttcagagtct catacaggcc cagagcatgg gcaaagggcg gcatgatacg    240
```

```
aaggccaagg cgaaagcgat gcaggtagcc cttgcttctt ctatagccga attggttatt    300
gcagaaagca gcggaggcga tgtgcaacgc aaaaccaacg ttatctccaa cgctttgaga    360
aacgccttga tgtctacaac aggcagccca aacgaagagt tcgtccatga agttcaagac    420
ctcatccaga tgttatctca agaacagatc aacgaggtag atacttcagg accagggcag    480
tactacaggt cgtcttcttc cggtggagga ggtggaggac aaggaggtcc tgtagttact    540
gaaacactga ccgttacagt tggcggatcc ggtggagggc aaccttcagg tgcaggtcct    600
agtggtacag gtggatatgc accaactgga tacgcccccaa gcggctcagg tgcaggtggc    660
gttcgaccta gtgcctccgg tccaagtggt agtggaccta gtggtggatc tcgtcctagt    720
agtagtggac ctagtggaac tcgtcccagc cctaatggtg caagtggatc tagccctggt    780
ggtatcgcac ctggtggatc caattctggt ggtgctggag tatccggcgc aactggagga    840
cctgcatcca gcggctccta cggaccagga agtacaggtg aacatatgg acctagtgga    900 ggaagtgaac ctttcggacc aggagtggct ggaggaccat acagcccagg tgagctggaa    960
cctggtggtg caggtggagc ctatggacca ggaggtgtag aactggtgg agccggacca   1020 ggaggttacg gacctggtgg agccggacca ggaggttatg gacctggtgg agccggacca   1080
ggaggttacg gacctggtgg agctggacca ggaggttacg gacctggtgg agctgggcct   1140
ggaggttacg gacctggtgg agctggacct ggaggttacg gacctggtgg agctggacct   1200
ggaggttacg gacctggtgg aactggacct ggtggatacg gacctggtgg aactggacct   1260
ggaggagttg gacctggagg agctggacca ggaggatatg gacctggtgg tgctggacct   1320
ggtggtgctg gacctggtgg tgctggacct ggtggtgctg gacctggtgg tgctggacct   1380
ggtggtgctg gacctggtgg atacggccct ggtggatctg gacctggtgg tgctggacct   1440
agtggtgccg gacttggtgg tgctggacct ggaggtgcgg gacttggtgg agcaggacct   1500
ggaggagcag gaaccagtgg tgccggaccc ggtggagcag gacccggtgg agcaggacaa   1560
ggtgatgctg gacccggtgg tgcaggacgt ggaggagcag gtcgtggtgg tgtaggtcgt   1620
ggtggtgcag gtcgtggagg tgcaggacgt ggtggagcta gaggtgctgg tggagcagga   1680
ggtgctggtg gagcaggagg atccggcggc acaacaatcg tagaggactt ggatattaca   1740
attgatggtg cagatggccc gataacaata tcagaagaat taacaatcgg tggagcaggc   1800
gctggaggtt ccggacccgg tggtgctgga ccaggaaacg ttggacctgg tcgctctgga   1860
ccaggaggag taggacctgg tggctctgga ccaggaggcg taggacctgg tagctttgga   1920
ccaggaggcg taggacctgg tggctccgga ccaggaggcg taggatctgg tggctccgga   1980
caaggaggag taagacctag tggctccgga ccaggtggcg taggaactgg aggcgtagga   2040
cccggtggtc ctggaggacc ttacggtcct ggtggttccg gacccggagg tgcaggaagc   2100
gctggaggaa cttatggacc tggtggtttc ggaggacccg gtggtttcgg aggacccggt   2160
ggtgctggtg gacccctacgg tccaggtggt gctggtggac cctacggacc aggtggtgct   2220
ggtggaccct acgaccaggg tggtgctggt ggacccctacg ggccgggtgg tgctggtgga   2280
ccctacgggc cggaggtgc tggtggatcc tacgggctgg gtggtgctgg tggatcagga   2340
ggtgtaggac ctggtggaag tggacctgga ggttatggac ccgtggagc gggacctgga   2400 ggttacggac ccgtggttc tggtccaggt ggatacggac ctggcggttc tggatctggt   2460
ggatacggac ctggaggttc tggacctggt ggttctggac ctggtggata cggacctggt   2520
ggtactggac ctggtggttc tgaatctggt ggatacggac ctggtggatc tggacctggc   2580
ggttctggac ctggtggatc tggacctggc ggttctggac ctggtggata cggacctggt   2640
```

-continued

| | | |
|---|---|---|
| ggttctggac ctagcagttt tgtacctggc ggttctggac ctggtggctc tggacccggt | 2700 | |
| ggcgctggac ccggtggcgc tggacccggt ggtgttggac ttggaggtgc tggacgtggt | 2760 | |
| ggagctggac gtggtggagc tggaagtgtt ggagctggac gtggtggagc tggacgtggt | 2820 | |
| ggaactgg | 2828 | |

<210> SEQ ID NO 17
<211> LENGTH: 2724
<212> TYPE: DNA
<213> ORGANISM: Nephila clavipes

<400> SEQUENCE: 17

| | |
|---|---|
| ggaccaggag gtgtaggacc tggtggaagt ggacctggag gttatggacc cggtggagct | 60 |
| ggacctggag gttacggacc tggtggttct ggtccaggtg gatacggacc cggtggttcg | 120 |
| ggaccaggag gatacggacc tggcggttct ggacctggtg gatacggacc aggcggttct | 180 |
| ggacctggtg gatacggacc aggcggttct ggacctggtg gatacggacc tggtggatat | 240 |
| ggacctggtg gttctggacc tggtggatat ggacctggtg gtactggacc tggtggttct | 300 |
| ggacccggcg gatacggacc tggtggttct ggacctggcg gttctggacc tggtggatac | 360 |
| ggacctggtg gttctggacc tggcggtttt ggacctggcg gttctggacc tggtggatac | 420 |
| ggacctggtg gctctggacc cggtggtgct ggtcccggtg gtgttggacc cggtggtttt | 480 |
| ggacctggtg gtgctggacc cggtggagct ggacctggtg gtgctggacc tggtggtgct | 540 |
| ggacctggtg gtgctggacc tggtggagct ggacctggtg gtgctggacc tggtggagct | 600 |
| ggacctggtg gtgctggacc tggtggagct ggacctggtg gtgctggtgg cgctggagga | 660 |
| gcaggcggag caggaggttc aggtggagca ggaggatccg gcggtacaac aatcatagaa | 720 |
| gacttggata ttacaattga tggcgctgat ggcccgataa cgatttcaga agaattaaca | 780 |
| attagtggtg ctggaggttc cggacccggt ggtgctggac caggaggtgt agggcctggt | 840 |
| ggctccggac caggaggtgt aggacctgga ggctctggac caggaggtgt aggacctggt | 900 |
| ggttctggtc caggaggcgt aggacctggt ggtgctggtg gaccttacgg acctggcggt | 960 |
| tctggacctg gaggtgcagg cggagctgga ggacctggtg gagcatacgg acctggtgga | 1020 |
| tcatatggac ctggtggttc cggaggaccc ggtggtgctg gcggaccata cggacctgga | 1080 |
| ggtgaaggac ccgtggtgc tggcggaccc tacggacctg gtggtgcagg tggaccttac | 1140 |
| ggcccaggtg gtgcaggtgg accctacgga ccaggtggtg aaggtggacc ctacggacca | 1200 |
| ggtggatcat acggaccggg tggtgctggt ggaccatacg gaccaggtgg accctacgga | 1260 |
| cctggaggtg aaggaccagg tggtgctggc ggaccctatg gaccaggagg tgtaggacct | 1320 |
| ggtggaagtg gacctggagg ttatggacct ggtggaagtg gacctggagg ttatggacct | 1380 |
| ggtggagctg gacctggagg ttacggacct ggtggttctg gtccaggtgg atacggaccc | 1440 |
| ggtggttctg gtccaggtgg atacggaccc ggtggttccg gaccaggagg atacggacct | 1500 |
| ggcggttctg gacctggtgg atacggatct ggcggtgctg gacctggtgg atacggacct | 1560 |
| ggcggttctg gacctggtgg atacggtcct ggaggttctg gacctggtgg ttatggacct | 1620 |
| ggtggtactg gacctggtgg tactggacct ggtggttctg gacctggcgg atacggacct | 1680 |
| ggtggttctg gacctggcgg ttctggacct ggcggttctg gacctggtgg atacggacct | 1740 |
| agtggttcgg gacctggtgg atacggacct agtggttctg gacctggcgg atacggtcct | 1800 |
| ggcggttctg gacctggtgg atacggaccg gtggctctg gagccggtgg tactggacct | 1860 |
| ggtggcgctg gaggagcagg cggagcagga ggttcaggtg gagcaggagg ttcaggtggt | 1920 |

```
gcaggaggtt caggtggagc aggaggttca ggtggagtag gaggatccgg cggtacaaca      1980
atcaccgaag acttggatat tacaattgat ggcgcagatg gcccgataac gatttcagaa      2040
gaattaacaa ttagtggtgc tggaggttct ggacccggtg gtgctggacc aggtggtgta      2100
gggcctggtg gctctggacc aggaggtgta ggacctggag tctctggacc aggaggcgta      2160
ggacctggtg gttctggacc aggaggcgta ggttctggtg gttctggacc aggaggcgta      2220
ggacctggtg gttacggacc tggaggttct ggatcaggag gcgtaggacc tggtggttac      2280
ggacctggag gttcaggagg attttacgga cctggaggtt cagaaggacc ttatggacct      2340
agtggaactt atggttctgg aggaggatat ggtcctggtg gtgctggagg accatatgga      2400
cctggaagtc ctggaggagc ttatggacct ggaagccctg gaggagctta ttatcctagc      2460
tcgcgtgttc ccgatatggt gaatggtata atgagtgcta tgcaaggatc tggttttaac      2520
taccaaatgt ttggtaatat gctatcacaa tattcgtctg gttcaggaac atgcaatcca      2580
aataatgtta atgttttgat ggatgctttg ttagctgctt tgcactgtct aagtaaccac      2640
ggatcatcat cttttgcacc ttctccaact ccggctgcta tgagtgcgta ttctaattct      2700
gtaggaagaa tgttcgctta ttaa                                             2724

<210> SEQ ID NO 18
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 18
gatcgaggag gatccatggg acgaattcac ggctaatgaa agcttactgc ac              52

<210> SEQ ID NO 19
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 19
agctgtgcag taagctttca ttagccgtga attcgtccca tggatcctcc tc              52

<210> SEQ ID NO 20
<211> LENGTH: 72
<212> TYPE: DNA
<213> ORGANISM: Artificial sequence
<220> FEATURE:
<223> OTHER INFORMATION: synthetic oligonucleotide

<400> SEQUENCE: 20
tccgtacggc ccaggtgcta gcgccgcagc ggcagcggct ggtggctacg gtccgggctc      60
tggccagcag gg                                                          72

<210> SEQ ID NO 21
<211> LENGTH: 72
<212> TYPE: DNA
<213> ORGANISM: Artificial sequence
<220> FEATURE:
<223> OTHER INFORMATION: synthetic oligonucleotide

<400> SEQUENCE: 21
ctgctggcca gagcccggac cgtagccacc agccgctgcc gctgcggcgc tagcacctgg      60
gccgtacgga cc                                                          72
```

```
<210> SEQ ID NO 22
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 22
tccgggccag cagggcccgg gtcaacaggg tcctggccag caaggtccgg gccagcaggg      60

<210> SEQ ID NO 23
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 23
ctgctggccc ggaccttgct ggccaggacc ctgttgaccc gggccctgct ggcccggacc      60

<210> SEQ ID NO 24
<211> LENGTH: 105
<212> TYPE: DNA
<213> ORGANISM: Artificial sequence
<220> FEATURE:
<223> OTHER INFORMATION: synthetic oligonucleotide

<400> SEQUENCE: 24
ttctagcgcg gctgcagccg cggcagctgc gtccggcccg ggtggctacg gtccggaaaa      60
ccagggtcca tctggcccgg gtggctacgg tcctggcggt ccggg                    105

<210> SEQ ID NO 25
<211> LENGTH: 105
<212> TYPE: DNA
<213> ORGANISM: Artificial sequence
<220> FEATURE:
<223> OTHER INFORMATION: synthetic oligonucleotide

<400> SEQUENCE: 25
cggaccgcca ggaccgtagc cacccgggcc agatggaccc tggttttccg gaccgtagcc      60
acccgggccg gacgcagctg ccgcggctgc agccgcgcta gaacc                    105

<210> SEQ ID NO 26
<211> LENGTH: 36
<212> TYPE: DNA
<213> ORGANISM: Artificial sequence
<220> FEATURE:
<223> OTHER INFORMATION: Primer

<400> SEQUENCE: 26
gaaaaaccat gggtgcggct tctgcagctg tatctg                              36

<210> SEQ ID NO 27
<211> LENGTH: 45
<212> TYPE: DNA
<213> ORGANISM: Artificial sequence
<220> FEATURE:
<223> OTHER INFORMATION: Primer

<400> SEQUENCE: 27
gaaaagaagc tttccattagc cagcaagggc ttgagctaca gattg                    45

<210> SEQ ID NO 28
<211> LENGTH: 34
<212> TYPE: DNA
<213> ORGANISM: Artificial Sequence
```

-continued

```
<220> FEATURE:
<223> OTHER INFORMATION: Primer

<400> SEQUENCE: 28
gaaaaaccat gggagcatat ggcccatctc cttc                              34

<210> SEQ ID NO 29
<211> LENGTH: 45
<212> TYPE: DNA
<213> ORGANISM: Artificial sequence
<220> FEATURE:
<223> OTHER INFORMATION: Primer

<400> SEQUENCE: 29
gaaaagaagc tttcattagc ctgaaagagc ttggctaatc atttg                  45

<210> SEQ ID NO 30
<211> LENGTH: 12
<212> TYPE: PRT
<213> ORGANISM: Artificial sequence
<220> FEATURE:
<223> OTHER INFORMATION: T7 tag

<400> SEQUENCE: 30

Met Ala Ser Met Thr Gly Gly Gln Gln Met Gly Arg
1               5                   10

<210> SEQ ID NO 31
<211> LENGTH: 216
<212> TYPE: PRT
<213> ORGANISM: Artificial sequence
<220> FEATURE:
<223> OTHER INFORMATION: FlagN-NR

<400> SEQUENCE: 31

Gly Glu Ser Ser Gly Gly Asp Val Gln Arg Lys Thr Asn Val Ile Ser
1               5                   10                  15

Asn Ala Leu Arg Asn Ala Leu Met Ser Thr Thr Gly Ser Pro Asn Glu
            20                  25                  30

Glu Phe Val His Glu Val Gln Asp Leu Ile Gln Met Leu Ser Gln Glu
        35                  40                  45

Gln Ile Asn Glu Val Asp Thr Ser Gly Pro Gly Gln Tyr Tyr Arg Ser
    50                  55                  60

Ser Ser Ser Gly Gly Gly Gly Gly Gln Gly Gly Pro Val Val Thr
65                  70                  75                  80

Glu Thr Leu Thr Val Thr Val Gly Gly Ser Gly Gly Gln Pro Ser
                85                  90                  95

Gly Ala Gly Pro Ser Gly Thr Gly Gly Tyr Ala Pro Thr Gly Tyr Ala
            100                 105                 110

Pro Ser Gly Ser Gly Ala Gly Gly Val Arg Pro Ser Ala Ser Gly Pro
        115                 120                 125

Ser Gly Ser Gly Pro Ser Gly Ser Arg Pro Ser Ser Ser Gly Pro
    130                 135                 140

Ser Gly Thr Arg Pro Ser Pro Asn Gly Ala Ser Gly Ser Ser Pro Gly
145                 150                 155                 160

Gly Ile Ala Pro Gly Gly Ser Asn Ser Gly Gly Ala Gly Val Ser Gly
                165                 170                 175

Ala Thr Gly Gly Pro Ala Ser Ser Gly Ser Tyr Gly Pro Gly Ser Thr
            180                 185                 190
```

```
Gly Gly Thr Tyr Gly Pro Ser Gly Gly Ser Glu Pro Phe Gly Pro Gly
        195                 200                 205

Val Ala Gly Gly Pro Tyr Ser Pro
        210                 215

<210> SEQ ID NO 32
<211> LENGTH: 648
<212> TYPE: DNA
<213> ORGANISM: Artificial Sequence
<220> FEATURE:
<223> OTHER INFORMATION: FlagN-NR

<400> SEQUENCE: 32
ggcgaaagca gcggaggcga tgtgcaacgc aaaaccaacg ttatctccaa cgctttgaga      60
aacgccttga tgtctacaac aggcagccca aacgaagagt tcgtccatga agttcaagac    120
ctcatccaga tgttatctca agaacagatc aacgaggtag atacttcagg accagggcag    180
tactacaggt cgtcttcttc cggtggagga ggtggaggac aaggaggtcc tgtagttact    240
gaaacactga ccgttacagt tggcggatcc ggtggagggc aaccttcagg tgcaggtcct    300
agtggtacag tggatatgc accaactgga tacgccccaa gcggctcagg tgcaggtggc    360
gttcgaccta gtgcctccgg tccaagtggt agtggaccta gtggtggatc tcgtcctagt    420
agtagtggac ctagtggaac tcgtcccagc cctaatggtg caagtggatc tagccctggt    480
ggtatcgcac ctggtggatc caattctggt ggtgctggag tatccggcgc aactggagga    540
cctgcatcca gcggctccta cggaccagga agtacaggtg aacatatgg acctagtgga    600 ggaagtgaac ctttcggacc aggagtggct ggaggaccat acagccca                 648

<210> SEQ ID NO 33
<211> LENGTH: 93
<212> TYPE: PRT
<213> ORGANISM: Artificial sequence
<220> FEATURE:
<223> OTHER INFORMATION: FlagC-NR

<400> SEQUENCE: 33

Gly Ala Tyr Tyr Pro Ser Ser Arg Val Pro Asp Met Val Asn Gly Ile
1               5                   10                  15

Met Ser Ala Met Gln Gly Ser Gly Phe Asn Tyr Gln Met Phe Gly Asn
            20                  25                  30

Met Leu Ser Gln Tyr Ser Ser Gly Ser Gly Thr Cys Asn Pro Asn Asn
        35                  40                  45

Val Asn Val Leu Met Asp Ala Leu Leu Ala Ala Leu His Cys Leu Ser
    50                  55                  60

Asn His Gly Ser Ser Ser Phe Ala Pro Ser Pro Thr Pro Ala Ala Met
65                  70                  75                  80

Ser Ala Tyr Ser Asn Ser Val Gly Arg Met Phe Ala Tyr
                85                  90

<210> SEQ ID NO 34
<211> LENGTH: 279
<212> TYPE: DNA
<213> ORGANISM: Artificial sequence
<220> FEATURE:
<223> OTHER INFORMATION: FlagC-NR

<400> SEQUENCE: 34
ggtgcttatt atcctagctc gcgtgttccc gatatggtga atggtataat gagtgctatg     60
caaggatctg gttttaacta ccaaatgttt ggtaatatgc tatcacaata ttcgtctggt    120
```

```
tcaggaacat gcaatccaaa taatgttaat gttttgatgg atgctttgtt agctgctttg    180
cactgtctaa gtaaccacgg atcatcatct tttgcacctt ctccaactcc ggctgctatg    240
agtgcgtatt ctaattctgt aggaagaatg ttcgcttat                           279
```

```
<210> SEQ ID NO 35
<211> LENGTH: 27
<212> TYPE: PRT
<213> ORGANISM: Artificial sequence
<220> FEATURE:
<223> OTHER INFORMATION: Module K

<400> SEQUENCE: 35
```

Gly Pro Gly Gly Ala Gly Gly Pro Tyr Gly Pro Gly Gly Ala Gly Gly
1               5                   10                  15

Pro Tyr Gly Pro Gly Gly Ala Gly Gly Pro Tyr
            20                  25

```
<210> SEQ ID NO 36
<211> LENGTH: 81
<212> TYPE: DNA
<213> ORGANISM: Artificial sequence
<220> FEATURE:
<223> OTHER INFORMATION: Module K

<400> SEQUENCE: 36
```

```
ggtccgggcg gtgctggcgg tccgtacggc cctggtggcg caggtgggcc atatggtccg    60
ggcggtgcgg gcggtccgta c                                              81
```

```
<210> SEQ ID NO 37
<211> LENGTH: 28
<212> TYPE: PRT
<213> ORGANISM: Artificial sequence
<220> FEATURE:
<223> OTHER INFORMATION: Module sp

<400> SEQUENCE: 37
```

Gly Gly Thr Thr Ile Ile Glu Asp Leu Asp Ile Thr Ile Asp Gly Ala
1               5                   10                  15

Asp Gly Pro Ile Thr Ile Ser Glu Glu Leu Thr Ile
            20                  25

```
<210> SEQ ID NO 38
<211> LENGTH: 84
<212> TYPE: DNA
<213> ORGANISM: Artificial sequence
<220> FEATURE:
<223> OTHER INFORMATION: Module sp

<400> SEQUENCE: 38
```

```
ggtggcacca ccatcattga agatctggac atcactattg atggtgcgga cggcccgatc    60
acgatctctg aagagctgac catc                                           84
```

```
<210> SEQ ID NO 39
<211> LENGTH: 18
<212> TYPE: PRT
<213> ORGANISM: Artificial Sequence
<220> FEATURE:
<223> OTHER INFORMATION: Module X

<400> SEQUENCE: 39
```

Gly Gly Ala Gly Gly Ala Gly Gly Ala Gly Gly Ser Gly Gly Ala Gly
1               5                   10                  15

Gly Ser

```
<210> SEQ ID NO 40
<211> LENGTH: 54
<212> TYPE: DNA
<213> ORGANISM: Artificial sequence
<220> FEATURE:
<223> OTHER INFORMATION: Module X

<400> SEQUENCE: 40
ggtggcgctg gtggcgccgg tggcgcaggt ggctctggcg gtgcgggcgg ttcc        54

<210> SEQ ID NO 41
<211> LENGTH: 30
<212> TYPE: PRT
<213> ORGANISM: Artificial sequence
<220> FEATURE:
<223> OTHER INFORMATION: Module Y

<400> SEQUENCE: 41

Gly Pro Gly Gly Ala Gly Pro Gly Gly Tyr Gly Pro Gly Gly Ser Gly
1               5                   10                  15

Pro Gly Gly Tyr Gly Pro Gly Gly Ser Gly Pro Gly Gly Tyr
            20                  25                  30

<210> SEQ ID NO 42
<211> LENGTH: 90
<212> TYPE: DNA
<213> ORGANISM: Artificial sequence
<220> FEATURE:
<223> OTHER INFORMATION: Module Y

<400> SEQUENCE: 42
ggtccgggcg gtgcgggccc aggtggctat ggtccgggcg gttctggccc ggtggctac   60 ggtcctggcg gttccggccc gggtggctac                                   90

<210> SEQ ID NO 43
<211> LENGTH: 32
<212> TYPE: DNA
<213> ORGANISM: Artificial Sequence
<220> FEATURE:
<223> OTHER INFORMATION: PCR-Primer

<400> SEQUENCE: 43
gaaaaaccat gggcgaaagc agcggaggcg at                                32

<210> SEQ ID NO 44
<211> LENGTH: 36
<212> TYPE: DNA
<213> ORGANISM: Artificial Sequence
<220> FEATURE:
<223> OTHER INFORMATION: PCR-Primer

<400> SEQUENCE: 44
gaaaagaagc tttcattagc ctgggctgta tggtcc                            36

<210> SEQ ID NO 45
<211> LENGTH: 33
<212> TYPE: DNA
<213> ORGANISM: Artificial Sequence
<220> FEATURE:
<223> OTHER INFORMATION: PCR-Primer

<400> SEQUENCE: 45
gaaaaaccat gggtgcttat tatcctagct cgc                               33
```

```
<210> SEQ ID NO 46
<211> LENGTH: 42
<212> TYPE: DNA
<213> ORGANISM: Artificial Sequence
<220> FEATURE:
<223> OTHER INFORMATION: PCR-Primer

<400> SEQUENCE: 46
gaaaagaagc tttcattagc cataagcgaa cattcttcct ac                42

<210> SEQ ID NO 47
<211> LENGTH: 90
<212> TYPE: DNA
<213> ORGANISM: Artificial Sequence
<220> FEATURE:
<223> OTHER INFORMATION: synthetic oligonucleotide

<400> SEQUENCE: 47
tccgggcggt gcgggcccag gtggctatgg tccgggcggt tctgggccgg gtggctacgg    60
tcctggcggt tccggcccgg gtggctacgg                                    90

<210> SEQ ID NO 48
<211> LENGTH: 90
<212> TYPE: DNA
<213> ORGANISM: Artificial Sequence
<220> FEATURE:
<223> OTHER INFORMATION: synthetic oligonucleotide

<400> SEQUENCE: 48
gtagccaccc gggccggaac cgccaggacc gtagccaccc ggcccagaac cgcccggacc    60
atagccacct gggcccgcac cgcccggacc                                    90

<210> SEQ ID NO 49
<211> LENGTH: 84
<212> TYPE: DNA
<213> ORGANISM: Artificial Sequence
<220> FEATURE:
<223> OTHER INFORMATION: synthetic oligonucleotide

<400> SEQUENCE: 49
tggcaccacc atcattgaag atctggacat cactattgat ggtgcggacg gcccgatcac    60
gatctctgaa gagctgacca tcgg                                          84

<210> SEQ ID NO 50
<211> LENGTH: 84
<212> TYPE: DNA
<213> ORGANISM: Artificial Sequence
<220> FEATURE:
<223> OTHER INFORMATION: synthetic oligonucleotide

<400> SEQUENCE: 50
gatggtcagc tcttcagaga tcgtgatcgg gccgtccgca ccatcaatag tgatgtccag    60
atcttcaatg atggtggtgc cacc                                          84

<210> SEQ ID NO 51
<211> LENGTH: 81
<212> TYPE: DNA
<213> ORGANISM: Artificial Sequence
<220> FEATURE:
<223> OTHER INFORMATION: synthetic oligonucleotide

<400> SEQUENCE: 51
tccgggcggt gctggcggtc cgtacggccc tggtggcgca ggtgggccat atggtccggg    60
cggtgcgggc ggtccgtacg g                                             81
```

```
<210> SEQ ID NO 52
<211> LENGTH: 81
<212> TYPE: DNA
<213> ORGANISM: Artificial Sequence
<220> FEATURE:
<223> OTHER INFORMATION: synthetic oligonucleotide

<400> SEQUENCE: 52
gtacggaccg cccgcaccgc ccggaccata tgcccacct gcgccaccag ggccgtacgg      60
accgccagca ccgcccggac c                                              81

<210> SEQ ID NO 53
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 53
tggcgctggt ggcgccggtg gcgcaggtgg ctctggcggt gcgggcggtt ccgg           54

<210> SEQ ID NO 54
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 54
ggaaccgccc gcaccgccag agccacctgc gccaccggcg ccaccagcgc cacc           54

<210> SEQ ID NO 55
<211> LENGTH: 3238
<212> TYPE: DNA
<213> ORGANISM: Artificial Sequence
<220> FEATURE:
<223> OTHER INFORMATION: cloning vector pAZL

<400> SEQUENCE: 55
tgtcgagaag tactagagga tcataatcag ccataccaca tttgtagagg ttttacttgc     60
tttaaaaaac ctcccacacc tccccctgaa cctgaaacat aaaatgaatg caattgttgt    120
tgttaacttg tttattgcag cttataatgg ttacaaataa agcaatagca tcacaaattt    180
cacaaataaa gcattttttt cactgcattc tagttgtggt ttgtccaaac tcatcaatgt    240
atcttatcat gtctggatct gatcactgct tgagcctagg agatccgaac cagataagtg    300
aaatctagtt ccaaactatt ttgtcatttt taattttcgt attagcttac gacgctacac    360
ccagttccca tctattttgt cactcttccc taaataatcc ttaaaaactc catttccacc    420
cctcccagtt cccaactatt ttgtccgccc acagcggggc attttttcttc ctgttatgtt    480 tttaatcaaa catcctgcca actccatgtg acaaaccgtc atcttcggct acttttctc    540 tgtcacagaa tgaaaatttt tctgtcatct cttcgttatt aatgtttgta attgactgaa    600
tatcaacgct tatttgcagc ctgaatggcg aatgggacgc gccctgtagc ggcgcattaa    660
gcgcggcggg tgtggtggtt acgcgcagcg tgaccgctac acttgccagc gccctagcgc    720
ccgctccttt cgctttcttc ccttcctttc tcgccacgtt cgccggcttt ccccgtcaag    780
ctctaaatcg gggctccct ttaggttcc gatttagtgc tttacggcac ctcgacccca    840
aaaaacttga ttagggtgat ggttcacgta gtggccatc gccctgatag acggtttttc    900 gcccttgac gttggagtcc acgttcttta atagtggact cttgttccaa actggaacaa    960
```

```
cactcaaccc tatctcggtc tattcttttg atttataagg gattttgccg atttcggcct    1020
attggttaaa aaatgagctg atttaacaaa aatttaacgc gaattttaac aaaatattaa    1080
cgtttacaat ttcaggtggc acttttcggg gaaatgtgcg cggaacccct atttgtttat    1140
ttttctaaat acattcaaat atgtatccgc tcatgagaca ataaccctga taaatgcttc    1200
aataatattg aaaaggaag agtatgagta ttcaacattt ccgtgtcgcc cttattccct     1260 ttttgcggc attttgcctt cctgttttg ctcacccaga aacgctggtg aaagtaaaag      1320
atgctgaaga tcagttgggt gcacgagtgg gttacatcga actggatctc aacagcggta    1380
agatccttga gagttttcgc cccgaagaac gttttccaat gatgagcact tttaaagttc    1440
tgctatgtgg cgcggtatta tcccgtattg acgccgggca agagcaactc ggtcgccgca    1500
tacactattc tcagaatgac ttggttgagt actcaccagt cacagaaaag catcttacgg    1560
atggcatgac agtaagagaa ttatgcagtg ctgccataac catgagtgat aacactgcgg    1620
ccaacttact tctgacaacg atcggaggac cgaaggagct aaccgctttt ttgcacaaca    1680
tgggggatca tgtaactcgc cttgatcgtt gggaaccgga gctgaatgaa gccataccaa    1740
acgacgagcg tgacaccacg atgcctgtag caatggcaac aacgttgcgc aaactattaa    1800
ctggcgaact acttactcta gcttcccggc aacaattaat agactggatg gaggcggata    1860
aagttgcagg accacttctg cgctcggccc ttccggctgg ctggtttatt gctgataaat    1920
ctggagccgg tgagcgtggg tctcgcggta tcattgcagc actggggcca gatggtaagc    1980
cctcccgtat cgtagttatc tacacgacgg ggagtcaggc aactatggat gaacgaaata    2040
gacagatcgc tgagataggt gcctcactga ttaagcattg gtaactgtca gaccaagttt    2100
actcatatat actttagatt gatttaaaac ttcattttta atttaaaagg atctaggtga    2160
agatcctttt tgataatctc atgaccaaaa tcccttaacg tgagttttcg ttccactgag    2220
cgtcagaccc cgtagaaaag atcaaaggat cttcttgaga tcctttttt ctgcgcgtaa     2280 tctgctgctt gcaaacaaaa aaaccaccgc taccagcggt ggtttgtttg ccggatcaag    2340
agctaccaac tctttttccg aaggtaactg gcttcagcag agcgcagata ccaaatactg    2400
tccttctagt gtagccgtag ttaggccacc acttcaagaa ctctgtagca ccgcctacat    2460
acctcgctct gctaatcctg ttaccagtgg ctgctgccag tggcgataag tcgtgtctta    2520
ccgggttgga ctcaagacga tagttaccgg ataaggcgca gcggtcgggc tgaacggggg    2580
gttcgtgcac acagcccagc ttggagcgaa cgacctacac cgaactgaga tacctacagc    2640
gtgagcattg agaaagcgcc acgcttcccg aagggagaaa ggcggacagg tatccggtaa    2700
gcggcagggt cggaacagga gagcgcacga gggagcttcc agggggaaac gcctggtatc    2760
tttatagtcc tgtcgggttt cgccacctct gacttgagcg tcgatttttg tgatgctcgt    2820
caggggggcg gagcctatgg aaaaacgcca gcaacgcggc ctttttacgg ttcctggcct    2880
tttgctggcc ttttgctcac atgttctttc ctgcgttatc ccctgattct gtggataacc    2940
gtattaccgc ctttgagtga gctgataccg ctcgccgcag ccgaacgacc gagcgcagcg    3000
agtcagtgag cgaggaagcg gaagagcgcc tgatgcggta ttttctcctt acgcatctgt    3060
gcggtatttc acaccgcaga ccagccgcgt aacctggcaa atcggttac ggttgagtaa     3120 taaatggatg ccctgcgtaa gcgggtgtgg gcggacaata aagtcttaaa ctgaacaaaa    3180
tagatcgagg aggatccatg ggacgaattc acggctaatg aaagcttact gcacagct     3238
```